(12) United States Patent
Brocard et al.

(10) Patent No.: US 6,699,686 B1
(45) Date of Patent: Mar. 2, 2004

(54) MODIFIED NUCLEAR GLUCOCORTICOID RECEPTOR, FUSION PROTEIN, AND DNA FRAGMENTS CODING FOR SAID RECEPTOR AND SAID FUSION PROTEIN

(75) Inventors: Jacques Bertrand Brocard, Strasbourg (FR); Pierre Henri Chambon, Blaesheim (FR); Hinrich Gronemeyer, Oberkirch (DE); Daniel Metzger, Strasbourg (FR); Jean-Claude Nicolas, Montpellier (FR); Sylvie Roux, Montpellier (FR)

(73) Assignee: Association pour le Development de la Recherche en Genetique Moleculaire (ADEREGEM), Paris (FR)

( * ) Notice: Subject to any disclaimer, the term of this patent is extended or adjusted under 35 U.S.C. 154(b) by 0 days.

(21) Appl. No.: 09/125,491
(22) PCT Filed: Feb. 20, 1997
(86) PCT No.: PCT/FR97/00315
§ 371 (c)(1),
(2), (4) Date: Aug. 20, 1998
(87) PCT Pub. No.: WO97/31108
PCT Pub. Date: Aug. 28, 1997

(30) Foreign Application Priority Data

Feb. 20, 1996 (FR) .............................................. 96 02060

(51) Int. Cl.$^7$ ........................ C12N 15/00; C12N 15/63; C12N 5/00; C07H 21/02; C07H 21/04
(52) U.S. Cl. .................... 435/69.1; 435/320.1; 435/325; 536/23.1; 536/23.4; 536/23.51
(58) Field of Search .............................. 435/69.1, 70.1, 435/325, 455; 530/350, 827; 536/23.1, 23.5, 24.1, 23.4, 23.51

(56) References Cited

U.S. PATENT DOCUMENTS 5,215,916 A 6/1993 Simons, Jr. et al.
5,468,624 A 11/1995 Thompson et al.

FOREIGN PATENT DOCUMENTS

WO 88 03168 5/1988
WO 90 07517 7/1990

OTHER PUBLICATIONS

J. Biol. Chem., vol. 269, No. 46, Nov. 18, 1994, pp. 29010–29015, N. Warriar et al, "Hormone binding domain of human glucocorticoid receptor".
J. Biol. Chem., vol. 266, No. 33, Nov. 25, 1991, pp. 22075–22078, P.K. Chakraborti et al, "Creation of "Super" Glucocorticoid receptors by point mutations in the steroid biding domain".
Molecular and Cellular Biology, vol. 15, No. 2, Feb. 1995, pp. 1005–1013, XP000564501, W. Liu et al, "Hormone–independent repression of AP–1–Inducible collagenase promoter activity by Glucocorticoid receptors".
J. Biol. Chem., vol. 269, No. 11, Mar. 18, 1994, pp. 7914–7918, D. Chen et al, "The hormone–binding role of 2 cysteines near the C terminus of the mouse glucocorticoid receptor".
Natural Strutural Biology, vol. 3, Jan. 1, 1996, pp. 87–94, J.M. Wurtz et al, "A canonical structure for the ligand–binding domain of nuclear receptors".
Journal of Steroid Biochemistry and Molecular Biology, 55 (2) 1995. 135–146. Jewell C.M. et al, "Immunocytochemical analysis of hormone mediated nuclear translocation of wild type and mutant glucocorticoid receptors".
American Journal of Respiratory Cell and Molecular Biology 11 (1). 1994. 42–48, Lane S.J. et al, Chemical mutational analysis of the human glucocorticoid receptor cDNA in glucocorticoid–resistant bronchial asthma.
J. Clin. Invest., vol. 87, No. 2, Feb. 1991, pp. 680–686, Hurley et al, Point mutation causing a single amino acid substitution in the hormone binding domain of the gucocorticoid receptor in familial glucocorticoid resistance.
J. Clin. Invest., vol. 91, No. 5, May 1993, pp. 1918–1925, D.M. Malchoff et al, "A mutation of the glucocorticoid receptor in primary cortisol resistance".
Roux et al., Mutation of Isoleucine 747 by a Theronine Alters the Ligand Responsiceness of the Human Glucocorticiod Receptor, Molecular Endocrinology, vol. 10, No. 10, 1996, pp. 1214–1226.*
Warriar et al., Hormone Binding Domain of Human Glucocorticoid Receptor, The Journal of Bio. Chemistry, vol. 269, No. 46, Nov. 18, 1994, pp. 29010–29015.*
Chen et at., The Hormone–binding Role of 2 Cysteines Near the C Terminus of The Mouse Glucocorticiod Receptor, The Journal of Bio. Chemistry, vol. 169, No. 11, Mar. 18, 1994, pp. 7914–7918.*
Malchoff et al., A Mutation of the Glucocorticoid Repceptor in Primary Cortisol Resistance, J. Clin Invest., 1993, vol. 91, pp. 1918–1925.*
Hurley et al., Point Mutation Causing a Single Amino Acid Substitution in the Hormone Binding Domain of the Glucocorticoid Receptor in Familial Glucocorticoid Resistance, The Journal of Clinical Investigation, vol. 87, Feb. 1991, pp. 680–686.*
Lane et al., Chemical Mutational Analysis of the Human Glucocorticoid Receptor cDNA in Glucocorticoid–resistant Bronchial Astha, Am J. Respir Cell Mol. Biol., vol. 11, 1994, pp. 42–48.*

* cited by examiner

Primary Examiner—Ram R. Shukla
(74) Attorney, Agent, or Firm—Burns, Doane, Swecker & Mathis, L.L.P.

(57) ABSTRACT

A DNA fragment coding for a modified nuclear glucocorticoid receptor, particularly one mutated in the region coding for the ligand binding domain, so that receptor activity is more strongly inducible by a synthetic glucocorticoid ligand than by a natural glucocorticoid ligand, is disclosed. A recombination system inducible in mammals by means of a fusion protein produced between a recombinase and the binding domain of the ligand derived from the modified glucocorticoid receptor of which the activity is more strongly inducible by synthetic glucocorticoids than by natural glucocorticoids, is also disclosed.

19 Claims, 16 Drawing Sheets

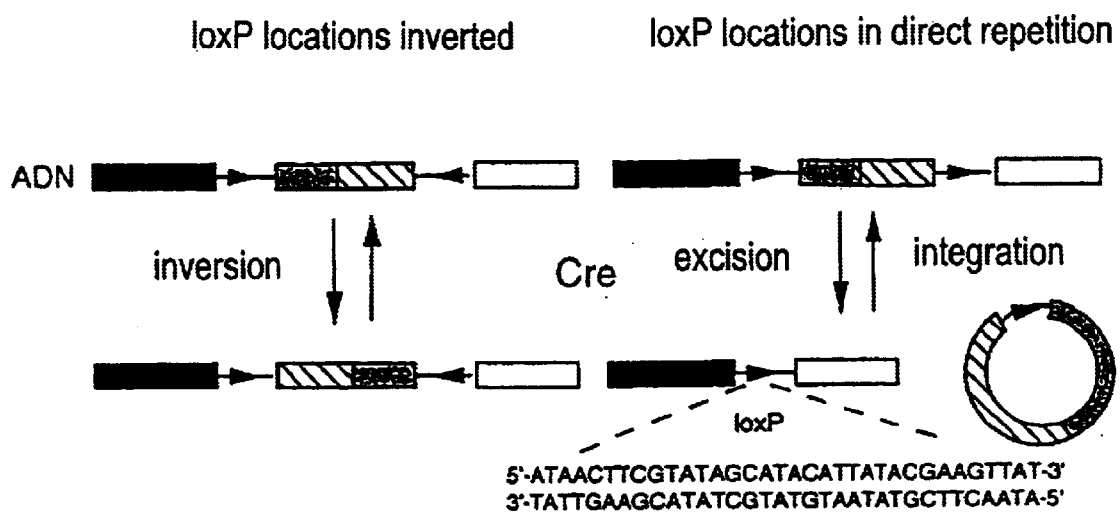
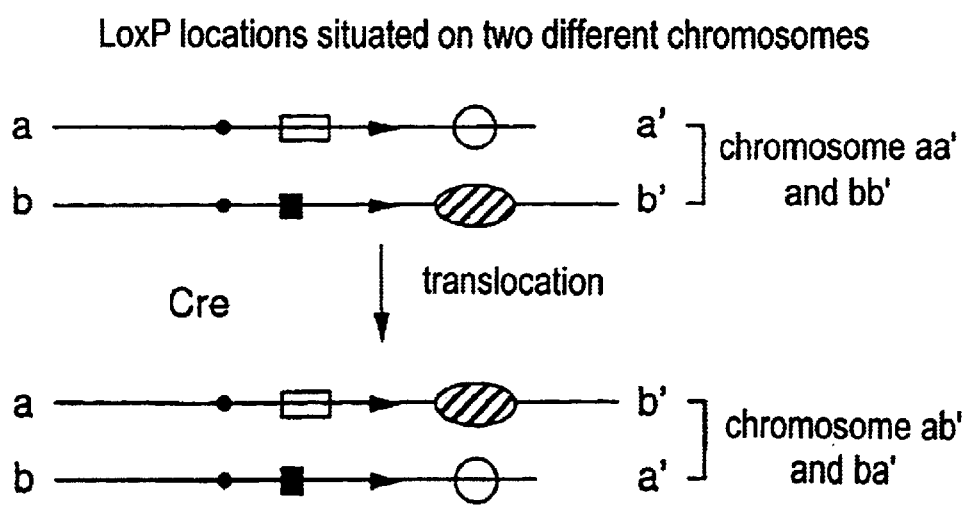
FIG. 1

Schematic representation of plasmid pCre-LBD[GR(I747/T)]

The sequences coded for Cre ave represented by ▦ for the aa 500-777 of hGR(I747/T) by ▨ for the aa 553-595 of hER by ▬

```
      SalI
   1  GTCGACTTCT  GAGGCGGAAA  GAACCAGCTG  TGGAATGTGT  GTCAGTTAGG
  51  GTGTGGAAAG  TCCCCAGGCT  CCCCAGCAGG  CAGAAGTATG  CAAAGCATGC
 101  ATCTCAATTA  GTCAGCAACC  AGGTGTGGAA  AGTCCCCAGG  CTCCCCAGCA
 151  GGCAGAAGTA  TGCAAAGCAT  GCATCTCAAT  TAGTCAGCAA  CCATAGTCCC
 201  GCCCCTAACT  CCGCCCATCC  CGCCCCTAAC  TCCGCCCAGT  TCCGCCCATT
 251  CTCCGCCCCA  TGGCTGACTA  ATTTTTTTTA  TTTATGCAGA  GGCCGAGGCC
 301  GCCTCGGCCT  CTGAGCTATT  CCAGAAGTAG  TGAGGAGGCT  TTTTTGGAGG
 351  CCTAGGCTTT  TGCAAAAAGC  TGGATCGATC  CTGAGAACTT  CAGGGTGAGT
 401  TTGGGGACCC  TTGATTGTTC  TTTCTTTTTC  GCTATTGTAA  AATTCATGTT
 451  ATATGGAGGG  GGCAAAGTTT  TCAGGGTGTT  GTTTAGAATG  GGAAGATGTC
 501  CCTTGTATCA  CCATGGACCC  TCATGATAAT  TTTGTTTCTT  TCACTTTCTA
 551  CTCTGTTGAC  AACCATTGTC  TCCTCTTATT  TTCTTTTCAT  TTTCTGTAAC
 601  TTTTTCGTTA  AACTTTAGCT  TGCATTTGTA  ACGAATTTTT  AAATTCACTT
 651  TTGTTTATTT  GTCAGATTGT  AAGTACTTTC  TCTAATCACT  TTTTTTTCAA
 701  GGCAATCAGG  GTATATTATA  TTGTACTTCA  GCACAGTTTT  AGAGAACAAT
 751  TGTTATAATT  AAATGATAAG  GTAGAATATT  TCTGCATATA  AATTCTGGCT
 801  GGCGTGGAAA  TATTCTTATT  GGTAGAAACA  ACTACATCCT  GGTCATCATC
 851  CTGCCTTTCT  CTTTATGGTT  ACAATGATAT  ACACTGTTTG  AGATGAGGAT
 901  AAAATACTCT  GAGTCCAAAC  CGGGCCCCTC  TGCTAACCAT  GTTCATGCCT
 951  TCTTCTTTTT  CCTACAGCTC  CTGGGCAACG  TGCTGGTTAT  TGTGCTGTCT
                                                          EcoRI
1001  CATCATTTTG  GCAAAGAATT  GTAATACGAC  TCACTATAGG  GCGAATTCCA
1051  CC ATG TCC AAT TTA CTG ACC GTA CAC CAA AAT TTG CCT GCA
      1▶Met Ser Asn Leu Leu Thr Val His Gln Asn Leu Pro Ala
1092  TTA CCG GTC GAT GCA ACG AGT GAT GAG GTT CGC AAG AAC CTG
    14▶Leu Pro Val Asp Ala Thr Ser Asp Glu Val Arg Lys Asn Leu
1134  ATG GAC ATG TTC AGG GAT CGC CAG GCG TTT TCT GAG CAT ACC
    28▶Met Asp Met Phe Arg Asp Arg Gln Ala Phe Ser Glu His Thr
1176  TGG AAA ATG CTT CTG TCC GTT TGC CGG TCG TGG GCG GCA TGG
    42▶Trp Lys Met Leu Leu Ser Val Cys Arg Ser Trp Ala Ala Trp
1218  TGC AAG TTG AAT AAC CGG AAA TGG TTT CCC GCA GAA CCT GAA
    56▶Cys Lys Leu Asn Asn Arg Lys Trp Phe Pro Ala Glu Pro Glu
1260  GAT GTT CGC GAT TAT CTT CTA TAT CTT CAG GCG CGC GGT CTG
    70▶Asp Val Arg Asp Tyr Leu Leu Tyr Leu Gln Ala Arg Gly Leu
1302  GCA GTA AAA ACT ATC CAG CAA CAT TTG GGC CAG CTA AAC ATG
    84▶Ala Val Lys Thr Ile Gln Gln His Leu Gly Gln Leu Asn Met
1344  CTT CAT CGT CGG TCC GGG CTG CCA CGA CCA AGT GAC AGC AAT
    98▶Leu His Arg Arg Ser Gly Leu Pro Arg Pro Ser Asp Ser Asn
1386  GCT GTT TCA CTG GTT ATG CGG CGG ATC CGA AAA GAA AAC GTT
   112▶Ala Val Ser Leu Val Met Arg Arg Ile Arg Lys Glu Asn Val
1428  GAT GCC GGT GAA CGT GCA AAA CAG GCT CTA GCG TTC GAA CGC
   126▶Asp Ala Gly Glu Arg Ala Lys Gln Ala Leu Ala Ph  Glu Arg
1470  ACT GAT TTC GAC CAG GTT CGT TCA CTC ATG GAA AAT AGC GAT
   140▶Thr Asp Phe Asp Gln Val Arg Ser Leu Met Glu Asn Ser Asp
```

FIG. 7A

```
1512  CGC  TGC  CAG  GAT  ATA  CGT  AAT  CTG  GCA  TTT  CTG  GGG  ATT  GCT
 154► Arg  Cys  Gln  Asp  Ile  Arg  Asn  Leu  Ala  Phe  Leu  Gly  Ile  Ala
1554  TAT  AAC  ACC  CTG  TTA  CGT  ATA  GCC  GAA  ATT  GCC  AGG  ATC  AGG
 168► Tyr  Asn  Thr  Leu  Leu  Arg  Ile  Ala  Glu  Ile  Ala  Arg  Ile  Arg
1596  GTT  AAA  GAT  ATC  TCA  CGT  ACT  GAC  GGT  GGG  AGA  ATG  TTA  ATC
 182► Val  Lys  Asp  Ile  Ser  Arg  Thr  Asp  Gly  Gly  Arg  Met  Leu  Ile
1638  CAT  ATT  GGC  AGA  ACG  AAA  ACG  CTG  GTT  AGC  ACC  GCA  GGT  GTA
 196► His  Ile  Gly  Arg  Thr  Lys  Thr  Leu  Val  Ser  Thr  Ala  Gly  Val
1680  GAG  AAG  GCA  CTT  AGC  CTG  GGG  GTA  ACT  AAA  CTG  GTC  GAG  CGA
 210► Glu  Lys  Ala  Leu  Ser  Leu  Gly  Val  Thr  Lys  Leu  Val  Glu  Arg
1722  TGG  ATT  TCC  GTC  TCT  GGT  GTA  GCT  GAT  GAT  CCG  AAT  AAC  TAC
 224► Trp  Ile  Ser  Val  Ser  Gly  Val  Ala  Asp  Asp  Pro  Asn  Asn  Tyr
1764  CTG  TTT  TGC  CGG  GTC  AGA  AAA  AAT  GGT  GTT  GCC  GCG  CCA  TCT
 238► Leu  Phe  Cys  Arg  Val  Arg  Lys  Asn  Gly  Val  Ala  Ala  Pro  Ser
1806  GCC  ACC  AGC  CAG  CTA  TCA  ACT  CGC  GCC  CTG  GAA  GGG  ATT  TTT
 252► Ala  Thr  Ser  Gln  Leu  Ser  Thr  Arg  Ala  Leu  Glu  Gly  Ile  Phe
1848  GAA  GCA  ACT  CAT  CGA  TTG  ATT  TAC  GGC  GCT  AAG  GAT  GAC  TCT
 266► Glu  Ala  Thr  His  Arg  Leu  Ile  Tyr  Gly  Ala  Lys  Asp  Asp  Ser
1890  GGT  CAG  AGA  TAC  CTG  GCC  TGG  TCT  GGA  CAC  AGT  GCC  CGT  GTC
 280► Gly  Gln  Arg  Tyr  Leu  Ala  Trp  Ser  Gly  His  Ser  Ala  Arg  Val
1932  GGA  GCC  GCG  CGA  GAT  ATG  GCC  CGC  GCT  GGA  GTT  TCA  ATA  CCG
 294► Gly  Ala  Ala  Arg  Asp  Met  Ala  Arg  Ala  Gly  Val  Ser  Ile  Pro
1974  GAG  ATC  ATG  CAA  GCT  GGT  GGC  TGG  ACC  AAT  GTA  AAT  ATT  GTC
 308► Glu  Ile  Met  Gln  Ala  Gly  Gly  Trp  Thr  Asn  Val  Asn  Ile  Val
2016  ATG  AAC  TAT  ATC  CGT  AAC  CTG  GAT  AGT  GAA  ACA  GGG  GCA  ATG
 322► Met  Asn  Tyr  Ile  Arg  Asn  Leu  Asp  Ser  Glu  Thr  Gly  Ala  Met
                                                 XhoI
2058  GTG  CGC  CTG  CTG  GAA  GAT  GGC  GAT  CTC  GAG  ATT  CAG  CAG  GCC
 336► Val  Arg  Leu  Leu  Glu  Asp  Gly  Asp  Leu  Glu  Ile  Gln  Gln  Ala
2100  ACT  ACA  GGA  GTC  TCA  CAA  GAA  ACC  TCT  GAA  AAT  CCT  GGT  AAC
 350► Thr  Thr  Gly  Val  Ser  Gln  Glu  Thr  Ser  Glu  Asn  Pro  Gly  Asn
2142  AAA  ACA  ATA  GTT  CCT  GCA  ACG  TTA  CCA  CAA  CTC  ACC  CCT  ACC
 364► Lys  Thr  Ile  Val  Pro  Ala  Thr  Leu  Pro  Gln  Leu  Thr  Pro  Thr
2184  CTG  GTG  TCA  CTG  TTG  GAG  GTT  ATT  GAA  CCT  GAA  GTG  TTA  TAT
 378► Leu  Val  Ser  Leu  Leu  Glu  Val  Ile  Glu  Pro  Glu  Val  Leu  Tyr
2226  GCA  GGA  TAT  GAT  AGC  TCT  GTT  CCA  GAC  TCA  ACT  TGG  AGG  ATC
 392► Ala  Gly  Tyr  Asp  Ser  Ser  Val  Pro  Asp  Ser  Thr  Trp  Arg  Ile
2268  ATG  ACT  ACG  CTC  AAC  ATG  TTA  GGA  GGG  CGG  CAA  GTG  ATT  GCA
 406► Met  Thr  Thr  Leu  Asn  Met  Leu  Gly  Gly  Arg  Gln  Val  Ile  Ala
2310  GCA  GTG  AAA  TGG  GCA  AAG  GCA  ATA  CCA  GGT  TTC  AGG  AAC  TTA
 420► Ala  Val  Lys  Trp  Ala  Lys  Ala  Ile  Pro  Gly  Phe  Arg  Asn  Leu
2352  CAC  CTG  GAT  GAC  CAA  ATG  ACC  CTA  CTG  CAG  TAC  TCC  TGG  ATG
 434► His  Leu  Asp  Asp  Gln  Met  Thr  Leu  Leu  Gln  Tyr  Ser  Trp  Met
2394  TTT  CTT  ATG  GCA  TTT  GCT  CTG  GGG  TGG  AGA  TCA  TAT  AGA  CAA
 448► Phe  Leu  Met  Ala  Phe  Ala  Leu  Gly  Trp  Arg  Ser  Tyr  Arg  Gln
2436  TCA  AGT  GCA  AAC  CTG  CTG  TGT  TTT  GCT  CCT  GAT  CTG  ATT  ATT
 462► Ser  Ser  Ala  Asn  Leu  Leu  Cys  Phe  Ala  Pro  Asp  Leu  Ile  Ile
```

FIG. 7B

```
2478 AAT GAG CAG AGA ATG ACT CTA CCC TGC ATG TAC GAC CAA TGT
476▶Asn Glu Gln Arg Met Thr Leu Pro Cys Met Tyr Asp Gln Cys
2520 AAA CAC ATG CTG TAT GTT TCC TCT GAG TTA CAC AGG CTT CAG
490▶Lys His Met Leu Tyr Val Ser Ser Glu Leu His Arg Leu Gln
2562 GTA TCT TAT GAA GAG TAT CTC TGT ATG AAA ACC TTA CTG CTT
504▶Val Ser Tyr Glu Glu Tyr Leu Cys Met Lys Thr Leu Leu Leu
2604 CTC TCT TCA GTT CCT AAG GAC GGT CTG AAG AGC CAA GAG CTA
518▶Leu Ser Ser Val Pro Lys Asp Gly Leu Lys Ser Gln Glu Leu
2646 TTT GAT GAA ATT AGA ATG ACC TAC ATC AAA GAG CTA GGA AAA
532▶Phe Asp Glu Ile Arg Met Thr Tyr Ile Lys Glu Leu Gly Lys
2688 GCC ATT GTC AAG AGG GAA GGA AAC TCC AGC CAG AAC TGG CAG
546▶Ala Ile Val Lys Arg Glu Gly Asn Ser Ser Gln Asn Trp Gln
2730 CGG TTT TAT CAA CTG ACA AAA CTC TTG GAT TCT ATG CAT GAA
560▶Arg Phe Tyr Gln Leu Thr Lys Leu Leu Asp Ser Met His Glu
2772 GTG GTT GAA AAT CTC CTT AAC TAT TGC TTC CAA ACA TTT TTG
574▶Val Val Glu Asn Leu Leu Asn Tyr Cys Phe Gln Thr Phe Leu
2814 GAT AAG ACC ATG TCC ACC GAG TTC CCC GAG ATG TTA GCT GAA
588▶Asp Lys Thr Met Ser Thr Glu Phe Pro Glu Met Leu Ala Glu
2856 ATC ATC ACC AAT CAG ATA CCA AAA TAT TCA AAT GGA AAT ATC
602▶Ile Ile Thr Asn Gln Ile Pro Lys Tyr Ser Asn Gly Asn Ile
                                            KpnI
2898 AAA AAA CTT CTG TTT CAT CAA AAG GGT ACC AGC CGT GGA GGG
616▶Lys Lys Leu Leu Phe His Gln Lys Gly Thr Ser Arg Gly Gly
2940 GCA TCC GTG GAG GAG ACG GAC CAA AGC CAC TTG GCC ACT GCG
630▶Ala Ser Val Glu Glu Thr Asp Gln Ser His Leu Ala Thr Ala
2982 GGC TCT ACT TCA TCG CAT TCC TTG CAA AAG TAT TAC ATC ACG
644▶Gly Ser Thr Ser Ser His Ser Leu Gln Lys Tyr Tyr Ile Thr
3024 GGG GAG GCA GAG GGT TTC CCT GCC ACA GTC TGA GAGCTCCCTG
658▶Gly Glu Ala Glu Gly Phe Pro Ala Thr Val ***
     EcoRI
3067 GAATTCGGAT CTTATTAAAG CAGAACTTGT TTATTGCAGC TTATAATGGT
3117 TACAAATAAA GCAATAGCAT CACAAATTTC ACAAATAAAG CATTTTTTTC
3167 ACTGCATTCT AGTTGTGGTT TGTCCAAACT CATCAATGTA TCTTATCATG
     SalI
3217 TCTGGTCGAC TCTAGACTCT TCCGCTTCCT CGCTCACTGA CTCGCTGCGC
3267 TCGGTCGTTC GGCTGCGGCG AGCGGTATCA GCTCACTCAA AGGCGGTAAT
3317 ACGGTTATCC ACAGAATCAG GGGATAACGC AGGAAAGAAC ATGTGAGCAA
3367 AAGGCCAGCA AAAGGCCAGG AACCGTAAAA AGGCCGCGTT GCTGGCGTTT
3417 TTCCATAGGC TCCGCCCCCC TGACGAGCAT CACAAAAATC GACGCTCAAG
3467 TCAGAGGTGG CGAAACCCGA CAGGACTATA AAGATACCAG GCGTTTCCCC
3517 CTGGAAGCTC CCTCGTGCGC TCTCCTGTTC CGACCCTGCC GCTTACCGGA
3567 TACCTGTCCG CCTTTCTCCC TTCGGGAAGC GTGGCGCTTT CTCATAGCTC
3617 ACGCTGTAGG TATCTCAGTT CGGTGTAGGT CGTTCGCTCC AAGCTGGGCT
3667 GTGTGCACGA ACCCCCCGTT CAGCCCGACC GCTGCGCCTT ATCCGGTAAC
3717 TATCGTCTTG AGTCCAACCC GGTAAGACAC GACTTATCGC CACTGGCAGC
3767 AGCCACTGGT AACAGGATTA GCAGAGCGAG GTATGTAGGC GGTGCTACAG
3817 AGTTCTTGAA GTGGTGGCCT AACTACGGCT ACACTAGAAG GACAGTATTT
3867 GGTATCTGCG CTCTGCTGAA GCCAGTTACC TTCGGAAAAA GAGTTGGTAG
3917 CTCTTGATCC GGCAAACAAA CCACCGCTGG TAGCGGTGGT TTTTTTGTTT
```

FIG. 7C

```
3967  GCAAGCAGCA GATTACGCGC AGAAAAAAAG GATCTCAAGA AGATCCTTTG
4017  ATCTTTTCTA CGGGGTCTGA CGCTCAGTGG AACGAAAACT CACGTTAAGG
4067  GATTTTGGTC ATGAGATTAT CAAAAAGGAT CTTCACCTAG ATCCTTTTAA
4117  ATTAAAAATG AAGTTTTAAA TCAATCTAAA GTATATATGA GTAAACTTGG
4167  TCTGACAGTT ACCAATGCTT AATCAGTGAG GCACCTATCT CAGCGATCTG
4217  TCTATTTCGT TCATCCATAG TTGCCTGACT CCCCGTCGTG TAGATAACTA
4267  CGATACGGGA GGGCTTACCA TCTGGCCCCA GTGCTGCAAT GATACCGCGA
4317  GACCCACGCT CACCGGCTCC AGATTTATCA GCAATAAACC AGCCAGCCGG
4367  AAGGGCCGAG CGCAGAAGTG GTCCTGCAAC TTTATCCGCC TCCATCCAGT
4417  CTATTAATTG TTGCCGGGAA GCTAGAGTAA GTAGTTCGCC AGTTAATAGT
4467  TTGCGCAACG TTGTTGCCAT TGCTACAGGC ATCGTGGTGT CACGCTCGTC
4517  GTTTGGTATG GCTTCATTCA GCTCCGGTTC CCAACGATCA AGGCGAGTTA
4567  CATGATCCCC CATGTTGTGC AAAAAAGCGG TTAGCTCCTT CGGTCCTCCG
4617  ATCGTTGTCA GAAGTAAGTT GGCCGCAGTG TTATCACTCA TGGTTATGGC
4667  AGCACTGCAT AATTCTCTTA CTGTCATGCC ATCCGTAAGA TGCTTTTCTG
4717  TGACTGGTGA GTACTCAACC AAGTCATTCT GAGAATAGTG TATGCGGCGA
4767  CCGAGTTGCT CTTGCCCGGC GTCAATACGG GATAATACCG CGCCACATAG
4817  CAGAACTTTA AAAGTGCTCA TCATTGGAAA ACGTTCTTCG GGGCGAAAAC
4867  TCTCAAGGAT CTTACCGCTG TTGAGATCCA GTTCGATGTA ACCCACTCGT
4917  GCACCCAACT GATCTTCAGC ATCTTTTACT TTCACCAGCG TTTCTGGGTG
4967  AGCAAAAACA GGAAGGCAAA ATGCCGCAAA AAAGGGAATA AGGGCGACAC
5017  GGAAATGTTG AATACTCATA CTCTTCCTTT TTCAATATTA TTGAAGCATT
5067  TATCAGGGTT ATTGTCTCAT GAGCGGATAC ATATTTGAAT GTATTTAGAA
5117  AAATAAACAA ATAGGGGTTC CGCGCACATT TCCCCGAAAA GTGCCACCTG
5167  ACGTCTAAGA AACCATTATT ATCATGACAT TAACCTATAA AAATAGGCGT
5217  ATCACGAGGC CCTTTCGTC TCGCGCGTTT CGGTGATGAC GGTGAAAACC
5267  TCTGACACAT GCAGCTCCCG GAGACGGTCA CAGCTTGTCT GTAAGCGGAT
5317  GCCGGGAGCA GACAAGCCCG TCAGGGCGCG TCAGCGGGTG TTGGCGGGTG
5367  TCGGGGCTGG CTTAACTATG CGGCATCAGA GCAGATTGTA CTGAGAGTGC
5417  ACCATATGCG GTGTGAAATA CCGCACAGAT GCGTAAGGAG AAAATACCGC
5467  ATCAGGAAAT TGTAAACGTT AATATTTTGT TAAAATTCGC GTTAAATTTT
5517  TGTTAAATCA GCTCATTTTT TAACCAATAG GCCGAAATCG GCAAAATCCC
5567  TTATAAATCA AAAGAATAGA CCGAGATAGG GTTGAGTGTT GTTCCAGTTT
5617  GGAACAAGAG TCCACTATTA AAGAACGTGG ACTCCAACGT CAAAGGGCGA
5667  AAAACCGTCT ATCAGGGCGA TGCCCACTA CGTGAACCAT CACCCTAATC
5717  AAGTTTTTTG GGGTCGAGGT GCCGTAAAGC ACTAAATCGG AACCCTAAAG
5767  GGAGCCCCCG ATTTAGAGCT TGACGGGGAA AGCCGGCGAA CGTGGCGAGA
5817  AAGGAAGGGA AGAAAGCGAA AGGAGCGGGC GCTAGGGCGC TGGCAAGTGT
5867  AGCGGTCACG CTGCGCGTAA CCACCACACC CGCCGCGCTT AATGCGCCGC
5917  TACAGGGCGC GTCGCGCCAT TCGCCATTCA GGCTGCGCAA CTGTTGGGAA
5967  GGGCGATCGG TGCGGGCCTC TTCGCTATTA CGCCAGCTGG CGAAAGGGGG
6017  ATGTGCTGCA AGGCGATTAA GTTGGGTAAC GCCAGGGTTT TCCCAGTCAC
6067  GACGTTGTAA AACGACGGCC AGTGAATT
```

FIG. 7D

MODIFIED NUCLEAR GLUCOCORTICOID RECEPTOR, FUSION PROTEIN, AND DNA FRAGMENTS CODING FOR SAID RECEPTOR AND SAID FUSION PROTEIN

FIELD OF THE INVENTION

The present invention relates to a DNA fragment coding for a modified nuclear glucocorticoid receptor (GR), and a DNA fragment coding for a ligand binding domain (LBD) of said receptor, as well as a DNA fragment coding for a fusion protein comprising said receptor of said ligand binding domain of said receptor fused to a protein whose activity is induced in the presence of glucocorticoid ligands.

The present invention also relates to a modified nuclear glucocorticoid receptor, in particular the human receptor and its modified ligand binding domain, as well as a fusion protein comprising said receptor or said ligand binding domain.

The present invention also relates to a vector for conditionally expressing a protein, in particular a foreign protein, in human or animal host cells, in particular mammalian cells. The present invention also relates to a method of expressing a protein in said cells. Moreover, the present invention relates to a method for the conditional excision, insertion, inversion or translocation of a DNA fragment in human or animal, in particular mammalian, host cells.

The present invention relates in addition, to a vector for transferring a DNA fragment into said human or animal, in particular mammalian, host cells and to its use as a medicament, as a tool for analyzing and studying the function of a gene as well as to a method of treating cells ex vivo or in vitro.

Finally, the present invention relates to human or animal cells transfected with an expression and/or transfer vector according to the invention as well as to transgenic animals derived therefrom.

BACKGROUND OF THE INVENTION

The glucocorticoid receptor (GR) is a protein for regulating transcription of genes which mediate the action of glucocorticoids in target cells. The GR and other members of the super family of nuclear receptors (ligand-activated transcription factors) exhibit a common modular structure. The variable N-terminal region contains the constitutive transactivation activity AF-1. The core DNA binding domain (DBD) is highly conserved between various species and allows the binding of the receptor to its related DNA response element (GRE in the case of GR). The ligand binding domain (LBD), located in the C-terminal region of GR, not only binds the ligand, but also comprises multiple distinct activities: a surface for interaction with hsp90 and a distinct surface for homodimerization, a nuclear localization signal and a ligand-dependent transactivation function AF-2 (for review articles and references, see (1–5)). The LBD domain is highly conserved between various species. A transactivation function AF-2 has been identified in the C-terminal part of various LBDs (6–10). The integrity of the core part of the region containing AF-2 is required for the ligand-dependent transcription activation by the corresponding nuclear receptors, and for the interaction between this region and related transcriptional intermediate factors (TIF, also called coactivators or mediators) (11–19). A general model has been proposed (19) in which the binding of the ligand induces a conformational change in the ligand binding domain by calling into play in particular the C-terminal region harboring the core part of AF-2, thus generating a surface for an effective interaction with the TIFs. The LBDs of the nuclear receptors contain conserved regions possessing a canonic structure In the form of a helix. These structural data have made it possible to carry out a common alignment or the LBDs of all nuclear receptors. The H12 helix contains the transactivation function AF-2 (19). The m no acids of helices H11 and H12, in particular of the glucocorticoid receptors from various species such as humans, rats, mice and xenopus, are conserved.

Several mutations in the LBD of GR have been previously described. Two major types of mutation can be distinguished:

the first type consists in mutations which positively or negatively affect the affinity for binding to the ligand. For example, the replacements of the cysteine residue 656 by glycine in rat GR (20) and of the methionine residue 565 by arginine or of the alanine residue 573 by glutamine in the human GR (hGR) (21) increase the affinity for binding to the ligand and lead to a shift in the dose-response curve for the transactivation in the direction of the lowest ligand concentrations. These mutants are consequently designated "super GR". Likewise, mutants have been reported which have a lower affinity for binding to the ligand (21–24). LBD mutations which shift the ligand dose-response curve in the direction of the highest ligand concentrations result from an altered hormone binding affinity (25–26);

the second group of LBD mutants comprises those which affect the transcriptional activation function (AF-2) without altering the binding to the ligand. As examples, there may be mentioned mutations in the region containing AF-2 which are linked to a loss or a decrease in the transactivation potential, but do not affect the affinity for binding to the ligand (6–10).

The fusion of the ligand binding domain (LBD) of nuclear receptors to heterologous proteins has made it possible to control their activity in numerous cases.

The activities of Myc, c-Abl, Src, erbB1, Raf, E1A Cre and FLP may be modulated by producing fusion proteins with the LBD of nuclear receptors (27–29). However, the ligands for these receptors are present in numerous biological systems and are thus capable of inducing a basal activity level. To avoid such problems, a mutated LBD of the estrogen receptor (ER) has been fused to the c-Myc protein (30), or to the Cre and FLP recombinases (28 and 29).

The recombinases of the family of λ integrases catalyze the excision, insertion, inversion or translocation of DNA fragments at the level of specific sites of recognition of said recombinases (31–36). The recombinases are active in animal cells (35).

The Cre recombinase, an integrase of 38 KDa from bacteriophage P1, catalyzes recombination between two DNA sequences of 34 base pairs called loxP in the absence of cofactors (32, FIG. 1).

The position on one or more DNA molecules and the orientation of loxP sites relative to each other determine the type of function of the recombinase, excision, insertion, inversion or translocation, in particular the Cre recombinase (FIG. 1). Thus, the recombinase activity of Cre is an inversion when two LoxP sites are head-to-tail on the same DNA fragment and an excision when the LoxP sites are a direct repeat on the same DNA fragment. The recombinase activity is an insertion when a loxP site is present on a DNA fragment, it being possible for a DNA molecule such as a plasmid containing a loxP site to be inserted at the level of said loxP site (FIG. 1). The Cre recombinase can also induce a translocation between two chromosomes provided that a loxP site is present on each of them (37) (FIG. 1). More generally, the Cre recombinase is therefore capable of inducing recombination between one or more different DNA molecules provided that they carry loxP sites.

Likewise, the FLP recombinase, a recombinase of 43 KDa from *Saccharomyces cerevisiae*, is capable of the same type of action on DNA fragments containing recognition sites FRT (34).

By producing a fusion protein (chimera) between the Cre recombinase and the C-terminal region of the human receptor for estrogens containing a Valine at position 400, a molecule is obtained which is capable of excising, in the presence of the receptor ligand, estradiol, the DNA sequences located between two loxP sites, as well as one of the loxP sites, when the latter are a direct repeat, whereas in the absence of ligand, the excision does not take place (28).

The activity of the FLP recombinase can also be regulated by producing chimeras between the FLP and the binding domain of nuclear receptors. By fusing the FLP with the LBD of the estrogen receptor or of the glucocorticoid receptor in the absence of ligand, the recombinase activity is very low, whereas it is rapidly induced by the respective ligands for the LBDs (29).

However, the use of fusion proteins between recombinases and LBDs of nuclear receptors to excise, in a controlled manner, DNA fragments situated between sites of recognition of said recombinases can pose a problem, given that the ligand concentrations present in animals or in cell culture media may be sufficient to induce, at least partially, the recombinase activity.

BRIEF SUMMARY OF THE INVENTION

The present invention provides a recombination system inducible in animals, in particular mammals, by virtue of the use of a fusion protein produced between a recombinase and the ligand binding domain derived from the glucocorticoid receptor whose activity is inducible by synthetic glucocorticoids but not by natural glucocorticoids in particular at concentrations of less than $10^{-6}$ M, that is to say physiological concentrations.

To avoid induction of the recombinase activity of the chimeric protein by the endogenous ligands, the present invention indeed proposes to provide a mutation in the LBD of the glucocorticoid receptor allowing It to be more strongly activated in the presence of synthetic glucocorticoid ligands than in the presence of natural glucocorticoid ligands at physlologlcal concentrations.

The subject of the present invention is indeed a modified nuclear glucocorticoid receptor, in particular mutated in the region of the ligand binding domain, so that the activity of said receptor is more strongly inducible by a synthetic glucocorticoid ligand than by a natural glucocorticoid ligand.

According to the present invention, "(mutated) glucocorticoid receptor more strongly inducible by a synthetic glucocorticoid ligand than by a natural glucocorticoid ligand" is understood to mean that the activity of the mutated receptor according to the invention is induced more strongly by synthetic glucocorticoid ligands than by natural glucocorticoid ligands at a given concentration and that the mutated glucocorticoid receptor according to the invention is a lot less sensitive to the natural glucocorticoids than the wild-type receptor.

"Activity of said receptor" is understood to mean here the transcriptional activity of said receptor and/or, where appropriate, the activity of regulating the activity of a protein fused to said receptor or to said ligand binding domain, induced in the presence of glucocorticoids. There may be mentioned more particularly the activity of a recombinase protein fused to said receptor or to said ligand binding domain of said receptor.

"Natural glucocorticoids" are understood to mean here steroid hormones secreted by the cortex of the adrenal glands such as cortisol, corticosterone or aldosterone. "Synthetic glucocorticoids" are understood to mean chemically synthesized agonists of said receptor for the relevant activity. There may be mentioned, among the letter, dexamethasone, triamcimolone acetonide RU 486, RU 28362, bimedrazol, fluocinolone acetonide.

Some synthetic ligands will be agonists for inducing said particular activity of the receptor and antagonists in relation to another activity of the receptor. Thus, the compound RU 486 induces the activity of a recombinase protein fused to said receptor or to said ligand binding domain of the receptor but does not induce the transcriptional activity of the receptor.

The synthetic glucocorticoid ligand may bind to the (nonmutated) wild-type nuclear receptor, but it is possible that said synthetic ligand binds to the mutated receptor and not to the natural receptor. It is also possible that if said synthetic ligand binds to the wild-type receptor, the activity of the latter is nevertheless not induced by binding to the synthetic ligand.

A mutation has in particular been identified in the LBD domain of the nuclear glucocorticoid receptors (isoleucine→threonine) situated between helices H11 and H12 (19). This mutation causes a loss of activity for the receptor in the presence of natural glucocorticoids. More precisely, this glucocorticoid receptor mutated between H11 and H12 has no or very little transcriptional activity in the presence of natural glucocorticoids at their natural physiological concentrations, in particular concentrations of less than $10^{-6}$ M. Its activity may, however, be induced by synthetic glucocorticoid ligands, in particular dexamethasone (dex).

The subject of the present invention is more particularly a mutated human receptor called hGR (I747/T) characterized in that it has, as sequence, the amino acid sequence of the human wild-type nuclear glucocorticoid receptor with an isoleucine→threonine mutation at position 747, and still more particularly a modified human nuclear receptor which has, as amino acid sequence, a sequence substantially as represented in the SEQ ID NO: 1.

The isoleucine 747 to threonine mutation in the C-terminal part of the ligand binding domain (LBD) of the glucocorticoid receptor alters the capacity of the natural ligands to induce the transactivation activity thereof. Natural glucocorticoids such as cortisol, aldosterone or corticosterone are very weakly active or completely inactive with the GR mutant (I747/T), whereas synthetic glucocorticoids such as dexamethasone (Dex) efficiently stimulate the GR-mediated transactivation (I747/T). However, the corresponding ligand dose-response curve, for the transactivation induced by Dex, is shifted toward the highest concentrations, compared with that obtained with the wild-type (WT) GR. Neither the shift nor the inability of cortisol to efficiently activate GR (I747/T) are due to an altered affinity for binding to the ligand in vitro.

Indeed, the mutation in the LBD of GR (I747/T) does not substantially alter the affinity for binding to the ligand in vitro. However, this mutant exhibits a substantial shift compared with the WT GR for the activity curve toward the high ligand concentrations.

Moreover, so-called physiological concentrations of natural glucocorticoid ligands which are sufficient to activate the WT GR cause only a residual or zero activity in the mutant GR.

This mutant differs from the other GR LBD mutants previously described (22, 38) whose altered activation function is closely correlated with a modification in their properties for binding to the ligand in vitro.

The subject of the present invention is also a ligand binding domain of the nuclear glucocorticoid receptor according to the invention and particularly the LBD domain [GR(I747/T)], characterized in that it has an isoleucine→threonine mutation between helices H11 and H12. More particularly, it has, as sequence, the ainmo acid sequence of the ligand binding domain of the human glucocorticoid receptor substantially as represented in SID No. 1 from amino acid 532 to amino acid 777 with an isoleucine→threonine mutation at position 747.

The present invention also provides a DNA fragment encoding a modified nuclear glucocorticoid receptor, in particular mutated in the region of the ligand binding domain (LBD) according to the invention, as well as a DNA fragment encoding a ligand binding domain (LBD) of the modified receptor according to the invention.

The subject of the present invention is therefore more precisely a DNA fragment encoding a wild-type nuclear glucocorticoid receptor with an isoleucine to threonine mutation situated between helices H11 and H12 of the amino acid sequence of said receptor, and still more particularly a DNA fragment, characterized in that it has, as sequence, a coding sequence of the human nuclear glucocorticoid receptor whose amino acid sequence is substantially that represented in SEQ ID NO: 1.

In one embodiment, the subject of the present invention is a DNA fragment, characterized in that it has, as sequence, the cDNA sequence of the human nuclear glucocorticoid receptor substantially as represented in SEQ ID NO: 1 comprising the ACC codon coding for threonine at position 747 of the amino acid sequence of said receptor.

Likewise, the subject of the present invention is a DNA fragment encoding the ligand binding domain (LBD) of the modified nuclear glucocorticoid receptor with an isoleucine→threonine mutation situated between helices H11 and H12 and in particular at a position corresponding to position 747 of the amino acid sequence of the human nuclear glucocorticoid receptor.

More particularly, the present invention provides a DNA fragment encoding the ligand binding domain of the modified human nuclear glucocorticoid receptor, characterized in that it has, as sequence, a sequence coding for the amino acids of the ligand binding domain of the human nuclear glucocorticoid receptor whose amino acid sequence is substantially as represented in SEQ ID NO: 1 from amino acid 532 to amino acid 777.

Still more particularly, the present invention provides a DNA fragment, characterized in that it has, as sequence, the cDNA sequence encoding the ligand binding domain (LBD) of the human nuclear glucocorticoid receptor substantially as represented in SEQ ID NO: 1 from codon 532 to codon 777 with the ACC codon at position 747.

The subject of the present invention is, in addition, a vector system for conditionally expressing a protein, in particular a foreign protein, in host cells comprising an element for control of transcription inducible by a complex formed by a nuclear glucocorticoid receptor and a ligand, characterized in that it comprises:

a first DNA fragment consisting of a DNA fragment coding for said protein under the control of elements ensuring its expression in said host cells, said elements ensuring its expression comprising a sequence for control of transcription (RE) inducible by the receptor according to the invention complexed with a synthetic glucocorticoid ligand, and a second DNA fragment consisting of a functional DNA fragment coding for said receptor according to the invention or only part of said fragment comprising the region which recognizes the ligand (LBD) according to the invention, and the DNA binding region (DBD) which attaches to said sequence for control of transcription (RE), it being possible for said first and second DNA fragments to be carried by the same vector or two vectors separately.

Some cells have endogenous GR which may be activated by natural ligands and synthetic ligands. If it is desired to activate a given gene at will in such cells, without it being possible for it to be activated by endogenous ligands or by endogenous receptors, it is necessary for this gene to contain an RE different from GRE and to use a chimeric activator comprising the corresponding DBD and a mutated LBD according to the invention. This gene can therefore be activated by synthetic ligands, but not by natural ligands.

Accordingly, in one embodiment, the DNA binding domain (DBD) of the glucocorticoid receptor is replaced by that of another transactivator, in particular that of the yeast protein Gal 4 and the sequence for control of transcription (RE) of the glucocorticoid receptor is replaced by that of another transactivator, in particular the 17 mer (17m) sequence recognized by the Gal4 protein.

The subject of the present invention is therefore also a method of expressing a foreign protein in human or animal, in particular mammalian, cells, characterized in that cells are cultured which contain an expression vector system according to the invention, and in that said synthetic ligand is added to the culture medium and then the protein synthesized is recovered.

The synthetic glucocorticoid ligands diffuse freely in the cells when they added to the culture medium or injected into an animal.

In this method, a synthetic ligand chosen from dexamethasone, triamcinolone acetonide, RU2836, bimetrazole, deacylcortivazol and fluocinolone acetonide will be used in particular.

The subject of the present invention is, in addition, a fusion protein comprising a receptor according to the invention or a ligand binding domain according to the invention and a protein whose activity is more strongly inducible by binding of said receptor or of said ligand binding domain (LBD) of said receptor with a said synthetic glucocorticoid ligand than with a natural glucocorticoid ligand.

In particular, the subject of the present invention is a fusion protein which comprises a recombinase protein and more particularly of the family of λ integrases and still more particularly the Cre protein of the bacteriophage $P_1$.

In one embodiment, the fusion protein comprises the C-terminal part of the hinge region D of the human nuclear glucocorticoid receptor, intercalated between the Cre protein and said ligand binding domain of the modified receptor according to the invention.

The actual recombinase activity of the fusion protein is similar to that of Cre. It therefore makes it possible, like Cre, to excise or reverse the DNA sequences located between the loxP sites, to insert a plasmid containing a loxP site at the level of a loxP site located in the genome, or to carry out a translocation between two chromosomes each containing a loxP site.

The subject of the present invention is also a fusion gene coding for the fusion protein according to the invention comprising a DNA fragment coding for a modified nuclear glucocorticoid receptor or a ligand binding domain of said receptor according to the invention, as well as a DNA fragment coding for a protein of which it is desired to regulate the activity, said activity being inducible by binding of said receptor or of said ligand binding domain with a said synthetic glucocorticoid ligand, but not by binding with a natural glucocorticoid ligand when said protein is fused to said receptor or to said ligand binding domain of said receptor.

More particularly, the subject of the present invention is a fusion gene comprising, in the 5'→3' direction:

a DNA fragment coding for the Cre recobinase of bacteriophage $P_1$:

a DNA fragment coding for all or part of the hinge region D of the nuclear glucocorticoid receptor, a region situated between the DBD domain and the LBD domain, and the DNA fragment coding for the modified, in particular mutated, ligand binding domain (LBD) of the nuclear glucocorticoid receptor according to the invention.

And still more particularly, the subject of the present invention is a fusion gene, characterized in that it has, as sequence, a sequence coding for the amino acid sequence of SEQ ID NO: 2 comprising:

amino acids 1 to 343 which correspond to the Cre recombination;

amino acids 346 to 377 which correspond to the C-terminal region of the D region of the human glucocorticoid receptor;

amino acids 378 to 623 which correspond to the LBD [GR(I747/T)].

In a specific embodiment, the fusion gene has substantially, as sequence, the Cre-LBD[GR(I747/T)] sequence as represented in SEQ ID NO: 2 in which amino acids 626 to 667 correspond to the F region of the human estrogen receptor.

The subject of the present invention is also a vector for expressing the fusion protein encoded by the fusion gene according to the invention, in animal, in particular mammalian, host cells, characterized in that it comprises the fusion gene according to the invention, placed under the control of elements for expression ensuring its expression in said host cells. The vector for expressing the fusion protein may also be a vector or integrating into the genome of the host cells.

In the vectors according to the invention, to express the receptor, the LBD or the fusion protein according to the invention, it is necessary for the DNA fragments coding for these molecules to be placed under the control of a regulatory sequence, in particular of the promoter/enhancer sequences. Promoter/enhancer sequences of the $SV_{40}$ virus may be used in particular.

The subject of the present invention is, in addition, a method of recombination, in particular of conditional excision, insertion, inversion or translocation at the level of a DNA fragment containing one or two sites for specific recognition of a recombinase protein in human or animal, in particular mammalian, host cells, characterized in that it comprises the steps in which:

1) a fusion protein according to the invention or a vector for expressing said fusion protein according to the invention is introduced into said host cells under conditions allowing the expression of the fusion protein according to the invention and, 2) said fusion protein is complexed with a said synthetic glucocorticoid ligand by exposing said ligand to said host cells.

The present invention therefore provides a method for the conditional deletion of a DNA fragment in which a method of excision according to the invention is used, and in which said DNA fragment to be excised is integrated between two recombinase protein recognition sites oriented as a direct repeat. In particular, said DNA fragment may be chosen so that the excision of said DNA fragment has, as effect, the inactivation of said gene. The excision of said DNA fragment can also allow the synthesis of a functional protein if said fragment contains, for example, a stop codon or a polyadenylation signal.

In the preferred embodiment according to the invention, said recombinase protein specific recognition sites are the loxP sites and said recombinase protein is the Cre protein of bacteriophage $P_1$.

Said DNA fragment which it is desired to recombine, in particular to excise and said recognition site(s) specific for a recombinase protein may be carried by a plasmid or viral vector, or may be integrated into the chromosome of the host cells.

The integration of a gene carrying the loxP sites in a genome may be random or targeted, In particular, the integration of the recombinase protein specific recognition sites, in particular of the loxP site(s) for the Cre recombinase, may take place by homologous recombination of the gene comprising said DNA fragment to be excised or inverted (2 loxP sites) or respectively inserted or translocated (1 loxP site) with a said modified gene comprising said DNA fragment to be excised flanked in 5' and/or 3' by said recombinase recognition site(s) depending on the desired application, in particular the loxP sites.

A chimeric protein, Cre-LBD[GR(747/T)] of SID No. 2, composed of the Cre recombinase fused to the LBD of GR (I747/T) was constructed. The fusion protein Cre-LBD[GR (I747/T)] makes it possible to carry out a recombination between the loxP sites, in a mammalian cell, following a treatment with synthetic glucocorticoids. In the absence of treatment, or in the presence of concentrations of natural glucocorticoids of up to $10^{-6}$ M, no excision is observed. This chimera is capable of excising the DNA sequences situated between the loxP sites previously integrated into the genome of F9 cells (mouse embryo carcinoma) or present on a plasmid after transfection of these cells with a vector expressing Cre-LBD[GR(I747/T)] following a treatment with Dex at $10^{-6}$ M or $10^{-7}$ M, whereas at such concentrations, cortisol does not induce recombinase activity. As already stated, the Cre-LBD[GR(I747/T)] expression vector may also be a vector for integration into the aenome of the host cells.

This system therefore makes it possible to release the recombinase activity of a chimeric protein at given and chosen time. The fusion protein Cre-LTD[GR(I747/T)] may be expressed in cells containing loxP sites without modifying the locus containing the loxP sites. Recombination at the level of the loxP sites takes place only after treatment with synthetic glucocorticoids. Furthermore, by expressing the fusion protein Cre-LBD[GR(I747/T)] in an animal under the control of a promoter exhibiting cellular specificity, it is possible to obtain recombination between loxP sites, specifically in these cells.

The subject of the present invention is also a vector for transferring a DNA fragment into human or animal, in particular mammalian, host cells, characterized in that it comprises a said DNA fragment to be transferred comprising recognition sites specific for the recombinase, in particular two loxP sites, oriented as direct repeats and a cassette for expression of a fusion gene according to the invention. Appropriately, the two sites are placed at each end of said DNA fragment.

Preferably, the fusion gene is placed under the control of expression elements specific for the host cells; in particular, it comprises the sequence of the plasmid pCre-LBD[GR (I747/T)] of SEQ ID NO: 3.

In the excision method according to the invention, said DNA fragment to be excised may be transferred into the host cells before, at the same time, or after the step of introducing the fusion protein or a transfer vector.

The transfer vector according to the invention may be a plasmid or a viral vector. The mode of transfer varies according to the type of target cell and the desired efficiency.

When the material is transferred into the germ cells, microinjection of the male pronucleus of a fertilized oocyte is preferably used. To introduce the DNA into pluripotent embryonic cells (ES cells), the appropriate technique will instead be electroporation or the use of retroviral vectors.

For experiments on somatic cells, it is sought to obtain a maximum efficiency, hence the preferential use of viral vectors: mainly retroviruses and adenoviruses. These viruses should be defective, in particular for application in human health to prevent any multiplication or any risk of revertion.

After integration or otherwise of this type of vectors into the genome, the Cre-lox system makes it possible to excise certain viral sequences which might possibly present a risk in relation to the subsequent propagation of the virus. This is very advantageous for the use of such vectors in gene therapy. Vectors containing a cassette for expression of the Cre-LBD[GR(I747/T)] gene and lox sites delimiting a potentially "dangerous" gene and this cassette make it possible, where appropriate after integration into the genome of the recombinant virus, to eliminate these elements. Conversely, it is also possible to activate a gene which has been integrated in an inactive form. This activation may result from the deletion of a fragment from said gene, for example a stop codon or a polyadenylation signal delimited by loxP sites.

When it is desired to transfer genetic material into a cell, constructs are generally used which comprise the gene to be transferred, to which a helper gene has optionally been added, conferring a selective advantage (for example the neo gene conferring resistance to the antibiotic G418).

Selectable markers may also be excised by the excision method according to the invention.

By using conventional techniques, it is possible to modify, by homologous recombination, mammalian, in particular mouse, genes. A loxP site may be introduced into a gene which it is desired to modify, or two loxP sites may delimit sequences which it is desired to modify. In particular, the selectable marker used to make it possible to identify the homologous recombination events may be problematic, and may be removed in a first instance, if necessary, if it is itself delimited by recombinase recognition sites such as loxP or FRT sites, by microinjecting the corresponding recombinase protein, by transfecting the cells, in particular ES cells, with an expression vector for a recombinase protein, or by crossing mice carrying the selectable marker with mice expressing the desired recombinase, in particular the Cre recombinase. This makes it possible to obtain mice whose sole modification in the modified locus is the insertion of recognition sites such as loxP. These mice may subsequently be crossed with mice expressing Cre-LBD[GR(I747/T)] and the modification of the locus obtained by treatment with the ligand such as Dex. This makes it possible to inactivate or modify a gene at a given time, and therefore to study the function of these genes at various times of development. This is particularly advantageous for studying the genes which are essential for the good progress of embryonic development. Indeed, in some cases, conventional homologous recombination techniques cause the death of the embryo and do not allow the function of the gene to be studied at later stages.

The transfer of genes into a given cell forms the basis of gene therapy. The most efficient vectors in this regard are viral vectors, in particular retroviral or adenoviral vectors (39). The subject of the present invention is therefore also a transfer vector according to the invention comprising said DNA fragment to be transferred comprising two loxP sites oriented as a direct repeat, for use as a medicament in gene therapy, when it is administered in combination with a said synthetic glucocorticoid ligand such as dexamethasone.

This type of vector makes it possible to transfer the desired DNA fragment comprising two recombinase specific recognition sites into a gene so that it will be possible for the DNA sequences situated between the two loxP sites to be conditionally excised after administration of said synthetic glucocorticoid The present invention provides, if addition, human or animal, in particular mammalian, cells transfected with a vector for expression and transfer of a fusion protein according to the invention, or human or animal, in particular mammalian, cells into which a DNA fragment has been transferred with the aid of a transfer vector according to the invention, or alternatively human or animal, in particular mammalian, cells constitutively expressing the fusion protein according to the invention.

A further subject of the present invention is finally a transgenic animal, in particular a mouse, comprising a functional gene for the fusion protein according to the invention, said gene being in particular integrated into one of its chromosomes.

Alternatively, a transgenic animal comprising a functional gene for the fusion protein according to the invention, in which a gene of interest is modified by insertion of loxP site(s), in particular integrated into one or more chromosomes.

The subject of the present invention is finally the use of an expression or transfer vector of cells or of an animal according to the invention as a tool for analyzing or studying the function of a given gene of a host cell and a method of treating cells ex vivo or in vitro involving the use of a method of excision, insertion, inversion or translocation according to the invention and the use of an expression or transfer vector according to the invention.

Other characteristics and advantages of the present invention will emerge in the light of the detailed description which follows.

BRIEF DESCRIPTION OF THE DRAWINGS

SEQ ID NO: 1 represents the nucleotide and peptide sequences of GR (I747/T) with the DBD corresponding to aa 421–487 and the LBD corresponding to aa 532–777;

SEQ ID NO: 2 represents the nucleotide and peptide sequences of Cre-LBD[GR(I747/T)].

Nucleotides 1–1029 code for the Cre recombinase (aa 1–343).

Nucleotides 1036–1131 code for the C-terminal region of the D region or the human glucocorticoid receptor [aa 500–531 of GR (I747/T); aa 346–377 of Cre-LBD[GR(I747/T)].

Nucleotides 1132–1869 code for the LBD of GR (I747/T) [aa 532–777 of GR (I747/T); aa 378–623 of Cre-LBD[GR (I747/T)].

Nucleotides 1876–2001 code for the F region of the human estrogen receptor [aa 554–595 of HEGO; aa 626–667 of Cre-LBD[GR(I747/T)].

Nucleotides 1777–1779 correspond to the mutation which replaces isoleucine with a threonine.

SEQ ID NO: 3 represents the nucleotide sequence of the plasmid pCre-LBD[GR(I747/T)].

SEQ ID NOS: 4 to 17 represent the nucleotide sequences of the various oligonucleotides used according to the invention.

FIG. 1 [SEQ ID NOS.: 20–21] is a schematic representation of Cre recombinase activities.

Figure 2:
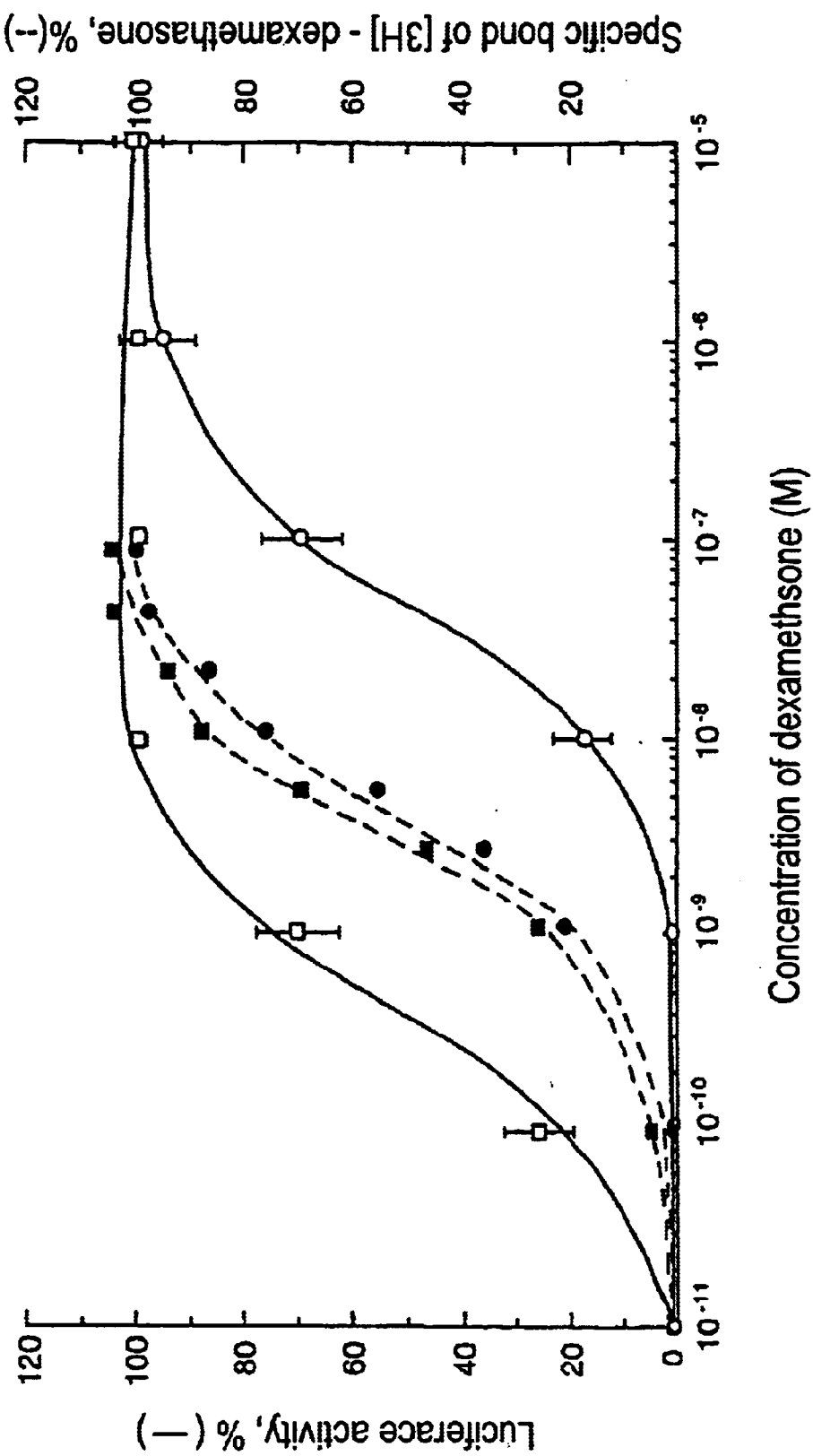

FIG. 2 represents the transcriptional activity of the mutant and wild-type GR receptor in response to dexamethasone and the capacity for attachment of dexamethasone to the two receptors.

Figure 3:
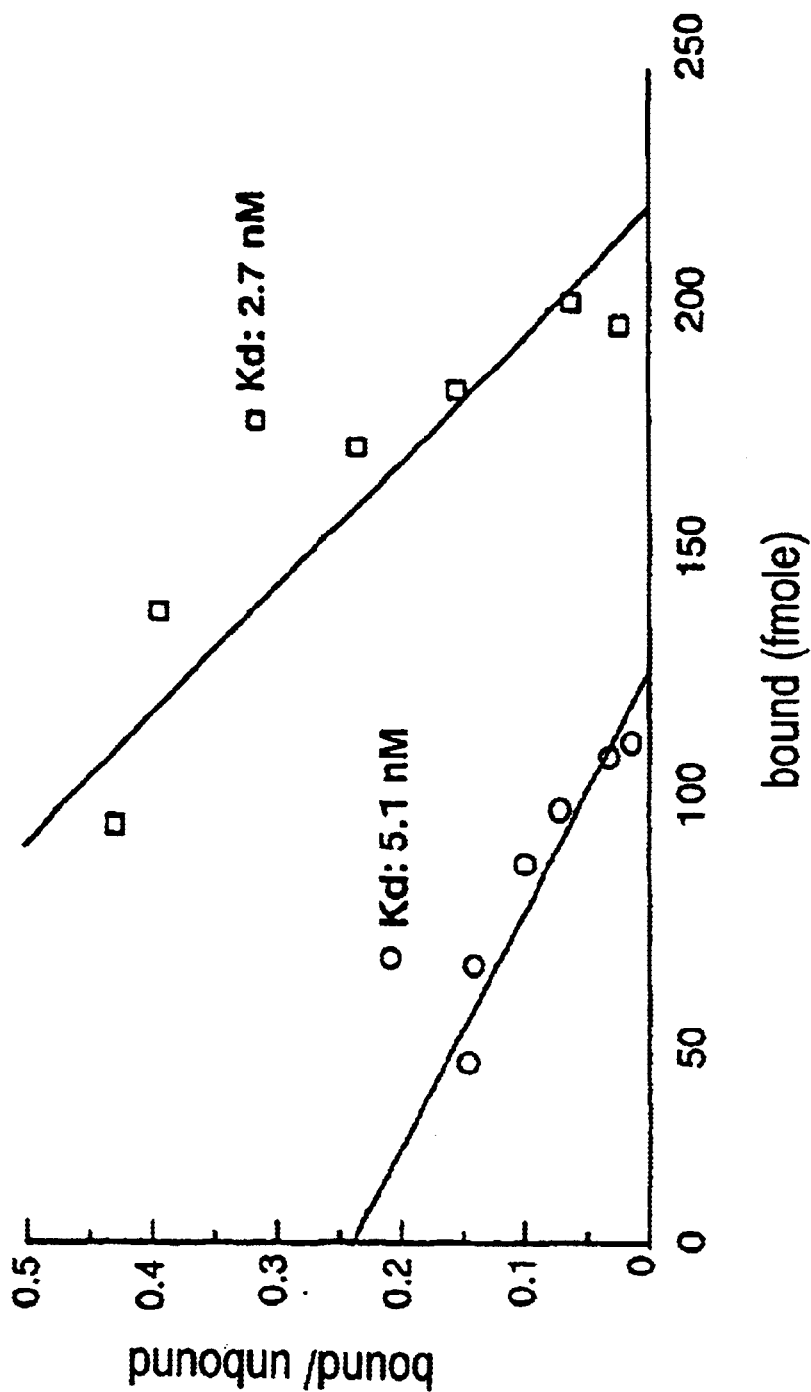

FIG. 3 represents a Scatchard analysis of the binding of [$^3$H]-dexamethasone to the wild-type and I747/T mutant receptors.

Figure 4:
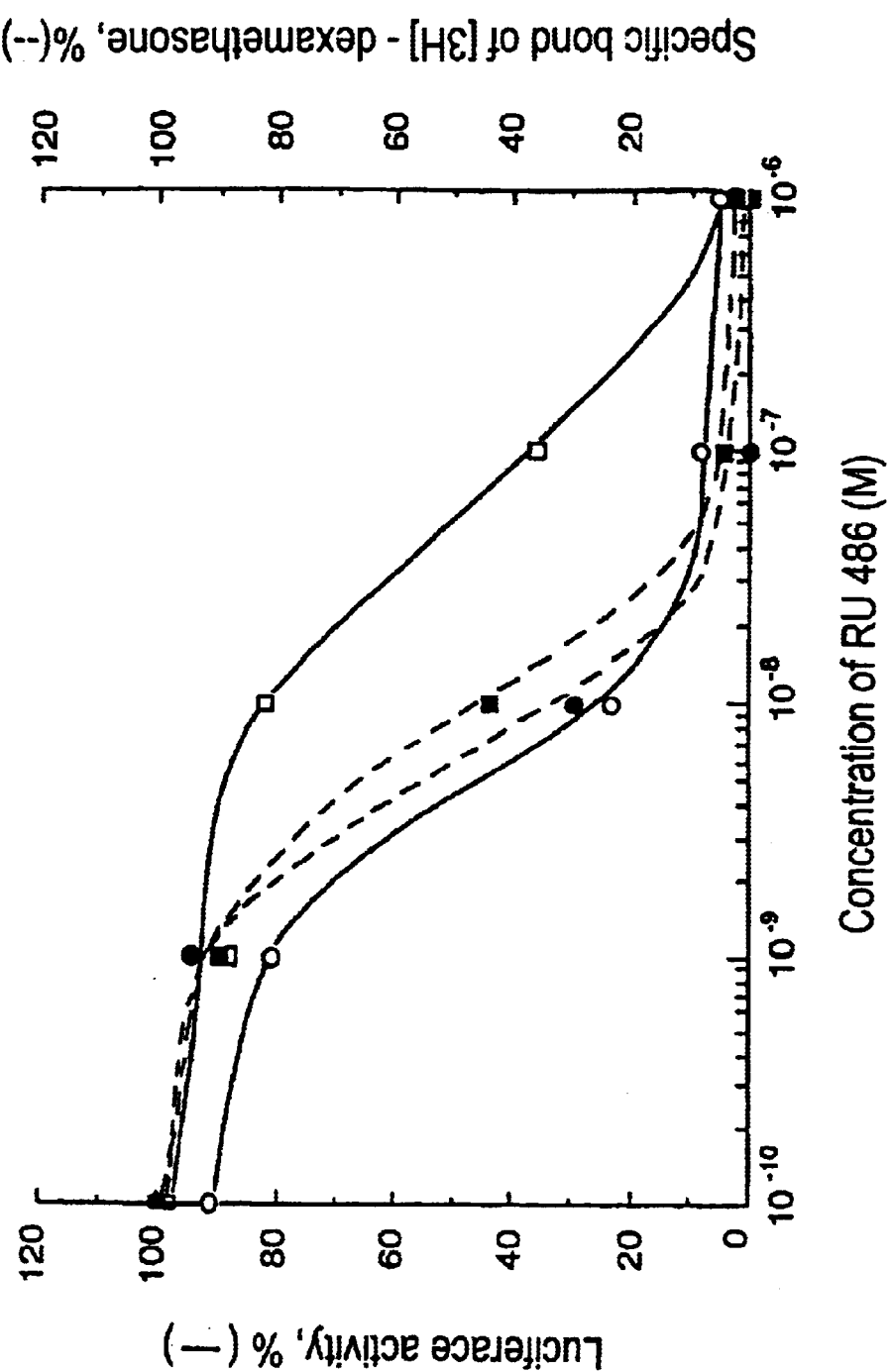

FIG. 4 represents competition by RU 486 for the Dex binding and the transactivation activities of the wild-type (WT) and GR (I747/T) receptor.

Figure 5:
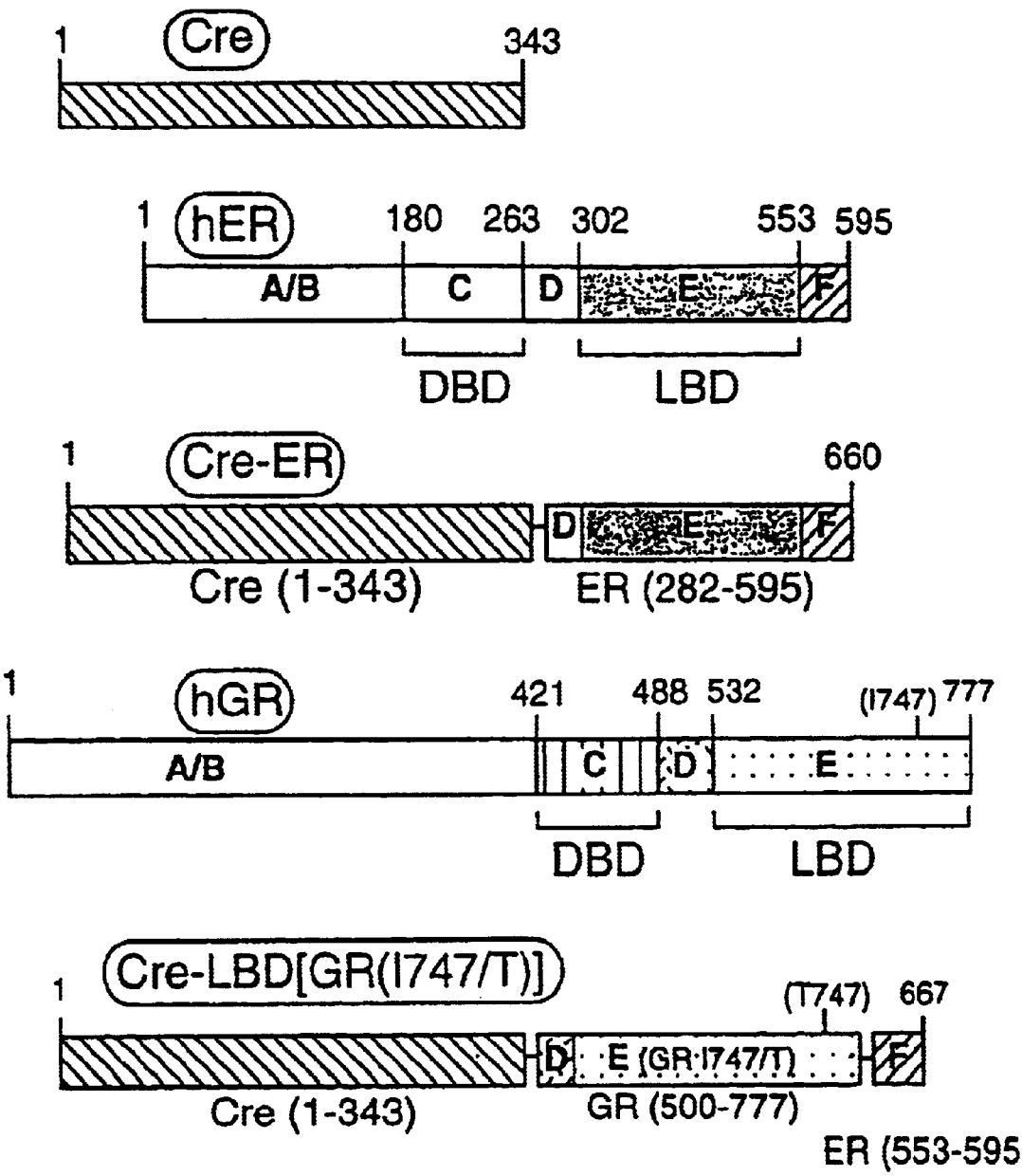

FIG. 5 is a schematic representation of the Cre, hER, Cre-ER, hGR and Cre-LBD[GR(I747/T)] proteins.

Figure 6:
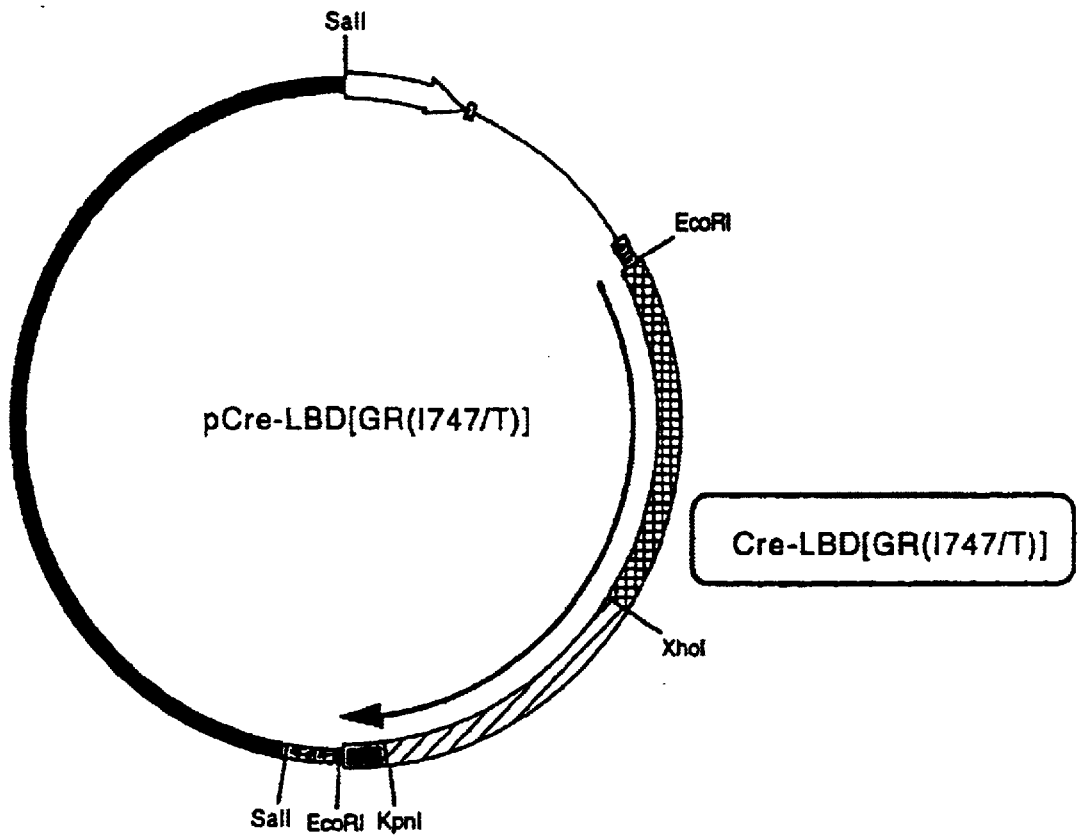

FIG. 6 is a schematic representation of the plasmid pCre-LBD[GR(!747/T)].

FIGS. 7A–D represents the nucleotide sequence of pCre-LBD[GF(I747/T)](SEQ ID NO: 5) and the peptide sequence of Cre-LBD[GF(I747/T)] (SEQ ID NO. 5.

Figure 8:
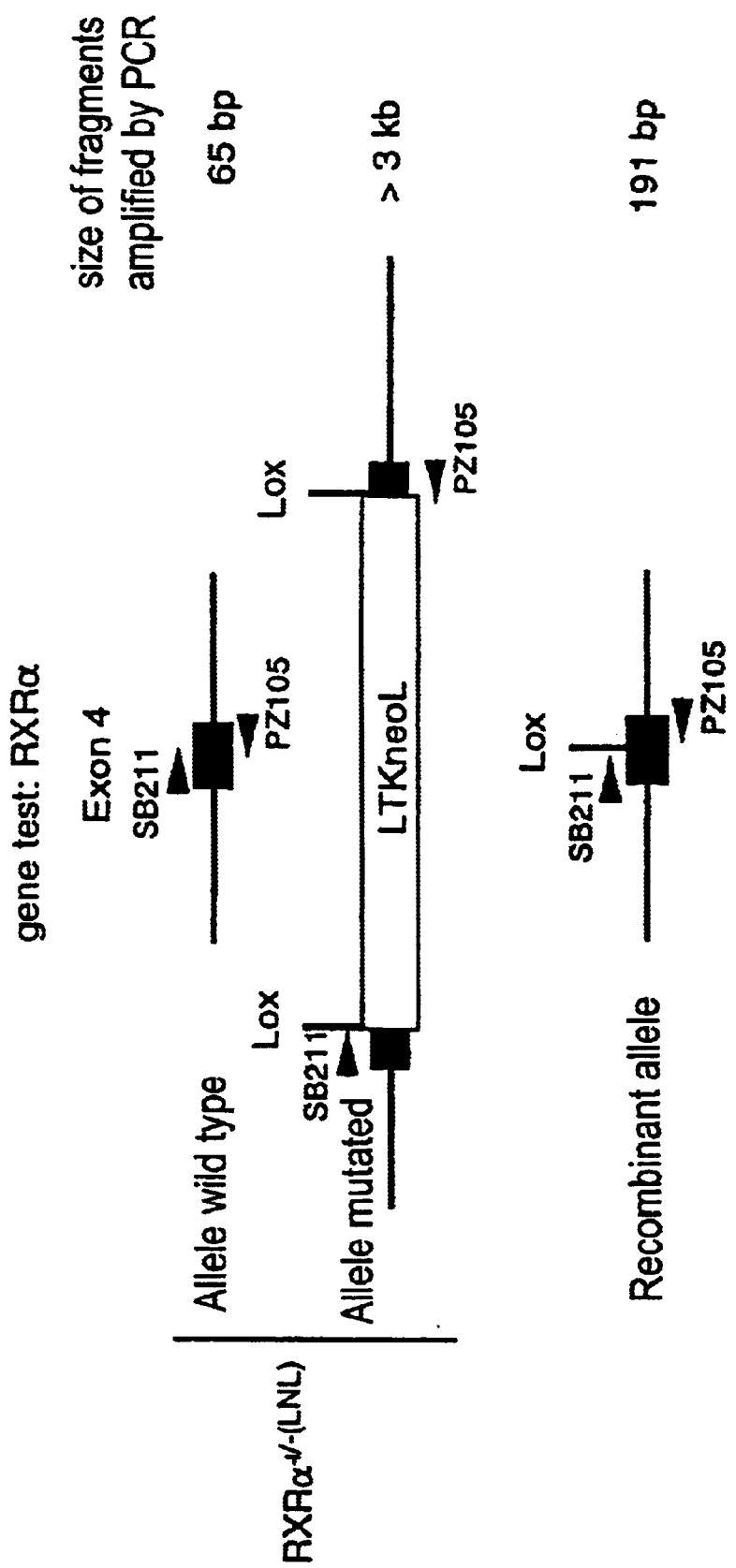

FIG. 8 represents the PCR strategy used to detect the wild-type, mutated and recombinant alleles in the test for recombinase activity of Cre-LBD[GR(I747/T)].

Figure 9:
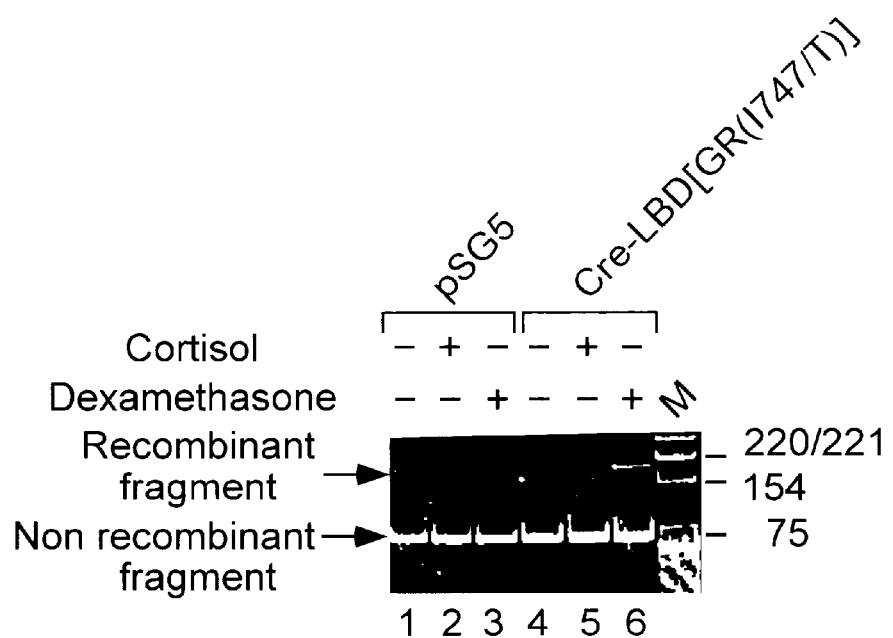

FIG. 9 represents the PCR analysis of the excision of the sequences situated between the loxP sites after transient transfection of pCre-LBD[GR(I747/T)] in the murine cells RXRα$^{+/-(LNL)}$ without addition of ligand, or treated with cortisol ($10^{-6}$ M) or with dexamethasone ($10^{-6}$ M).

Figure 10:
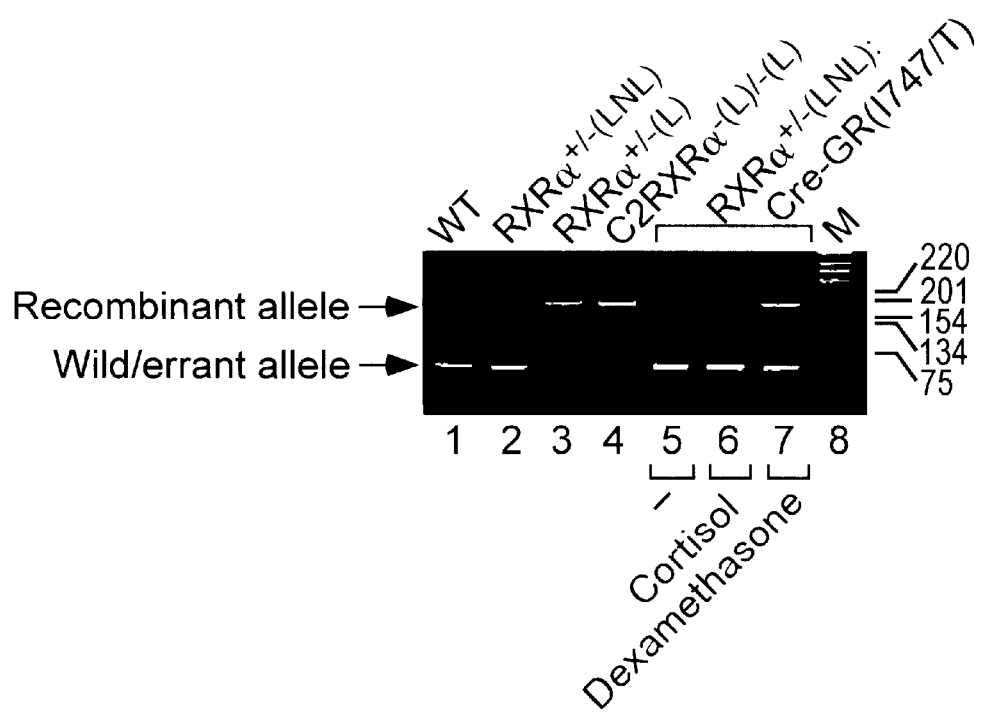

FIG. 10 represents the PCR analysis of the recombinase activity of Cre-GR(I747/T) in the cells RXRα$^{+/-(LNL)}$:Cre-GR(I747/T) not treated or treated with cortisol or dexamethasone at $10^{-6}$ M.

Figure 11:
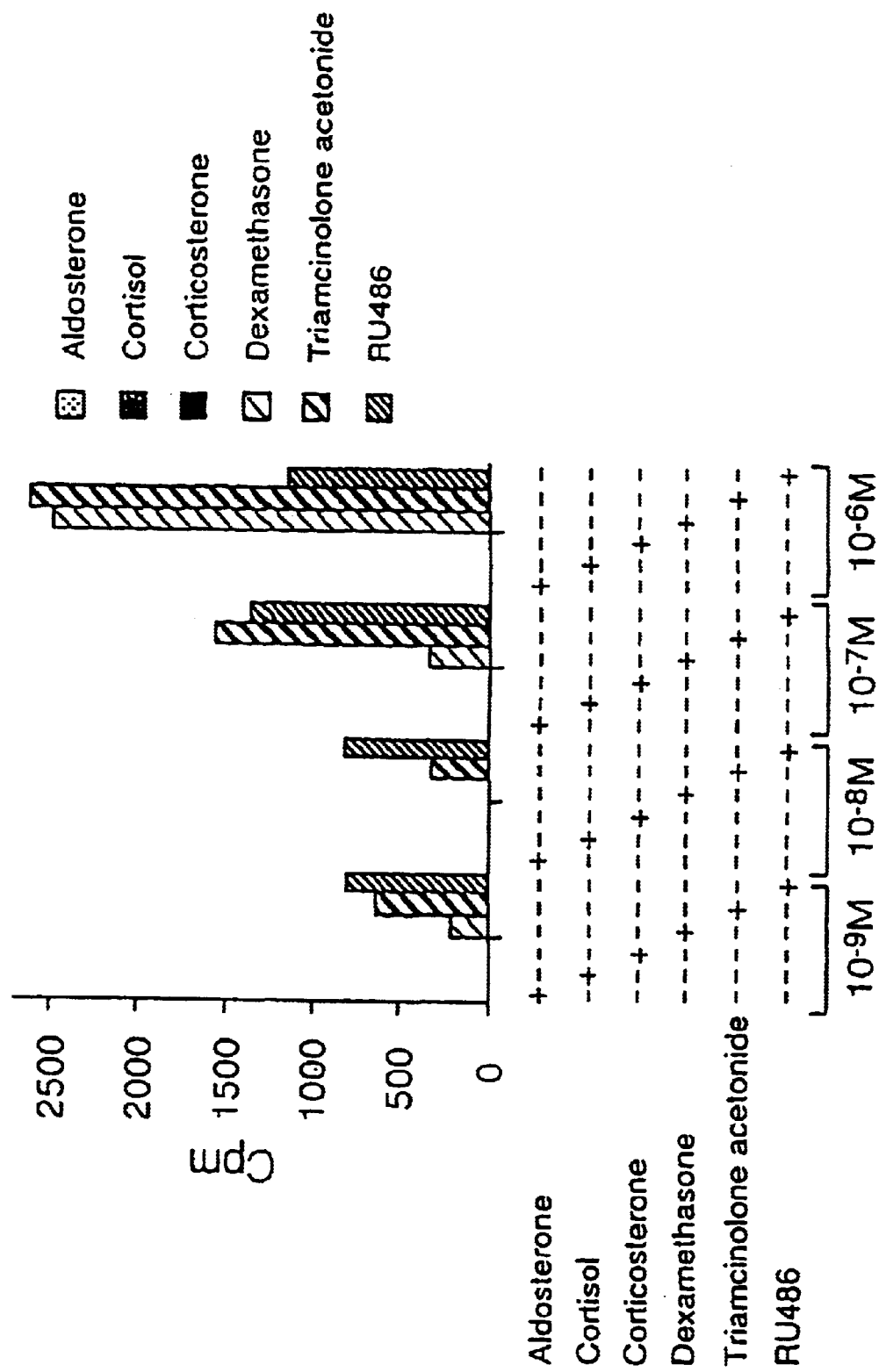

FIG. 11 summarizes the recombinase activity of Cre-LBD [GR(I747/T)] in the RXRα$^{+/-(LNL)}$ line constitutively expressing the recombinase, in the presence of increasing concentrations of various ligands.

Figure 12:
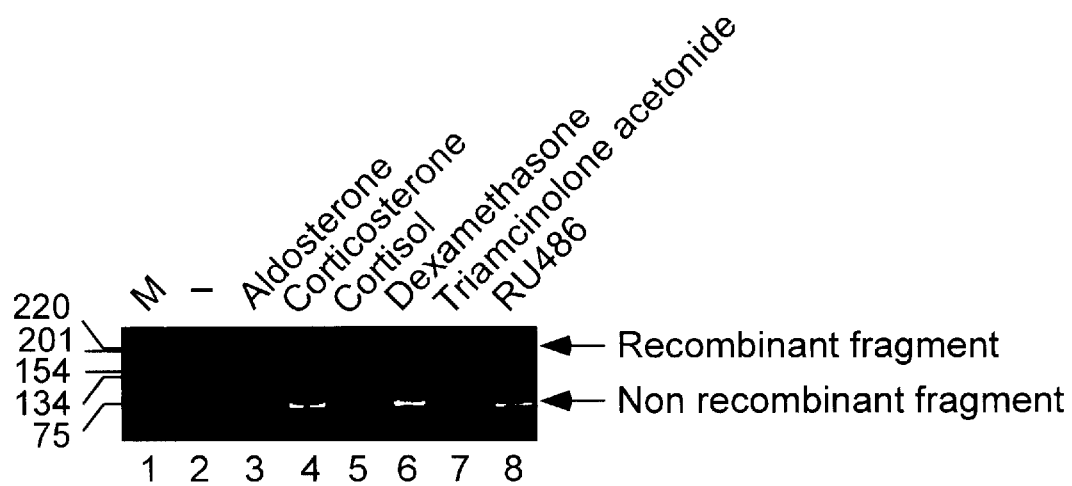

FIG. 12 represents the PCR analysis of the recombinase activity of Cre-LBD[GR(I747/T)] induced by synthetic ligands in spite of the presence of natural ligands.

Figure 13:
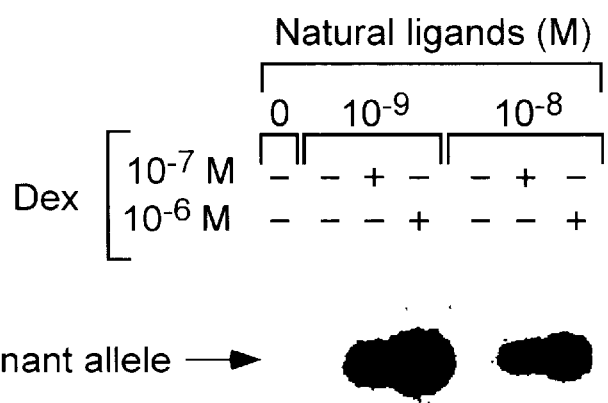

FIG. 13 represents the test for the recombinase activity of Cre-LBD[GR(I747/T)] in human HeLa cells.

FIG. 14 is a schematic representation of the trangene Cre-LBD[GR(I747/T)]. Part (a) represents the DNA fragment containing the sequence coding for the Cre-LBD[GR (I747/T) ] gene used to establish transgenic mice and part (b) represents the genomic structure of the wild-type allele RXRα, of the target allele RXRα$^{ΔΔF1\ (LNL)}$ and of the excised allele RXRα$^{ΔΔF1\ (L)}$ as well as the PCR strategy for analyzing the excision of the marker.

Figure 15:
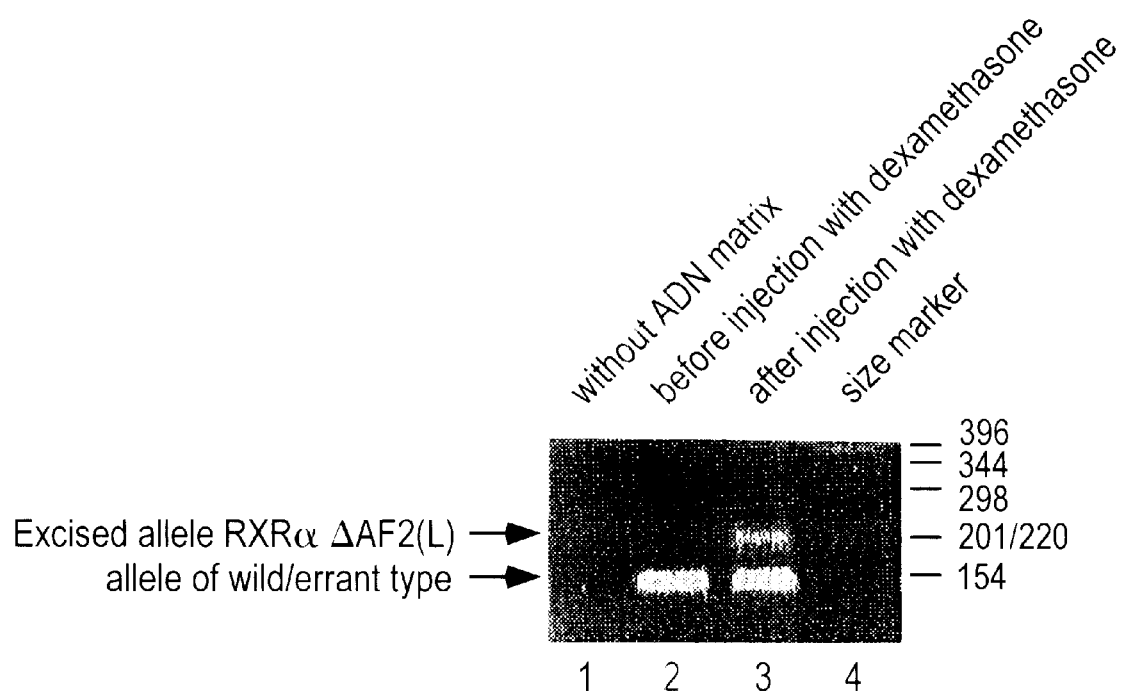

FIG. 15 represents the PCR analysis of the recombinase activity of Cre-LBD[GR(I747/T)] in mice treated with dexamethasone.

DETAILED DESCRIPTION OF THE INVENTION

EXAMPLE 1

Replacement of isoleucine 747 with threonine in the human nuclear glucocorticoid receptor.

A human GR mutant was obtained comprising a single amino acid replacement, that of the isoleucine 747 residue by a threonine residue, located between helices H11 and H12, in the C-terminal part of the ligand binding domain. This mutation appeared spontaneously in the vectors derived from HG1 (40). This mutant is different from other GR LBD mutants previously described (22, 38), in which the altered activation function is closely correlated with a modification in their ligand binding properties in vitro.

1. Mutation in the Human GR

The vector for expression of the wild-type human GR (pSG5HG0) was obtained by cloning the BamHI fragment of about 2.9 kb (containing the open reading frame of the wild-type hGR) isolated from the HG0 vector previously described (40), into the BamHI site of the expression vector pSG5 (41).

All the DNA constructions were performed by means of conventional techniques (42). The expression vector GR (I747/T)hGR, coding for a mutant carrying the I 747→T mutation, was obtained from the fragment of PstI-PflMI digestion of the mutated expression vector HG1 (40) which was ligated into the corresponding PstI and PflMI sites of pSG5HG0.

In addition to the isoleucine 747 residue to a threonine residue mutation present in HG1, this mutant also contains a mutation of the EcoRI site which does not result in any alteration of the peptide sequence.

The presence of the mutation was confirmed by sequencing (Sequenase 2.0 protocol, U.S. Biochemical Corp., Cleveland, Ohio).

2. Results 2.1. The Replacement of Isoleucine 747 by Threonine Leads to Shift in the Dexamethasone Dose-response Curve for Transactivation, Without Substantially Affecting the Ligand Binding Affinity.

The transcriptional characteristics of the wild-type (WT) hGR and of a mutant in which isoleucine 747 was replaced by threonine [designated hereinafter GR (I747/T)] were compared. The receptors were transiently expressed in GR-free CV-1 cells, conjointly with a luciferase reporter gene under the control of the tyrosine aminotransferase promoter (pTAT-tk-Luc). FIG. 2 shows the corresponding curves of response as a function of ligand dose used, allowing the EC$_{50}$ (ligand concentration giving 50% of the maximum transcriptional response) values to be determined. The dose-response curve for WT hGR exhibits a maximum response at $10^{-8}$ M Dex and a response equal to half the maximum response at $4\times10^{-8}$ M, whereas the transcriptional response curve for the GR (I747/T) mutant is markedly shifted toward the highest ligand concentrations, resulting in 100-fold higher values of the EC$_{50}$ for Dex ($4\times10^{-8}$ M) (see Table I below). The maximum stimulation mediated by GR (I747/T) was reached at about $10^{-6}$ M Dex. However, it is important to note that the GR (I747/T) receptor is capable of activating the transcription of pTAT-tk-Luc to the same degree as the WT GR. Consequently, the replacement of the isoleucine residue by threonine at position 747 does not reduce the ability of GR to activate transcription but specifically modified the ligand sensitivity of the response.

The effect of this mutation is independent of the N-terminal A/B region and of its associated transactivation function AF-1. The deletion mutants lacking AF-1 but containing the I747/T[ΔA/B-GR (I747/T)] mutation require $3\times10^{-8}$ M Dex for a stimulation representing half the maximum stimulation, whereas only $6\times10^{-10}$ M are sufficient for the ΔA/B-GR derived from the WT (data not represented; see also Table II for the corresponding GAL chimeras). Thus, the I747/T mutation exerts a similar effect on the complete GCr and the CR with N-terminal deletion. It can be concluded therefrom that the shift observed in the response as a function of the ligand and dose is not the consequence of modified interaction between AF-1 land AF-2.

To determine the effect of the I747/T mutation on the binding of the ligand, the binding of Dex was measured in a cytosol of Cos-7 cells transiently expressing the mutant hGR and the wild-type hGR. The $K_d$ values obtained from a Scatchard analysis are very similar since the I747/T mutant only manifests an affinity for Dex which is twice as low as the WT GR (FIG. 3). Thus, the order of magnitude of the shift in the dose-response curves toward the high concentrations of hGR (I747/T), compared with the WT hGR (about 100 fold) is not very likely to result from a decrease in affinity for the ligand for the mutated hGR (factor of 2 only; compare FIGS. 2 and 3).

2.2. hGR (I747/T) Does Not Respond to the Natural Ligands

To further characterize the binding characteristics of the I747/T mutant, the activation by various known synthetic agonists for the WT GR (triamcinolone acetonide, RU28362, bimedrazol), a partial agonist (fluocinolone acetonide) and natural glucocorticoids (cortisol, corticosterone), was compared. With the mutant receptor, triamcinolone acetonide and RU28362 give the same transactivation as with the wild-type receptor, whereas bimedrazol and fluocinolone acetonide manifested a higher activity (Table I). For all these analogs, the I747/T mutant manifests a shift in the dose-response curve in the direction of the higher ligand concentrations, although this shift is less pronounced for high affinity ligands (Table 1).

Natural ligands, such as cortisol or corticosterone or aldosterone, the natural ligand for the mineralocorticoid receptor, bind to GR with a lower affinity than Dex. With the wild-type GR, these ligands are as effective as Dex for stimulating the luciferase reporter (Table I). However, in the presence of these natural ligands, and in notable contrast with the effects observed with Dex, transactivation by the I747/T mutant is greatly reduced (cotisol) or suppressed (corticosterone, aldosterone).

2.3. Similar Agonist and Antagonist Activities of RU486 With Wild-type hGR and Mutant hGR RU486 is a potent inhibitor of the expression of genes which are dependent on glucocorticoids. In the presence of this antagonist, the AF-2 function of GR is blocked, but it has been possible to observe some AF-1-dependent agonist activity [(43) and references contained therein]. A mutation or a deletion of the C-terminal part of the LBD can alter the response to agonist/antagonist ligands, although the roles of AF-1 and AF-2 have not been clearly defined in the studies reported (44–46).

To test the relative binding affinity of RU486 for the I747/T mutant and the wild-type, the ability of RU486 to enter into competition with Dex for binding to the receptors was examined. Cells transfected with mutant or WT hGR were treated with 10 nM [$^3$H]-Dex, a concentration sufficient to generate essentially mutant and WT receptors complexed with Dex, in conformity with the in vitro ligand binding tests (see above), and with increasing concentrations of RU486 (FIG. 4). Very similar $IC_{50}$ (the antagonist concentration blocking 50% of the maximum transactivation) values were obtained for the two receptors ($10^{-8}$ M for the WT hGR and $6\times10^{-9}$M for the mutant hGR). These results are in agreement with the tests for binding to Dex and show that the affinities for binding to Dex and RU486 are not modified by the I747/T mutation.

2.4. The Shift in the Transcriptional Activity of the Mutant Receptor is Independent of the Promoter The results described above were obtained in transfected cells using a reporter gene containing a promoter fragment of the TAT gene which harbors two glucocorticoid response elements (GRE). To distinguish between a modification of the intrinsic transactivation properties of the receptor and modification of the cooperative activity resulting from the binding of several receptor molecules, the transcriptional activities of the mutant receptor GR (I747/T) and of the wild-type receptor were compared using a synthetic promoter containing a single GRE, which is palindromic and perfect. The corresponding dose-response curves have the same profiles as those obtained with the TAT promoter. The response corresponding to half the maximum response is obtained at $10^{-10}$ M for the WT GR and at $2\times10^{-8}$ M for GR (I747/T) (Table II). This indicates that the shift observed with the mutant receptor reflects the intrinsic transactivation properties of the mutant GR (I747/T) and are not the result of an alteration in the cooperation between the receptors.

The replacement of the DNA binding domain of GR by the first 147 amino acids of the yeast Gal4 transactivator gives a hybrid activator protein having a new promoter specificity. The Gal4-GR hybrids consist of the DNA binding domain (DBD) of Gal4(1–147) fused with the LBD of WT or mutant hGR. Their capacities to activate transcription were tested in transient transfection tests in HeLa cells. The same shift was observed as with the complete GR (I747/T) mutant (Table II). These results show that the shift in the transcriptional response as a function of the ligand dose is independent of promoter and of response element (RE). In addition, this effect is apparently not specific for the strains of cells used, as has been observed both in human HeLa cells and in simian Cos cells. To further exclude a possible involvement of factors binding to the tk or β-globin promoter of the reporter gene (47), a reporter gene was used containing a Gal4 response element preceding a minimal promoter. Although transactivation by the Gal4 chimeric protein was reduced with this minimal reporter gene, it was still possible to observe a shift in the response curve toward the increasing doses for the mutant chimeric protein Gal4-GR (I747/T) (Table II).

2.5. Transcriptional Activity of Mutant and Wild-type GR Receptors in Response to Dexamethasone (FIG. 2).

CV-1 cells were transiently transfected with 0.5 μg of vectors for expression of wild-type GR (□) or of GR (I747/T) (o), 2.5 μg of pTAT-tk-Luc as reporter plasmid and 0.5 μg of pCMV-βGal as internal control. After transfection, the cells were incubated for 24 hours with increasing concentrations of Dex, and they were then subjected to an assay of the β-galactosidase and luciferase activities, as described in "Materials and Methods". The luciferase activity was normalized with the β-galactosidase activity, and the value obtained in the absence of ligand was subtracted for each point. The results were expressed as a percentage of the maximum luciferase activity obtained for each receptor. Each point is the mean±standard deviation of the mean of four separate determinations carried out in duplicate. The analyses of binding at saturation were carried out on cytosols obtained from Cos-7 cells transfected with 40 μg of vector for expression of wild-type hGR (□) or of hGR (I747/T) (•), with 20 μg of pCMV-βGal incubated overnight at 4° C. in the presence of increasing concentrations of [$^3$H]-dexamethasone±a 100× excess of radio-inert Dex. The [$^3$H] steroid attached was measured after treatment with dextran-coated charcoal. The results presented are those for a single assay carried out in duplicate and representative of three separate assays. The saturation curves for the binding of [$^3$H]-dexamethasone are represented as a percentage of the maximum binding capacity obtained for each receptor. The binding capacity of the GR (I747/T) mutant is reduced to reach about 40–60% of that of the wild-type hGR (623±65 fmol/mg of protein, compared with 1340±285 fmol/mg of protein).

2.6. Scatchard Analysis of the Binding of [$^3$H-dexamethasone to the Wild-type and I747/T Mutant Receptors (FIG. 3).

The Scatchard analysis was applied to the binding performed as described in FIG. 2. The apparent dissociation constant for the GR (T747/T) mutant (o) is only twice as high as that for the wild-type hGR (υ) ($K_o$=5.1±1.9 compared with 2.7±1.3 nM).

TABLE I 2.7.
Transcriptional activities and $EC_{50}$ of various steroids with wild-type hGR and hGR(I747/T)

| Ligand | Luciferase activity % | | EC50 | | |
|---|---|---|---|---|---|
| | Wild type | hGR (I747/T) | Wild type | hGR (I747/T) | % $EC_{50}$ |
| Dexamethasone | 100 | 100 | $4 \times 10^{-10}$M | $4 \times 10^{-8}$M | 100 |
| TA | 98 | 102 | $5 \times 10^{-10}$M | $2 \times 10^{-8}$M | 40 |
| RU28362 | 90 | 88 | $3 \times 10^{-10}$M | $7 \times 10^{-9}$M | 23 |
| Fluocinolone | 75 | 100 | $1.5 \times 10^{-10}$M | $3 \times 10^{-9}$M | 20 |
| Bimedrazol | 100 | 180 | $10^{-10}$M | $2 \times 10^{-9}$M | 20 |
| Cortisol | 110 | 15 | $7 \times 10^{-9}$M | nm | |
| Corticosterone | 100 | 0 | $7 \times 10^{-8}$M | nm | |
| Aldosterone | 90 | 0 | $5 \times 10^{-8}$M | nm | |

Co-transfections were carried out and dose-response curves were constructed as described in FIG. 2. Six increasing concentrations were tested, in duplicate, triamcinolone acetonide (TA), RU28362, fluocinolone acetonide (fluocinolone), cortisol, corticosterone and aldosterone. The assays of luciferase and β-galactosidase activity were carried out as described in "Materials and Methods". The mean values of three independent assays are given in this table. nm=not measurable.

2.8. Competition for the Dex Binding and for the Transactivation Activities by RU486 (FIG. 4).

Cos-7 cells transfected with the wild-type hGR (□) or I747T mutant (e) were incubated for 1 hour at 37° C. with 10 nM [3H]-dexamethasone alone or in the presence of the indicated concentration of nonlabeled RU486, as descibed in "Materials and Methods". The data are expressed as a percentage of the specific binding observed the control not subjected to the competition. These data represent the mean of determinations carried out in duplicate for each antagonist concentration.

The antagonist activity was determined on CV-1 cells transfected as described in FIG. 4 and treated simultaneously with $10^{-7}$ M Dex and the indicated concentration of RU486, 24 hours before harvesting for the assay of the luciferase and β-galactosidase activities. 100% activity is defined for each receptor as the luciferase activity of the cells treated with Dex alone. Each point represents the mean of at least two independent tests carried out in duplicate. (□) wild-type hGR; (o): I747T mutant.

TABLE II 2.9.
$EC_{50}$ obtained with various reporter genes

| Receptor | Reporter gene | $EC_{50}$ |
|---|---|---|
| Wild-type GR | PGRE-tk-Luc | $10^{-10}$M |
| GR(I747/T) | " | $2 \times 10^{-8}$M |
| Gal4-GR | p(17M)$_5$-βGlob-Luc | $1.7 \times 10^{-9}$M |
| Gal4-GR$_{(I747/T)}$ | " | $1.5 \times 10^{-7}$M |
| Gal4-GR | p(17M)$_5$-tata-Luc | $2 \times 10^{-9}$M |
| Gal4-GR$_{(I747/T)}$ | " | $2 \times 10^{-7}$M |

HeLa cells (for the Gall chimeras) or CV-1 cells were transiently cotransfected with various expression vectors and reporter genes. The transfection efficiency was standardized by cotransfecting with 0.5 μg of vector pCMV-βgal. The cells were treated for 24 hours with increasing concentrations of dexamethasone. The luciferase and β-galactosidase assays were carried out as described in "Materials and Methods". The luciferase activity is expressed as a percentage of the maximum activity obtained for each receptor and each reporter gene. The $EC_{50}$ values were determined graphically.

2.10. Outline

The isoleucine 747 mutation of the human glucocorticoid receptor to threonine results in a very high reduction, or even in an abolition, of the transactivation activity of the receptor, in the presence of natural glucocorticoids, whereas at similar concentrations, synthetic glucocorticoids efficiently stimulate the transactivation activity of this mutated receptor.

It is important to underline that hGR (I747/T) responds fully to a high concentration of Dex, which indicates that it can, in principle, transactivate as efficiently as its wild-type counterpart. Consequently, the transcriptional activation function of AF-2 itself is apparently not altered by the mutation, as is the case for receptors comprising mutations in the core part of AF-2 (see the introduction for the references).

3. Materials and Methods 3.1. Cell Cultures and Transfection

The CV-1 and Cos-7 cells were cultured in Dulbeco's modified Eagle's medium (DMEM) containing 10% (v/v) of fetal calf serum (FCS) (Gibco, Grand Island, N.Y.), in a humidified atmosphere containing 5% $CO_2$. The HeLa cells were cultured under the same conditions. Transient transfections were carried out in 6-well multiplates according to the calcium phosphate procedure already described (42). A reference recombinant plasmid, pCMV-βgal, expressing bacterial β-galactosidase, was transfected conjointly with the receptor expression vector and the corresponding reporter gene so as to correct possible variations in he transfection efficiency. The precipitate was removed by washing after 24 hours, and the cells were kept in DMEX without FCS but containing hormone. After another 24 hours, the cells were rinsed and lysed for 15 minutes with 0.3 ml of lysis buffer [25 mM Tris.phosphate, pH 7.8, 8 mM $MgCl_1$, 1% Triton X100, 10% glycerol (48)]. The corresponding luciferase activity as determined on an aliquot fraction (0.1 ml), by evaluation of the luminescence peak (for an integration time of 15 seconds), after injection of 0.1 ml of 1 mM luciferin in an LKB luminometer. The β-galactosidase was determined by the method modified by Bocquel et al. (49), for controlling the efficiency of each transfection.

3.2. Plasmids Used

The N-terminal deletion GRs, ΔA/B-GR or ΔA/B-GR5I747/T), which expressed only amino acids 368 to 777, were obtained from the fragment of PstI-Pfl MI digestion of the expression vector HG0 or pGR (I747/T), respectively, ligated into the corresponding sites of HG8 (49). The plasmid pGAL-GR (gift from T. Lerouge) consisted of the DNA binding domain of the yeast Gal4 protein (aa1–147) and of the hormone binding domain of GR (a500–777); pGal-GR (I747/T) was constructed by insertion of the mutation into pGal-GR.

The reporter gene pTAT-tk-Luc was provided by D. Gagne and was constructed as follows: an intermediate plasmid pTAT was first generated by insertion of the 966 bp EcoRI-BamHI segment obtained from pKT531 [offered freely by T. Grande (50)] into the corresponding sites of the vector pUC19 (Pharmacia). The fragment containing the sequence coding for the firefly luciferase and the thymidine kinase (tk) minimal promoter obtained from the Herpes simplex virus was isolated in the form of a BamHI fragment from pvit-tk-Luc (51) and inserted, downstream of the TAT promoter, into the corresponding site of pTAT. The reporter plasmid pGRE-tk-Luc was constructed by ligation of the fragment of HindIII-BglII digestion of pGRE-tk-CAT (52), which contains a synthetic GRE (AGAACAcagTGTTCT) upstream of the tk minimal promoter, into the HindIII-BglII sites of pLuc (53). The reporter gene $p(17M)_5$-βGlob-Luc has been previously described (54). The reporter plasmid $p(17M)_5$-tata-Luc was constructed from the plasmid $p(17M)_5$-tata-CAT (55) by digestion with XhoI-BamHI and isolation of the fragment containing $(17M_5)$-tata. This fragment was then inserted into the vector $pGL_2$ (Promega) digested with the same restriction enzymes.

The β-galactosidase expression vector pCMV-βgal contains the sequence coding for β-galactosidase, under the control of the strong constitutive cytomegalovirus (CMV) promoter.

3.3. Test of Binding to a Hormone

Cos-7 cells transfected with pCMV-βgal and wild-type hGR or I747/T mutant were harvested 48 hours after the transfection, in a phosphate-buffered salt solution (STP), by scraping with the aid of a rubber spatula. The cells were washed twice in ice-cold STP. All the steps for the preparation of cytosols were carried out at 4° C. The cells were resuspended in 3 volumes of binding buffer (20 mM Na-HEPES, pH 7.3, 20 mM sodium molybdate and 5 mM EDTA (22)] and with protease inhibitors [leucopeptin (5 µg/ml), aprotinin (5 µg/ml), PMSF (40 µg/ml) and pepstatin A (5 µg/ml)], and they were placed for 15 minutes on ice. The cells were then lysed by 30–40 piston strokes in a Dounce glass homogenizer, and the resulting homogenate was then centrifuged at 110,000 g for 30 minutes. The supernatant, called cytosol, was used immediately for the test of binding to a hormone. The protein concentrations were determined by the Bio-Rad protein assay (Bio-Rad Laboratories, Hercules, Calif., USA). For the test of binding to a hormone, a cytosol, containing 1–3 mg of protein/ml, was incubated overnight at 4° C. with [$^3$H]-Dex (49 Ci/mmol; Radiochemical Center, Amersham, England) or cortisol (67 Ci/mmol; Radiochemical Center, Amersham, England) without (total binding) or with (non-specific binding) a 100-fold excess of radio-inert compound ($10^{-5}$M, Sigma Chemical Co., St. Louis, Mo., USA). The samples were then treated with 1 volume of dextran-charcoal (5% charcoal, 0.5% dextran in the binding solution) for 15 minutes on ice, with constant stirring, and then they were subjected to centrifugation for 10 minutes at 12,000 g. The [$^3$H] ligand attached was measured in an aliquot portion of the supernatant, by scintillation counting. The equilibrium dissociation constant (Kd) of the receptor for dexamethasone or cortisol was determined by Scatchard analysis.

For the competitive binding analysis, the cytosols were incubated with 10 nM [$^3$H]-Dex and various concentrations of nonradioactive competitive steroids, under the same conditions as above. After treatment with dextran-charcoal and scintillation counting, the specific binding was expressed as a percentage of the control not subjected to competition, and plotted as a function of the concentration of steroid in competition. Competitive binding tests in whole cells were carried out on $10^6$ cells incubated for 1 hour at 37° C. with 10 nM [$^3$H]-Dex and various concentrations of steroids in competition. After sonication in 1 ml of KCl buffer (1.5 mM EDTA, 20 mM Tris.HCl, pH 7.4, 0.5 M KCl), the unbound steroid was removed by addition of two volumes of dextran-coated charcoal, in KCl buffer with gelatin (0.05% dextran, 0.5% charcoal, 0.1% gelatin). The mixture was incubated for 30 minutes at 4° C. and it was centrifuged at 3000 g for 5 minutes. The radioactivity was determined by liquid scintillation counting and the specific binding was plotted on a curve as above.

EXAMPLE 2

Chimeric Cre Recombinase Whose Activity is Inducible by Synthetic Glucocorticoids, but not by Natural Glucocorticoids 1. Materials and Methods 1.1. Construction of the Vector pCre-LBD[GR(I747/T)]

A ClaI-XbaI DNA fragment of about 1300 base pairs (bp), containing the sequence coding for the ligand binding domain of the human glucocorticoid receptor was isolated from the plasmid HG1 (see Example 1 (40)) and its ends were filled by T4 polymerase. This fragment was mutated so that the nucleotides ATT coding for an isoleucine at position 747 of the wild-type receptor (56) are replaced by the nucleotides ACC, coding for a threonine. This mutated fragment was cloned into the vector pCre-ER (28) digested with XhoI and PstI whose ends were also filled by T4 polymerase [plasmid pCre⊕GR(I747/T)+F; coding sequence of the LBD of hGR (I747/T) in the same orientation as that of Cre]. pCre-LBD[GR(I747/T)] was obtained by site-directed mutagenesis carried out on the single-stranded DNA prepared from the plasmid pCre+GR (I747/T)+F, with the synthetic oligonucleotides:

SG52 (5'-CTGGAAGATGGCGATCTCGAGATTCAG-CAGGCCACT-3') (SEQ ID NO: 6)

SG53 (5'-CTGTTTCATCAAAAGGGTACCAGCCG-TGGAGGGGCAT-3') (SEQ ID NO. 7)

making it possible to fuse, on the one hand, the DNA sequence coding for Cre [amino acids (aa) 1–343 (orf2(cre); (31)], and that which codes for the region containing the mutated LBD of HG1 [aa 500–777], on the other hand, the previously modified DNA sequence and that coding for the F region of the human estrogen receptor (ER) [aa 553–595 (57)] (FIG. 5). This operation restores the XhoI restriction site situated at the end of the Cre sequences in pCre-ER and introduces a KpnI restriction site between the sequences coding for GR and the F region of ER (FIGS. 6 and 7).

1.2. Mutation of the RXRα Gene

The vector (pRXRα$^{(LNL)}$), used to mutate the RXRαgene (58) by homologous recombination in F9 cells was constructed in the following manner:

A λ phage containing a genomic fragment of 11.8 kb, comprising exons 2, 3 and 4 of RXRα, was isolated from a genomic library prepared with the P19 murine embryo carcinoma genomic DNA, cloned into the EMBL3λ vector. A SalI fragment isolated from this phage (whose ends were filled with T4 polymerase) was subcloned into the BamHI site (after treatment with T4 polymerase) of a derivative of the vector pBluescriptIIsK+ (Stratagene). In this derivative, the XhoI site has been eliminated. An XhoI site was introduced into exon 4 of RXRα at the level of the AccI site corresponding to nucleotide 535 of the cDNA for RXRα (the cDNA sequence for RXR∝ is given in Genbank reference: M 84817), by cloning the following synthetic oligonucleotides into the AccI site:

5'-ATTATTATTACTCGAGTGATGTG-3' (SEQ ID NO: 8) and,

5'-ATCATCATCATCCGAGTAATAATA-3' (SEQ ID NO: 9).

Finally, the XhoI fragment, containing the cassette for expression of the neomycin resistance gene, surrounded by loxP sites, isolated from the vector pHR56 (28) was cloned into the XhoI site of the preceding vector.

The mutation of an allele of the RXRα gene in F9 wells was carried out by homologous recombination with the aid of the vector pRXRα$^{(LNL)}$ (28). This line was called RXRα$^{+/-(LNL)}$.

1.3. Expression of Cre-LBD[GR(I747/T)] in Cells Comprising a Modified DNA Fragment: RXRα$^{(LNL)}$ Transient transfection: 5×10$^6$ RXRα$^{+/-(LNL)}$ cells or HeLa cells resuspended in 500 μl of PBS were electroporated with 5 μg of plasmid pCre-LBD[GR(I747/T)] [optionally cotransfected with 5 μg of the vector pRXRα$^{(LNL)}$ for the HeLa cells] with the aid of an electroporator (Bio-Rad gene pulser), set at 200 V and 960 μF. The cells were then inoculated at 10$^6$ cells per 100 mm dish and treated, if necessary, with ligands.

Stable transfection: 5×10$^6$ RXRα$^{+/-(LNL)}$ cells, resuspended in 500 μl of PBS were electroporated with 5 μg of pCre-LBD[GR(I747/T)] and 1 μg of pPGK-Hyg (59), digested respectively with SalI and PvuII, with the aid of an electroporator (Bio-Rad gene pulser), set at 200 V and 960 μF. The resistant clones were obtained according to the procedure described by Metzger et al. (28).

1.4. "PCR" Amplification of a Genomic DNA Region Located in Exon 4 of RXRα

The DNA amplifications were carried out using the "Polymerase Chain Reaction" (PCR) technique according to the protocol described by Chen and Evans (60). The primers used are: SB211 and PZ105, having respectively as nucleotide sequence 5'-GGCAAACACTATGG-3' (SEQ ID NO: 10) and 5'-TTGCGTACTGTCCTCTT-3' (SEQ ID NO: 11). After denaturation for 8 min at 94° C., 2.5 units of Taq polymerase are added. The amplification is carried out by performing 35 cycles (30 sec. at 94° C., 30 sec. at 50° C.) followed by one cycle (30 sec. at 94° C., 30 sec. at 50° C., 5 min at 72° C.), the product of which is stored at 4° C.

The products of the reactions were separated on polyacrylamide (10%) or agarose (2.5%) gel. The DNA was visualized by UV followed by ethidium bromide staining, or by Southern blotting (42).

1.5. Test of Excision of the Sequences Situated Between the LoxP Sites

The DNA of RXRα$^{+/-(LNL)}$ cells, transfected with pCre-LBD[GR(I747/T)] or the parental vector pSG5, not treated or treated with cortisol (10$^{-6}$ M) or dexamethasone (10$^{-6}$ M) for 72 hours, was subjected to a PCR reaction according to the strategy described in FIG. 8. The products of the reaction were separated on acrylamide gel and stained with ethidium bromide. Lane M in FIG. 9 corresponds to the loading of the pBR322 size marker digested with HinfI. The position of the wild-type and recombinant alleles is indicated.

1.6. PCR Analysis of the Recombinase Activity of Cre-LBD [GR(I747/T)] in the RXRα$^{+/-(LNL)}$ Line Constitutively Expressing the Chimeric Protein For FIG. 10, the DNA prepared from RXRα$^{+/-(LNL)}$:Cre-GR(I747/T) cells not treated or treated with cortisol (10$^{-6}$ M) or with dexamethasone (10$^{-6}$ M) served as a template for carrying out a PCR amplification, according to the procedure described in FIG. 8. The amplified DNA was separated on acrylamide gel and stained with ethidium bromide. Lanes 1, 2, 3 and 4 contain respectively the PCR products produced with DNA extracted from wild-type (WT) F9 cells, RXRα$^{+/-(LNL)}$, RXRα$^{+/-(L)}$ cells and C2RXRα$^{+(L)/-(L)}$ cells (73). Lane 8 contains a size marker (1 kb ladder; GibcoBRL).

In FIG. 11, the DNA prepared from RXRα$^{+/-(LNL)}$:Cre-GR(I747/T) cells not treated or treated with aldosterone, cortisol, corticosterone, dexamethasone, triamcinolone acetonide or RU486, at concentrations ranging from 10$^{-9}$ to 10$^{-6}$ M, served as a template for carrying out a PCR amplification, according to the procedure described in FIG. 8. The amplified DNA was separated on agarose gel and analyzed according to the Southern technique. The amplified fragments corresponding to the wild-type and recombinant alleles were detected by hybridization with the aid of the synthetic oligonucleotide (5'-AAGAAGCCCTTGCAGC-CCTC-3') (SEQ ID NO: 12), radiolabeled at the 5' end with T4 polynucleotide kinase. The signal was visualited and quantified with the aid of a "phosphoimager" (Fujix bas2000).

For FIG. 12, RXRα$^{+/-(LNL)}$:Cre-GR(I747/T) cells were cultured for 72 h in culture medium to which three natural ligands (aldosterone, cortisol and corticosterone) at the concentration of 10$^{-9}$ M or 10$^{-8}$ M and dexamethasone (10$^{-7}$ or 10$^{-6}$ M) have been added as indicated. The recombinant allele was detected according to the procedure described in FIG. 8. The amplified DNA was separated on agarose gel and analyzed according to the Southern technique. The amplified fragments corresponding to the recombinant allele were detected by autoradiography following hybridization with the synthetic oligonucleotide 5'-AATTATAACTTCGTATAATGTATGCTATACGAAGT-TATTC-3' (SEQ ID NO: 13), (containing a loxP site) radiolabeled with Phosphorus$^{32}$ at the 5' end by T4 polynucleotide kinase.

For FIG. 13, HeLa cells were cotransfected with the plasmids pRXRα$^{(LNL)}$ and pCre-LBD[GR(I747/T)] and then cultured for 72 hours with or without addition of the appropriate ligands, at the concentration of 10$^{-7}$ M. The DNA of these cells was then subjected to PCR amplification according to the strategy described. The products of the reaction were separated on acrylamide gel and stained with ethidium bromide. Lane 1 corresponds to the loading of the 1 kb ladder size marker (GibcoBRL).

2. Results

In order to express a Cre recombinase whose activity is inducible by synthetic ligands for the glucocorticoid receptor, but not by natural glucocorticoid ligands at "physiological" concentrations, an expression vector, pCre-LBD [GR(I747/T)], derived from the vector pCre-ER (28) by replacing the DNA sequence coding for amino acids 344–618 containing the LBD of the estrogen receptor (ER), by that coding for amino acids 500–777 of a mutated glucocorticoid receptor (GR) containing the mutated binding domain (LBD) of GR (I747/T), was constructed. The construction of this plasmid led to the insertion of the sequence GGTACC, coding for the aa Gly-Thr at position 624–625 of Cre-LBD[GR(I747/T)] (FIG. 7).

The recombinase activity of Cre-LBD[GR(I747/T)] was tested in a murine cell line RXRα$^{+/-(LNL)}$. This line was obtained by integrating, by homologous recombination, the TK-neo gene, delimited by loxP sites (as a direct repeat) (LNL), into exon 4 of an allele of the RXRα gene (28). The TK-neo gene is a chimeric gene allowing the expression of a thymidine kinase/neomycin resistance gene fusion protein. Electroporation of this line with the vector pCre-LBD[GR (I747/T)] made it possible to evaluate its recombinase activity without addition of ligand, or after addition of cortisol (natural ligand) or of dexamethasone (FIG. 9) (Dex; synthetic ligand). The DNA of the cells thus treated is indeed subjected to a PCR with synthetic oligonucleotides located in exon 4, one upstream of the AccI site, the other downstream of this site. The size of the PCR fragments obtained with this pair of oligonucleotides is 65 bp for the wild-type allele, 3345 bp for the mutated allele (after integration of LNL) and 191 bp for the recombinant allele (after excision of the sequences situated between the two lox sites and of one of the lox sites, see FIG. 8). Following treatment of the cells transfected with dexamethasone ($10^{-6}$ M), a 191 bp fragment is observed, reflecting the presence of sequences corresponding to the recombinant allele, whereas in the absence of treatment or following a treatment with cortisol ($10^{-6}$ M), no fragment of this size is observed. These results therefore show that the recombinase activity of the fusion protein studied may be induced by treating cells expressing this protein with a synthetic GR ligand such as dexamethasone but not with a natural ligand such as cortisol, at the concentration of $10^{-6}$ M.

An RXRα$^{+/-(LNL)}$ line constitutively expressing Cre-LBD [GR(I747/T)] was also established by cointegrating the cassette for expression of the Cre-LBD[GR(I747/T)] gene with a vector expressing the hygromycin resistance gene (RXRα$^{+/-(LNL)}$:Cre-GR(I747/T); see "Materials and Methods"; data not presented). The recombinase activity was tested following a treatment of these cells with Dex ($10^{-6}$ M) for 72 hours. Analysis of the products of the PCRs carried out on the DNA of these cells reveals a fragment of 191 bp corresponding to the recombinant allele alone after treatment with Dex (FIG. 10).

Thus, it is shown that Cre-LBD[GR(I747/T)] is inactive without addition of ligand or in the presence of cortisol at $10^{-6}$ M, but active in the presence of Dex, when its expression cassette is integrated into the genome.

The kinetics of recombinase action was also evaluated: its activity is detectable from 12 h of treatment with dexamethasone at $10^{-6}$ M, but it is considerably stronger after 72 h of treatment (results not presented).

The recombinase activity of Cre-LBD[GR(I747/T)] was also tested following the addition of various concentrations of ligands. No recombinase activity could be observed in the RXRα$^{+/-(LNL)}$:Cre-GR(I747/T) cells treated with aldosterone, with cortisol or with corticosterone (ligand concentration ranging from $10^{-9}$ to $10^{-6}$ M), whereas in the presence of dex, of triamcinolone acetonide or of RU486, a recombinase activity is observed from $10^{-9}$ M (FIG. 11).

It was also shown, with the aid of this cell line, that the recombinase activity of Cre-LBD[GR(I747/T)] may be induced by synthetic ligands even when the cells are cultured in the presence of natural ligands (aldosterone, cortisol and corticosterone) at $10^{-9}$ or $10^{-8}$ M. The excision of sequences located between the loxP sites is obtained following a treatment of 72 h with dexamethasone at $10^{-7}$ M or $10^{-6}$ M (FIG. 12).

The recombinase activity of Cre-LBD[GR(I747/T)] was finally tested in human cells: HeLa cells were transiently cotransfected with the vectors pCre-LBD[GR(I747/T)] and pRXRα$^{(LNL)}$, and then cultured either without addition of ligand, or in the presence of the ligands indicated in FIG. 13. As in the F9 cells, a 191 bp band corresponding to the recombinant fragment is amplified from DNA isolated from the cells treated with synthetic ligands (Dexamethasone, Triamcinolone acetonide or RU486 at $10^{-7}$ M), whereas without addition of ligand, or in the presence of natural ligands such as aldosterone, corticosterone or cortisol at the same concentrations, only the fragment corresponding to the wild-type allele can be detected.

These results therefore show that the recombinase activity of the fusion protein Cre-LBD[GR(I747/T)] is induced by synthetic ligands for the glucocorticoid receptor, whereas it is insensitive to the natural ligands such as cortisol, corticosterone or aldosterone, even at concentrations as high as $10^{-6}$ M. Furthermore, the presence of natural ligands does not prevent the induction of the recombinase activity of Cre-LBD[GR(I747/T)] by the synthetic ligands.

EXAMPLE 3

Induction of the Activity of a Chimeric Cre Recombinase in Mice

1. Materials and Methods 1.1. Construction of Plasmids and Establishment of Transgenic Mice The vector pCMVCre-LBD[GR(I747/T)] was constructed by cloning the 2 kb EcoRI fragment isolated from pCre-LBD[GR(I747/T)] into the EcoRI site of pMGSV1 (60). The 4.64 kb PvuII fragment isolated from pCMVCre-LBD[GR(I747/T)] was injected into F1 zygotes (C57BL/6× SJL) at a concentration of 4 ng/μl so as to produce transgenic mice according to the conventional procedure (61).

1.2. PCR Conditions

The PCR amplifications were carried out in a buffer solution containing 10 mM Tris-HCl (pH 8.8), 50 mM KCl, 1.5 mM MgCl2, 0.2 mM dNTPs, 0.25 μM of each primer, 2 units of Taq polymerase and 1 μg of genomic DNA as template. After 30 cycles (30 sec at 94° C., 30 sec at 550° C., 1 min at 72° C.) and then 1 cycle (30 sec at 90° C., 30 sec at 550° C., 5 min at 72° C.), the amplification products were separated on a 2.2% agarose gel stained with ethidium bromide.

1.3. Analysis of the Genotype of the Mice.

The transgene Cre-LBD[GR(I747/T)] and the wild-type allele and the excised allele RXRα$^{ΔAF2(LNL)}$ were detected by PCR. The detection of the transgene Cre-LBD[GR(I747/T)] was carried out with the aid of the nucleotide primers 5'-ATCCGAAAAGAAAACGTTGA-3' (SEQ ID NO: 14) and 5'-ATCCAGGTTACGGATATAGT-3' (SEQ ID NO: 15), that of the alleles of the RXRα gene using the primers 5'-GGTTCTCCGGCCGCTTGGGT-3' (SEQ ID NO: 16) and 5'-GAAGGCGATGCGCTGCGAAT-3' (SEQ IN NO: 17). In the same matter, the excision of the tk-neo marker delimited by loxP sites was followed by PCR with the aid of the primers A (5'-CAAGGAGCCTCCTTTCTCTA-3') (SEQ ID NO: 18) and B (5'-CCTGCTCTACCTGGTGACTT-3')

(SEQ ID NO 19. These primers amplify a DNA fragment of 156 base pairs from the wild-type allele and a fragment of 190 base pairs from the excised allele RXRα$^{\Delta AF2(L)}$.

2. Results

Figure 14A:
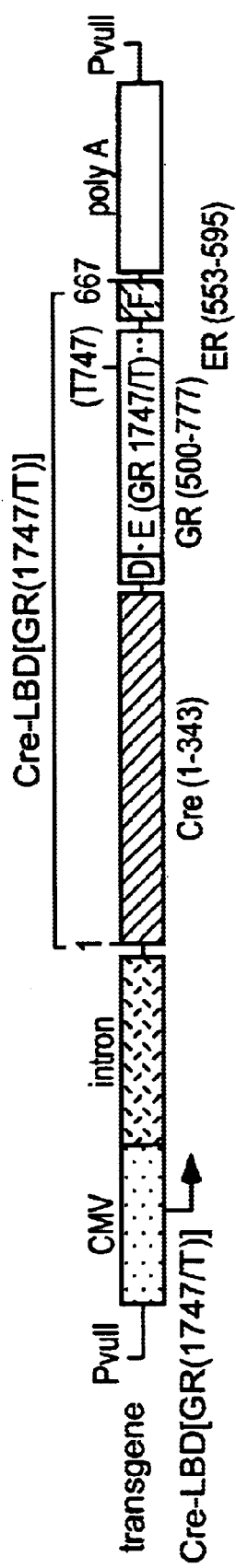
Figure 14B:
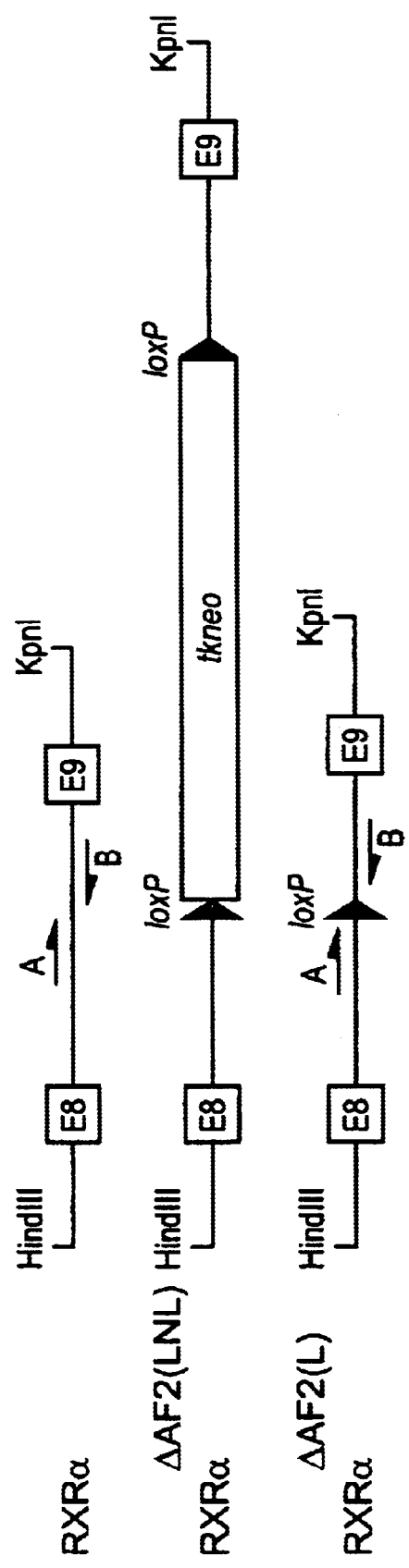

The recombinase activity of Cre-LBD[GR(I747/T)] was also tested in mice. Thus, transgenic mice expressing the fusion protein Cre-LBD[GR(I747/T)] under the control of the promoter of the human cytomegalovirus "major IE" gene were established. The structure of the transgene is represented in FIG. 14a. It contains the activating/promoter sequences of the human cytomegalovirus "major IE" gene, an intron of the rabbit β-globin gene, coding sequences of Cre-LBD[GR(I747/T)] and the simian virus SV40 polyadenylation signal. The site of initiation of transcription is indicated by an arrow. These mice were then crossed with "reporter" mice so as to demonstrate therein the existence of an induced recombinase activity. This "reporter" line contains an insertion of the tk-neo selectable marker, delimited by loxP sites, in the intron situated between exons 8 and 9 of the RXRα gene, on one of its two alleles [RXRα$^{AAF2}$ $^{(LNL)}$]. After recombination of the tkneo marker, a loxP site remains in place and constitutes the excised allele RXRα$^{\Delta AF2}$ $_{(L)}$. The wild-type RXRα allele and the excised allele may be detected simultaneously by PCR amplification using an appropriate primer pair A and B. FIG. 14b schematically represents this PCR strategy by indicating the A and B primers as well as certain restriction sites.

The progeny derived from crossing Cre-LBD[GR(I747/T)] mice and "reporter" mice, described above, containing both the transgene Cre-LBD[GR(I747/T)] and the allele RXRα$^{\Delta AF2\ (LNL)}$ was identified by establishing their genotype from a tail biopsy. One of these mice was subjected, at the age of four weeks, to a daily incraperitoneal injection of 0.3 mg of dexamethasone diluted in 100 μl of vegetable oil, for five days. A tail biopsy was taken the day before the first injection, as well as the day after the fifth injection. The DNA isolated from these samples was analyzed by PCR with the aid of the oligonucleotides A and B (FIG. 15, lanes 2 and 3) to determine if the treatment induces the deletion of the tk-neo marker. Lane 1 corresponds to a control reaction, carried out without DNA. The position of the PCR products amplified using the wild-type RXRα allele and the excised allele RXRα$^{AAF2\ (L)}$ are indicated. The size marker (lane 4) corresponds to the 1 kb ladder (GibcoBRL). The size of the fragments is given as base pairs. According to FIG. 15, the induced excision indeed took place after treatment of the mouse tested with dexamethasone. Indeed, the analysis of the DNA fragments amplified from the tail before treatment reveals only the presence of the wild-type RXRα allele whereas the analysis of the tail of the same mouse, after treatment, indicates the presence of the excised allele RXRα$^{AAF2\ (LNL)}$ (FIG. 15). Thus, it appears that the chimeric recombinase Cre-LBD[GR(I747/T)] exhibits no basic constitutive activity in the presence of the endogenous ligands. It is, however, induced and active in mice by treatment with dexamethasone.

REFERENCES

1. Evans R M, 1988, The steroid and thyroid hormone receptor superfamily. Science 240:889–895.
2. Beato M., 1989, Gene regulation by steroid hormones. Cell 56:335–344.
3. Green S, Chambon P., 1988, Nuclear receptors enhance our understanding of transcription regulation. Trends Genetique 4:309–314.
4. Parker M G, 1993, Steroid and related receptors. Curr. Opin. Cell. Biol. 5:499–504.
5. Simons S S Jr, 1994, Function/activity of specific amino acids in glucocorticoid receptors, New York. Vitam. Horm. 49:49–130.
6. Danielian P S, White R, Lees J A, Parker M G, 1992, Identification of a conserved region required for hormone dependent transcriptional activation by steroid hormone receptors. EMBO J. 11:1025–1033.
7. Saatcioglu F., Bartunek P., Deng T., Zenke M., Karin M., 1993, A conserved C-terminal sequence that is deleted in v-ErbA is essential for the biological activities of c-ErbA (the thyroid hormone receptor). Mol. Cell. Biol. 13:3675–3685.
8. Barettino D., Vivanco Ruiz MdM., Stunnenberg H G., 1994, Characterization of the ligand-dependent transactivation domain of thyroid hormone receptor. EMBO J. 13:3039–3049.
9. Durand B., Saunders M., Gaudon C., Roy B., Losson R., Chambon P., 1995, Activation function 2 (AF-2) of retinoic acid receptor and 9-cis retinoic acid receptor: presence of a conserved autonomous constitutive activating domain and influence of the nature of the response element on AF-2 activity. EMBO J. 13:5370–5382.
10. Leng X H., Blanco J., Tsai S Y., Ozato K., O'Malley B W., 1995, Mouse retinoid X receptor contains a separable ligand-binding and transactivation domain in its E region. Mol. Cell. Biol. 15:255–263.
11. Cavaillès V., Dauvois S., Danielian P S., Parker M G., 1994, Interaction of protein with transcriptionally active estrogen receptors, Proc. Natl. Acad. Sci. USA 91:10009–10013.
12. Halachmi S., Marden E., Martin G., MacKay H., Abbondanza C., Brown M., 1994, Estrogen receptor-associated proteins: possible mediators of hormone-induced transcription. Science 264:1455–1458.
13. Le Douarin B., Zechel C., Garnier J M., Lutz Y., Tora L., Pierrat B., Heery D., Gronemeyer H., Chambon P., Losson R. 1995, The N-terminal part of TIFI, a purative mediator of the ligand-dependent activation function (AF-2) of nuclear receptors, is fused to B-raf in the oncogenic protein T18. EMBO J. 14:2020–2033.
14. Cavaillès V., Dauvois S., L'Horset F., Lopez G., Hoare S., Kushner P J., Parker M G., 1995, Nuclear factor RIP 140 modulates transcriptional activation by the estrogen receptor. EMBO J. 14:3741–3751.
15. Lee J W., Ryan F., Swaffield J., Johnston S A., Moore D D., 1995, Interaction of thyroid-hormone receptor with a conserved transcriptional mediator. Nature 374:91–94.
16. Baur et al., EMBO J., Vol. 15 No. 1, 110–124, 1996.
17. Bourguet W., Ruff P., Chambon P., Gronemeyer H., Moras D., 1995, Crystal structure of the ligand-binding domain of the human nuclear receptor RXR-α. Nature 375:377–382.
18. Renaud et al., Nature, Vol No. 378 681–689, 1995.
19. Wurtz et al., Natural Structural Biology, Vol. 3, 87–93, 1996.
20. Chakraborti P K., Garebedian M J., Yamamoto K R., Simons S S J., 1991, Creation of "super" glucocorticoid receptors by point mutations in the steroid binding domain. J. Biol. Chem. 266:22075–22078.
21. Warriar N., Yu C., Govindan M V., 1994, Hormone binding domain of human glucocorticoid receptor enhancement of transactivation function by substitution mutants M565R and A573Q. J. Biol. Chem. 269:29010–29015.
22. Chen D., Kohli K., Zhank S., Danielsen M., Stallcup M R., 1994 Phenylalamine-780 near the C-terminus of the mouse glucocorticoid receptor is important for ligand binding affinity and specificity. Mol. Endocrinol. 8:422–430.
23. Hurley D M., Accili D., Stratakis C A., Karl M., Vamvakopoulos N., Rorer E., Constantine K., Taylor S I., Chrousos G P., 1991, Point mutation causing a single amino acid substitution in the hormone binding domain of the glucocorticoid receptor in familial glucocorticoid resistance. J. Clin. Invest. 87:680–686.
24. Keightley M C., Fuller P J., 1994, Unique sequences in the Guinea Pig glucocorticoid receptor induce constitutive transactivation and decrease steroid sensitivity. Mol. Endocrinol. 8:431–439.
25. Chen D., Stallcup M R., 1994, The hormone-binding role of 2 cysteines near the C terminus of the mouse glucocorticoid receptor. J. Biol. Chem. 269:7914–1978.
26. Byravan S., Milhon J., Rabindran S K., Olinger B., Garabedian M J., Danielsen M., Stallcup M R., 1991, Two point mutations in the hormone-binding domain of the mouse glucocorticoid receptor that dramatically reduce its function. Mol. Endocrinol. 5:752–758.
27. Picard, Current opinion in biotechnology, 1994, 5:511515.
28. Metzger et al., PNAS USA Vol 92, July 1995, Genetics 6991–6995.
29. Logie et al., PNAS USA Vol 92, June 1995, Genetics, 5940–5944.
30. Littlewood et al., Nucleic Acids Research 1995, Vol. 23 No. 10, 1686–1690.
31. Sternberg et al., J. Mol. Biol. (1986), 187:197–212.
32. Sauer and Henderson, The New Biologist, Vol. 2, No. 5, (May 1990), 441–449.
33. Barbonis et al., Nucleic Acids Research, 1993, Vol. 21, No. 9, 2025–2029.
34. Kilby et al., TIG, December 1993, Vol. 9, 413–421.
35. Sauer, Current opinion in Biotechnology, 1994, 5:521–527.
36. Denisen et al., PNAS USA Vol 92, (August 1995), Genetics, 7376–7380,
37. C. Babinet, Medecine/Sciences, 1995, No. 8 Vol. 11, 1154–1157.
38. Malchoff D M., Brufsky A., Reardon G., McDermott P., Javier E C., Bergh C H., Rowe D., Malchoff C D., 1993, A mutation of the glucocorticoid receptor in primary cortisol resistance. J. Clin. Invest. 91:1918–1925.
39. J. C. Kaplan and M. Delpech, Biologie Moleculaire et Mèdecine, 2ème Edition, Edition Flammarion.
40. Kumar V., Green S., Stack G., Berry M., Jin J R., Chambon P., 1987, Functional domains of the human estrogen receptor. Cell. 51:941–951.
41. Green S., Issemann I., Sheer E., 1988, A versatile in vivo and in vitro eukaryotic expression vector for protein engineering. Nucl. Acids. Res. 16:369.
42. Sambrook J., Fritsch E F., Maniatis T., 1989, Molecular cloning. A laboratory manual. In: eds. Cold Spring Harbor, N.Y. Cold Spring Harbor Laboratory Press.
43. Webster N J G., Green S., Jin J R., Chambon P., 1988, The hormone-bnding domains of the estrogen and glucocorticoid receptors contain an inducible transcription activation function. Cell. 54:199–207.
44. Lanz R B., Rusconi S., 1994, A conserved carboxy-terminal subdomain is important for ligand interpretation and transactivation by nuclear receptors. Endocrinology 135:2183–2195.
45. Mahfoudi A., Roulet E., Dauvois S., Parker M G., Wahli I J., 1995, Specific mutations in the estrogen receptor change the properties of antiestrogens to full agonists. Proc. Natl. Acad. Sci. USA 92:4206–4210.
46. Vegeto E., Allan G F., Schrader W T., Tsai M J., McDonnel D P., O'Malley B W., 1992, The mecanism of RU486 antagonism is dependent on the conformation of the carboxy-terminal tail of the human progesterone receptor. Cell. 69:703–713.
47. McKnight S., Tjian R. 1986, Transcriptional selectivity of viral genes in Mammalian cells. Cell. 46:795–805.
48. Schwartz O., Vlrelizier J L., Montagnier L., Hazan U., 1990, A microtransfection method using the luciferase-encoding reporter gene for the assay of human immunodeficiency virus LTR promoter activity. Gene 88:197–205.
49. Bocquel M T., Kumar V., Stricker C., Chambon P., Gronemeyer H., 1989, The contribution of the N- and C-terminal regions of steroid receptors to activation of transcription is both receptor and cell-specific. Nucl. Acids. Res. 17:2581–2595.
50. Grange T., Roux J., Rigaud G., Pictet R., 1989, Two remote glucocorticoid responsive units interact cooperatively to promote glucocorticoid induction of rat tyrosine aminotransferase gene expression. Nucl. Acids. Res. 17:8695–8709.
51. Pons M., Gagne D., Nicolas J C., Mehtali M., 1990, A new cellular model of response to estrogens: a bioluminescent test to characterize (anti)estrogen molecules. Bio Techniques 9:450–459.
52. Green S., Kumar V., Theulaz I., VIahli W., Chambon P., 1988, The N-rerminal 'zinc finger' of the oestrogen and glucocorticoid receptors determines target gene specificity. EMBO J. 7:3037–3044.
53. De Wet J R., Wood K V., De Luca M., Helinski D R., Subramani S., 1987, Firefly luciferase gene: structure and expression in mammalian cells. Mol. Cell. Biol. 7:725–737.
54. Jausons-Loffreda N., Balaguer P., Roux S., Fuentes M., Pons M., Nicolas J C., Gelmini S., Pazzagli M., 1994, Chimeric receptors as a tool for luminescent measurement of biological activities of steroid hormones. Jour. Bioluminescence and Chemiluminescence 9:217–221.
55. Kakidanj H., Ptashne M., 1988, Gal4 activated gene expression in mammalian cells. Cell. 52:161–167.
56. Hollenberg S M., Weinberger C., Ong E S., Cerelli G., Oro A., Lebo R., Thompson E B., Rosenfeld M G., Evans R M., 1985, Primary structure and expression of a human glucocorticoid receptor cDNA. Nature 318:635–641.
57. Green et al., 1986, Nature 320, 134–139.
58. Mangelsdorf D. J., Borgmeyer V., Heyman R. A., Zhow J Y., Ony E. S., Oro A. E., Kakizuka A and Evans R. M., 1992, Genes and Development 6, 329–344.
59. Riele et al., 1990, Nature 348, 649–651.60. Chen and Evans (1993) (Methods in molecular biology, Vol 15: PCR protocols current methods and applications chap. 7, Edited by: BA White Copyright, 1993, Humana Press Inc. Totowa, N.J.).
60. R. Feil, J. Brocard, B. Mascrez, M. LeMeur, D. Metzger, P. Chambon. (1996) Ligand-activated site-specific recombination in mice. Proc. Natl. Acad. Sci. U.S.A., 93, 10887–10890.
61. Hogan, B., Costantini, F., & Lacy, E. (1986) Manipulating the Mouse Embryo: A Laboratory Manual (Cold Spring Harbor Lab., Cold Spring Harbor, N.Y.).

What is claimed is:

1. A polynucleotide comprising a nucleic acid sequence coding for a modified nuclear glucocorticoid receptor, wherein said nucleic acid sequence is the cDNA sequence of the human nuclear glucocorticoid receptor as represented in SEQ ID NO: 2, so that the transcriptional activity of the human nuclear glucocorticoid receptor is more strongly inducible by a synthetic glucocorticoid ligand than by a natural glucocorticoid.

2. The polynucleotide according to claim 1, wherein said nucleic acid sequence is the cDNA of the human nuclear glucocorticoid receptor as represented in SEQ ID NO: 1.

3. A polynucleotide comprising a nucleic acid sequence coding for a ligand binding domain (LBD) of a nuclear glucocorticoid receptor, said ligand binding domain comprising a nucleic acid sequence coding for an amino acid sequence as represented in SEQ ID NO: 2 from no acid 532 to amino acid 777, so that the activity of said ligand binding domain is more strongly inducible by binding to a synthetic glucocorticoid ligand than by binding to a natural glucocorticoid.

4. The polynucleotide according to claim 3, comprising a nucleic acid sequence coding for the ligand binding domain (LBD) of the human nuclear glucocorticoid receptor having the nucleotide sequence as represented in SEQ ID NO: 1 from nucleotide 1594 to nucleotide 2334.

5. A modified nuclear glucocorticoid receptor, comprising an amino acid sequence as represented in SEQ ID NO: 2, so that the transcriptional activity of said receptor is more strongly inducible by a synthetic glucocorticoid ligand than by a natural glucocorticoid ligand.

6. A ligand binding domain of a nuclear glucocorticoid receptor wherein said ligand binding domain is of the human nuclear glucocorticoid receptor and comprises the amino acid sequence of the ligand binding domain of the human glucocorticoid receptor as represented in SEQ ID NO: 2 from amino acid 532 to amino acid 777, so that the activity of said ligand binding domain is more strongly inducible by a synthetic glucocorticoid ligand tan by a natural glucocorticoid ligand.

7. A vector system for conditionally expressing a protein in host cells, the expression of which is induced in the presence of a synthetic glucocorticoid ligand, and said vector system comprising:

a first DNA fragment comprising a nucleic acid sequence coding for said protein under the control of elements ensuring its expression in said host cells, said elements ensuring its expression comprising a sequence for control of transcription (RE) being recognized by a modified glucocorticoid receptor mutated in the region of the ligand binding domain between the H11 and H12 helices, so that the activity of said modified receptor is more strongly inducible by a synthetic glucocorticoid ligand than by a natural glucocorticoid ligand, said modified receptor being complexed with said synthetic glucocorticoid ligand, and a second DNA fragment encoding said modified glucocorticoid receptor comprising a polynucleotide coding for:

the ligand binding domain (LBD) region of the human glucocorticoid receptor comprising an amino acid sequence as represented in SEQ ID NO: 2 from amino acid 532 to amino acid 777, and the DNA binding domain (DBD) region of the human glucocorticoid receptor comprising an amino acid sequence as represented in SEQ ID NO: 2 from amino acid 421 to amino acid 487, said polynucleotide being placed under the control of the elements assuring its expression in said host cells, said first and second DNA fragments being carried by the same vector or two vectors separately.

8. A method for expressing a foreign protein in human or animal cells in vitro comprising culturing cells which contain a vector system according to claim 7, in the presence of a synthetic glucocorticoid ligand to induce expression of the foreign protein and, recovering the expressed foreign protein.

9. The method according to claim 8, wherein said synthetic ligand is selected from the group consisting of dexamethasone, triamcinolone acetonide, RU2836, bimetrazole, deacylcortivazol and fluocinolone acetonide.

10. A polynucleotide sequence coding for a polypeptide comprising:
  (a) a nucleic acid encoding a polypeptide wherein said encoded polypeptide comprises the human nuclear glucocorticoid receptor comprising amino acid 532 to amino acid 777 of SEQ ID NO:2, wherein the activity of a ligand binding domain of the encoded polypeptide is more strongly inducible by binding to a synthetic glucocorticoid ligand than by binding to a natural glucocorticoid; and
  (b) a second nucleic acid comprising a DNA binding domain.

11. The polynucleotide according to claim 10, wherein said DNA binding domain is of a site-specific DNA-binding factor.

12. The polynucleotide according to claim 11, wherein said site-specific DNA-binding factor is the yeast Gal 4 protein.

13. A polypeptide comprising (a) a ligand binding domain (LBD) of a nuclear glucocorticoid receptor, said ligand binding domain comprising the amino acid sequence of the human nuclear glucocorticoid receptor as set forth in SEQ ID NO: 2 from amino acid 532 to amino acid 777, so that the activity of said ligand binding domain is more strongly inducible by binding to a synthetic glucocorticoid ligand than by binding to a natural glucocorticoid and (b) a DNA binding domain.

14. The polypeptide according to claim 13, wherein said DNA binding domain is of a nuclear glucocorticoid receptor.

15. The polypeptide according to claim 13, wherein said DNA binding domain is of a site-specific DNA-binding factor.

16. The polypeptide according to claim 15, wherein said site-specific DNA-binding factor is the yeast Gal 4 protein.

17. A vector system for conditionally expressing a protein in host cells, said vector system being inducible in the presence of a synthetic glucocorticoid ligand, said vector system comprising:
  a first DNA fragment comprising a nucleic acid sequence coding for said protein under the control of elements ensuring the expression in said host cells, said elements ensuring its expression comprising a sequence for control of transcription (RE) being recognized by the DNA binding domain of a polypeptide comprising (a) the ligand binding domain (LBD) region of the human glucocorticoid receptor comprising an amino acid sequence as represented in SEQ ID NO: 2 from amino acid 532 to amino acid 777, so that the activity of said ligand binding domain is more strongly inducible by binding to a synthetic glucocorticoid ligand than by binding to a natural glucocorticoid and (b) a DNA binding domain of a site-specific DNA-binding factor which binds to said sequence for control of the transcription (RE), said polypeptide being complexed with said synthetic glucocorticoid ligand, and
  a second DNA fragment comprising a polynucleotide coding for said polypeptide placed under the control of the elements assuring its expression in said host cells,
  said first and second DNA fragments being carried by the same vector or two vectors separately.

18. The vector system according to claim 17 wherein said site-specific DNA-binding factor is the yeast protein Gal 4 and said sequence for control of transcription (RE) is the 17 m sequence recognized by the Gal4 transactivator.

19. The method according to claim 8, wherein said vector system is inducible in the presence of a synthetic glucocorticoid ligand, said vector system comprising:
  a first DNA fragment comprising a nucleic acid sequence coding for said protein under the control of elements ensuring the expression in said host cells, said elements ensuring its expression comprising a sequence for control of transcription (RE) being recognized by the DNA binding domain of a polypeptide comprising (a) a ligand binding domain (LBD) of a nuclear glucocorticoid receptor, said ligand binding domain comprising an amino acid sequence as represented in SEQ ID NO: 2 from amino acid 532 to amino acid 777, so that the activity of said ligand binding domain is more strongly inducible by binding to a synthetic glucocorticoid ligand than by binding to a natural glucocorticoid and (b) a DNA binding domain of a site-specific DNA-binding factor which binds to said sequence for control of the transition (RE), said polypeptide being complexed with said synthetic glucocorticoid ligand, and
  a second DNA fragment comprising a polynucleotide coding for said polypeptide placed under the control of the elements assuring its expression in said host cells,
  said first and second DNA fragments being carried by the same vector or two vectors separately; and
  wherein said site-specific DNA-binding factor is the yeast protein Gal 4 and said sequence for control of transcription (RE) is the 17 m sequence recognized by the Gal4 transactivator.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 2334 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..2331

(ix) FEATURE:
      (A) NAME/KEY: -
      (B) LOCATION: 1..2331
      (D) OTHER INFORMATION: /note= "GR(I747/T) (Human
          glucocorticoid receptor mutated at position 747)."

(xi) SEQUENCE DESCRIPTION: SEQ ID NO: 1:

```
ATG GAC TCC AAA GAA TCA TTA ACT CCT GGT AGA GAA GAA AAC CCC AGC    48
Met Asp Ser Lys Glu Ser Leu Thr Pro Gly Arg Glu Glu Asn Pro Ser
 1               5                  10                  15

AGT GTG CTT GCT CAG GAG AGG GGA GAT GTG ATG GAC TTC TAT AAA ACC    96
Ser Val Leu Ala Gln Glu Arg Gly Asp Val Met Asp Phe Tyr Lys Thr
             20                  25                  30

CTA AGA GGA GGA GCT ACT GTG AAG GTT TCT GCG TCT TCA CCC TCA CTG   144
Leu Arg Gly Gly Ala Thr Val Lys Val Ser Ala Ser Ser Pro Ser Leu
         35                  40                  45

GCT GTC GCT TCT CAA TCA GAC TCC AAG CAG CGA AGA CTT TTG GTT GAT   192
Ala Val Ala Ser Gln Ser Asp Ser Lys Gln Arg Arg Leu Leu Val Asp
     50                  55                  60

TTT CCA AAA GGC TCA GTA AGC AAT GCG CAG CAG CCA GAT CTG TCC AAA   240
Phe Pro Lys Gly Ser Val Ser Asn Ala Gln Gln Pro Asp Leu Ser Lys
 65                  70                  75                  80

GCA GTT TCA CTC TCA ATG GGA CTG TAT ATG GGA GAG ACA GAA ACA AAA   288
Ala Val Ser Leu Ser Met Gly Leu Tyr Met Gly Glu Thr Glu Thr Lys
                 85                  90                  95

GTG ATG GGA AAT GAC CTG GGA TTC CCA CAG CAG GGC CAA ATC AGC CTT   336
Val Met Gly Asn Asp Leu Gly Phe Pro Gln Gln Gly Gln Ile Ser Leu
            100                 105                 110

TCC TCG GGG GAA ACA GAC TTA AAG CTT TTG GAA GAA AGC ATT GCA AAC   384
Ser Ser Gly Glu Thr Asp Leu Lys Leu Leu Glu Glu Ser Ile Ala Asn
        115                 120                 125

CTC AAT AGG TCG ACC AGT GTT CCA GAG AAC CCC AAG AGT TCA GCA TCC   432
Leu Asn Arg Ser Thr Ser Val Pro Glu Asn Pro Lys Ser Ser Ala Ser
    130                 135                 140

ACT GCT GTG TCT GCT GCC CCA ACA GAG AAG GAG TTT CCA AAA ACT CAC   480
Thr Ala Val Ser Ala Ala Pro Thr Glu Lys Glu Phe Pro Lys Thr His
145                 150                 155                 160

TCT GAT GTA TCT TCA GAA CAG CAA CAT TTG AAG GGC CAG ACT GGC ACC   528
Ser Asp Val Ser Ser Glu Gln Gln His Leu Lys Gly Gln Thr Gly Thr
                165                 170                 175

AAC GGT GGC AAT GTG AAA TTG TAT ACC ACA GAC CAA AGC ACC TTT GAC   576
Asn Gly Gly Asn Val Lys Leu Tyr Thr Thr Asp Gln Ser Thr Phe Asp
            180                 185                 190
```

```
ATT TTG CAG GAT TTG GAG TTT TCT TCT GGG TCC CCA GGT AAA GAG ACG         624
Ile Leu Gln Asp Leu Glu Phe Ser Ser Gly Ser Pro Gly Lys Glu Thr
            195                 200                 205

AAT GAG AGT CCT TGG AGA TCA GAC CTG TTG ATA GAT GAA AAC TGT TTG         672
Asn Glu Ser Pro Trp Arg Ser Asp Leu Leu Ile Asp Glu Asn Cys Leu
            210                 215                 220

CTT TCT CCT CTG GCG GGA GAA GAC GAT TCA TTC CTT TTG GAA GGA AAC         720
Leu Ser Pro Leu Ala Gly Glu Asp Asp Ser Phe Leu Leu Glu Gly Asn
225                 230                 235                 240

TCG AAT GAG GAC TGC AAG CCT CTC ATT TTA CCG GAC ACT AAA CCC AAA         768
Ser Asn Glu Asp Cys Lys Pro Leu Ile Leu Pro Asp Thr Lys Pro Lys
            245                 250                 255

ATT AAG GAT AAT GGA GAT CTG GTT TTG TCA AGC CCC AGT AAT GTA ACA         816
Ile Lys Asp Asn Gly Asp Leu Val Leu Ser Ser Pro Ser Asn Val Thr
            260                 265                 270

CTG CCC CAA GTG AAA ACA GAA AAA GAA GAT TTC ATC GAA CTC TGC ACC         864
Leu Pro Gln Val Lys Thr Glu Lys Glu Asp Phe Ile Glu Leu Cys Thr
            275                 280                 285

CCT GGG GTA ATT AAG CAA GAG AAA CTG GGC ACA GTT TAC TGT CAG GCA         912
Pro Gly Val Ile Lys Gln Glu Lys Leu Gly Thr Val Tyr Cys Gln Ala
            290                 295                 300

AGC TTT CCT GGA GCA AAT ATA ATT GGT AAT AAA ATG TCT GCC ATT TCT         960
Ser Phe Pro Gly Ala Asn Ile Ile Gly Asn Lys Met Ser Ala Ile Ser
305                 310                 315                 320

GTT CAT GGT GTG AGT ACC TCT GGA GGA CAG ATG TAC CAC TAT GAC ATG        1008
Val His Gly Val Ser Thr Ser Gly Gly Gln Met Tyr His Tyr Asp Met
            325                 330                 335

AAT ACA GCA TCC CTT TCT CAA CAG CAG GAT CAG AAG CCT ATT TTT AAT        1056
Asn Thr Ala Ser Leu Ser Gln Gln Gln Asp Gln Lys Pro Ile Phe Asn
            340                 345                 350

GTC ATT CCA CCA ATT CCC GTT GGT TCC GAA AAT TGG AAT AGG TGC CAA        1104
Val Ile Pro Pro Ile Pro Val Gly Ser Glu Asn Trp Asn Arg Cys Gln
            355                 360                 365

GGA TCT GGA GAT GAC AAC TTG ACT TCT CTG GGG ACT CTG AAC TTC CCT        1152
Gly Ser Gly Asp Asp Asn Leu Thr Ser Leu Gly Thr Leu Asn Phe Pro
            370                 375                 380

GGT CGA ACA GTT TTT TCT AAT GGC TAT TCA AGC CCC AGC ATG AGA CCA        1200
Gly Arg Thr Val Phe Ser Asn Gly Tyr Ser Ser Pro Ser Met Arg Pro
385                 390                 395                 400

GAT GTA AGC TCT CCT CCA TCC AGC TCC TCA ACA GCA ACA ACA GGA CCA        1248
Asp Val Ser Ser Pro Pro Ser Ser Ser Thr Ala Thr Thr Gly Pro
            405                 410                 415

CCT CCC AAA CTC TGC CTG GTG TGC TCT GAT GAA GCT TCA GGA TGT CAT        1296
Pro Pro Lys Leu Cys Leu Val Cys Ser Asp Glu Ala Ser Gly Cys His
            420                 425                 430

TAT GGA GTC TTA ACT TGT GGA AGC TGT AAA GTT TTC TTC AAA AGA GCA        1344
Tyr Gly Val Leu Thr Cys Gly Ser Cys Lys Val Phe Phe Lys Arg Ala
            435                 440                 445

GTG GAA GGA CAG CAC AAT TAC CTA TGT GCT GGA AGG AAT GAT TGC ATC        1392
Val Glu Gly Gln His Asn Tyr Leu Cys Ala Gly Arg Asn Asp Cys Ile
450                 455                 460

ATC GAT AAA ATT CGA AGA AAA AAC TGC CCA GCA TGC CGC TAT CGA AAA        1440
Ile Asp Lys Ile Arg Arg Lys Asn Cys Pro Ala Cys Arg Tyr Arg Lys
465                 470                 475                 480

TGT CTT CAG GCT GGA ATG AAC CTG GAA GCT CGA AAA ACA AAG AAA AAA        1488
Cys Leu Gln Ala Gly Met Asn Leu Glu Ala Arg Lys Thr Lys Lys Lys
            485                 490                 495

ATA AAA GGA ATT CAG CAG GCC ACT ACA GGA GTC TCA CAA GAA ACC TCT        1536
Ile Lys Gly Ile Gln Gln Ala Thr Thr Gly Val Ser Gln Glu Thr Ser
            500                 505                 510
```

```
GAA AAT CCT GGT AAC AAA ACA ATA GTT CCT GCA ACG TTA CCA CAA CTC      1584
Glu Asn Pro Gly Asn Lys Thr Ile Val Pro Ala Thr Leu Pro Gln Leu
        515                 520                 525

ACC CCT ACC CTG GTG TCA CTG TTG GAG GTT ATT GAA CCT GAA GTG TTA      1632
Thr Pro Thr Leu Val Ser Leu Leu Glu Val Ile Glu Pro Glu Val Leu
        530                 535                 540

TAT GCA GGA TAT GAT AGC TCT GTT CCA GAC TCA ACT TGG AGG ATC ATG      1680
Tyr Ala Gly Tyr Asp Ser Ser Val Pro Asp Ser Thr Trp Arg Ile Met
545                 550                 555                 560

ACT ACG CTC AAC ATG TTA GGA GGG CGG CAA GTG ATT GCA GCA GTG AAA      1728
Thr Thr Leu Asn Met Leu Gly Gly Arg Gln Val Ile Ala Ala Val Lys
                565                 570                 575

TGG GCA AAG GCA ATA CCA GGT TTC AGG AAC TTA CAC CTG GAT GAC CAA      1776
Trp Ala Lys Ala Ile Pro Gly Phe Arg Asn Leu His Leu Asp Asp Gln
        580                 585                 590

ATG ACC CTA CTG CAG TAC TCC TGG ATG TTT CTT ATG GCA TTT GCT CTG      1824
Met Thr Leu Leu Gln Tyr Ser Trp Met Phe Leu Met Ala Phe Ala Leu
        595                 600                 605

GGG TGG AGA TCA TAT AGA CAA TCA AGT GCA AAC CTG CTG TGT TTT GCT      1872
Gly Trp Arg Ser Tyr Arg Gln Ser Ser Ala Asn Leu Leu Cys Phe Ala
        610                 615                 620

CCT GAT CTG ATT ATT AAT GAG CAG AGA ATG ACT CTA CCC TGC ATG TAC      1920
Pro Asp Leu Ile Ile Asn Glu Gln Arg Met Thr Leu Pro Cys Met Tyr
625                 630                 635                 640

GAC CAA TGT AAA CAC ATG CTG TAT GTT TCC TCT GAG TTA CAC AGG CTT      1968
Asp Gln Cys Lys His Met Leu Tyr Val Ser Ser Glu Leu His Arg Leu
                645                 650                 655

CAG GTA TCT TAT GAA GAG TAT CTC TGT ATG AAA ACC TTA CTG CTT CTC      2016
Gln Val Ser Tyr Glu Glu Tyr Leu Cys Met Lys Thr Leu Leu Leu Leu
        660                 665                 670

TCT TCA GTT CCT AAG GAC GGT CTG AAG AGC CAA GAG CTA TTT GAT GAA      2064
Ser Ser Val Pro Lys Asp Gly Leu Lys Ser Gln Glu Leu Phe Asp Glu
        675                 680                 685

ATT AGA ATG ACC TAC ATC AAA GAG CTA GGA AAA GCC ATT GTC AAG AGG      2112
Ile Arg Met Thr Tyr Ile Lys Glu Leu Gly Lys Ala Ile Val Lys Arg
        690                 695                 700

GAA GGA AAC TCC AGC CAG AAC TGG CAG CGG TTT TAT CAA CTG ACA AAA      2160
Glu Gly Asn Ser Ser Gln Asn Trp Gln Arg Phe Tyr Gln Leu Thr Lys
705                 710                 715                 720

CTC TTG GAT TCT ATG CAT GAA GTG GTT GAA AAT CTC CTT AAC TAT TGC      2208
Leu Leu Asp Ser Met His Glu Val Val Glu Asn Leu Leu Asn Tyr Cys
                725                 730                 735

TTC CAA ACA TTT TTG GAT AAG ACC ATG TCC ACC GAG TTC CCC GAG ATG      2256
Phe Gln Thr Phe Leu Asp Lys Thr Met Ser Thr Glu Phe Pro Glu Met
        740                 745                 750

TTA GCT GAA ATC ATC ACC AAT CAG ATA CCA AAA TAT TCA AAT GGA AAT      2304
Leu Ala Glu Ile Ile Thr Asn Gln Ile Pro Lys Tyr Ser Asn Gly Asn
        755                 760                 765

ATC AAA AAA CTT CTG TTT CAT CAA AAG TGA                              2334
Ile Lys Lys Leu Leu Phe His Gln Lys
770                 775
```

(2) INFORMATION FOR SEQ ID NO: 2:

(i) SEQUENCE CHARACTERISTICS:
        (A) LENGTH: 777 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asp Ser Lys Glu Ser Leu Thr Pro Gly Arg Glu Asn Pro Ser
 1               5                  10                  15

Ser Val Leu Ala Gln Glu Arg Gly Asp Val Met Asp Phe Tyr Lys Thr
                20                  25                  30

Leu Arg Gly Gly Ala Thr Val Lys Val Ser Ala Ser Pro Ser Leu
         35                  40                  45

Ala Val Ala Ser Gln Ser Asp Ser Lys Gln Arg Arg Leu Leu Val Asp
     50                  55                  60

Phe Pro Lys Gly Ser Val Ser Asn Ala Gln Gln Pro Asp Leu Ser Lys
 65                  70                  75                  80

Ala Val Ser Leu Ser Met Gly Leu Tyr Met Gly Glu Thr Glu Thr Lys
                 85                  90                  95

Val Met Gly Asn Asp Leu Gly Phe Pro Gln Gln Gly Gln Ile Ser Leu
                100                 105                 110

Ser Ser Gly Glu Thr Asp Leu Lys Leu Leu Glu Glu Ser Ile Ala Asn
                115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
                180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
                260                 265                 270

Leu Pro Gln Val Lys Thr Glu Lys Glu Asp Phe Ile Glu Leu Cys Thr
    275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
                340                 345                 350

Val Ile Pro Pro Ile Pro Val Gly Ser Glu Asn Trp Asn Arg Cys Gln
    355                 360                 365

Gly Ser Gly Asp Asp Asn Leu Thr Ser Leu Gly Thr Leu Asn Phe Pro
370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Gly Pro
                405                 410                 415
```

```
Pro Pro Lys Leu Cys Leu Val Cys Ser Asp Glu Ala Ser Gly Cys His
            420                 425                 430
Tyr Gly Val Leu Thr Cys Gly Ser Cys Lys Val Phe Phe Lys Arg Ala
            435                 440                 445
Val Glu Gly Gln His Asn Tyr Leu Cys Ala Gly Arg Asn Asp Cys Ile
            450                 455                 460
Ile Asp Lys Ile Arg Arg Lys Asn Cys Pro Ala Cys Arg Tyr Arg Lys
465                 470                 475                 480
Cys Leu Gln Ala Gly Met Asn Leu Glu Ala Arg Lys Thr Lys Lys Lys
            485                 490                 495
Ile Lys Gly Ile Gln Gln Ala Thr Thr Gly Val Ser Gln Glu Thr Ser
            500                 505                 510
Glu Asn Pro Gly Asn Lys Thr Ile Val Pro Ala Thr Leu Pro Gln Leu
            515                 520                 525
Thr Pro Thr Leu Val Ser Leu Leu Glu Val Ile Glu Pro Glu Val Leu
            530                 535                 540
Tyr Ala Gly Tyr Asp Ser Ser Val Pro Asp Ser Thr Trp Arg Ile Met
545                 550                 555                 560
Thr Thr Leu Asn Met Leu Gly Gly Arg Gln Val Ile Ala Ala Val Lys
            565                 570                 575
Trp Ala Lys Ala Ile Pro Gly Phe Arg Asn Leu His Leu Asp Asp Gln
            580                 585                 590
Met Thr Leu Leu Gln Tyr Ser Trp Met Phe Leu Met Ala Phe Ala Leu
            595                 600                 605
Gly Trp Arg Ser Tyr Arg Gln Ser Ser Ala Asn Leu Leu Cys Phe Ala
            610                 615                 620
Pro Asp Leu Ile Ile Asn Glu Gln Arg Met Thr Leu Pro Cys Met Tyr
625                 630                 635                 640
Asp Gln Cys Lys His Met Leu Tyr Val Ser Ser Glu Leu His Arg Leu
            645                 650                 655
Gln Val Ser Tyr Glu Glu Tyr Leu Cys Met Lys Thr Leu Leu Leu Leu
            660                 665                 670
Ser Ser Val Pro Lys Asp Gly Leu Lys Ser Gln Glu Leu Phe Asp Glu
            675                 680                 685
Ile Arg Met Thr Tyr Ile Lys Glu Leu Gly Lys Ala Ile Val Lys Arg
            690                 695                 700
Glu Gly Asn Ser Ser Gln Asn Trp Gln Arg Phe Tyr Gln Leu Thr Lys
705                 710                 715                 720
Leu Leu Asp Ser Met His Glu Val Val Glu Asn Leu Leu Asn Tyr Cys
            725                 730                 735
Phe Gln Thr Phe Leu Asp Lys Thr Met Ser Thr Glu Phe Pro Glu Met
            740                 745                 750
Leu Ala Glu Ile Ile Thr Asn Gln Ile Pro Lys Tyr Ser Asn Gly Asn
            755                 760                 765
Ile Lys Lys Leu Leu Phe His Gln Lys
770                 775
```

(2) INFORMATION FOR SEQ ID NO: 3:

(i) SEQUENCE CHARACTERISTICS:
        (A) LENGTH: 2004 base pairs
        (B) TYPE: nucleic acid
        (C) STRANDEDNESS: single
        (D) TOPOLOGY: linear (ii) MOLECULE TYPE: cDNA (ix) FEATURE:
  (A) NAME/KEY: CDS
  (B) LOCATION: 1..2001

(ix) FEATURE:
  (A) NAME/KEY: -
  (B) LOCATION: 1..2001
  (D) OTHER INFORMATION: /note= "CRE-LBD (GR(I747/T) (Fusion protein for the LBD domain of the human glucocorticoid receptor mutated at position 747 and the Cre recombinase protein)."

(xi) SEQUENCE DESCRIPTION: SEQ ID NO: 3:

| | | | | | | | | | | | | | | | | |
|---|---|---|---|---|---|---|---|---|---|---|---|---|---|---|---|---|
| ATG | TCC | AAT | TTA | CTG | ACC | GTA | CAC | CAA | AAT | TTG | CCT | GCA | TTA | CCG | GTC | 48 |
| Met | Ser | Asn | Leu | Leu | Thr | Val | His | Gln | Asn | Leu | Pro | Ala | Leu | Pro | Val | |
| | | 780 | | | | 785 | | | | 790 | | | | | | |
| GAT | GCA | ACG | AGT | GAT | GAG | GTT | CGC | AAG | AAC | CTG | ATG | GAC | ATG | TTC | AGG | 96 |
| Asp | Ala | Thr | Ser | Asp | Glu | Val | Arg | Lys | Asn | Leu | Met | Asp | Met | Phe | Arg | |
| | | 795 | | | | 800 | | | | 805 | | | | | | |
| GAT | CGC | CAG | GCG | TTT | TCT | GAG | CAT | ACC | TGG | AAA | ATG | CTT | CTG | TCC | GTT | 144 |
| Asp | Arg | Gln | Ala | Phe | Ser | Glu | His | Thr | Trp | Lys | Met | Leu | Leu | Ser | Val | |
| 810 | | | | 815 | | | | 820 | | | | 825 | | | | |
| TGC | CGG | TCG | TGG | GCG | GCA | TGG | TGC | AAG | TTG | AAT | AAC | CGG | AAA | TGG | TTT | 192 |
| Cys | Arg | Ser | Trp | Ala | Ala | Trp | Cys | Lys | Leu | Asn | Asn | Arg | Lys | Trp | Phe | |
| | | 830 | | | | 835 | | | | 840 | | | | | | |
| CCC | GCA | GAA | CCT | GAA | GAT | GTT | CGC | GAT | TAT | CTT | CTA | TAT | CTT | CAG | GCG | 240 |
| Pro | Ala | Glu | Pro | Glu | Asp | Val | Arg | Asp | Tyr | Leu | Leu | Tyr | Leu | Gln | Ala | |
| | | | 845 | | | | 850 | | | | 855 | | | | | |
| CGC | GGT | CTG | GCA | GTA | AAA | ACT | ATC | CAG | CAA | CAT | TTG | GGC | CAG | CTA | AAC | 288 |
| Arg | Gly | Leu | Ala | Val | Lys | Thr | Ile | Gln | Gln | His | Leu | Gly | Gln | Leu | Asn | |
| | | 860 | | | | 865 | | | | 870 | | | | | | |
| ATG | CTT | CAT | CGT | CGG | TCC | GGG | CTG | CCA | CGA | CCA | AGT | GAC | AGC | AAT | GCT | 336 |
| Met | Leu | His | Arg | Arg | Ser | Gly | Leu | Pro | Arg | Pro | Ser | Asp | Ser | Asn | Ala | |
| 875 | | | | 880 | | | | 885 | | | | | | | | |
| GTT | TCA | CTG | GTT | ATG | CGG | CGG | ATC | CGA | AAA | GAA | AAC | GTT | GAT | GCC | GGT | 384 |
| Val | Ser | Leu | Val | Met | Arg | Arg | Ile | Arg | Lys | Glu | Asn | Val | Asp | Ala | Gly | |
| 890 | | | | 895 | | | | 900 | | | | 905 | | | | |
| GAA | CGT | GCA | AAA | CAG | GCT | CTA | GCG | TTC | GAA | CGC | ACT | GAT | TTC | GAC | CAG | 432 |
| Glu | Arg | Ala | Lys | Gln | Ala | Leu | Ala | Phe | Glu | Arg | Thr | Asp | Phe | Asp | Gln | |
| | | | 910 | | | | 915 | | | | 920 | | | | | |
| GTT | CGT | TCA | CTC | ATG | GAA | AAT | AGC | GAT | CGC | TGC | CAG | GAT | ATA | CGT | AAT | 480 |
| Val | Arg | Ser | Leu | Met | Glu | Asn | Ser | Asp | Arg | Cys | Gln | Asp | Ile | Arg | Asn | |
| | | | 925 | | | | 930 | | | | 935 | | | | | |
| CTG | GCA | TTT | CTG | GGG | ATT | GCT | TAT | AAC | ACC | CTG | TTA | CGT | ATA | GCC | GAA | 528 |
| Leu | Ala | Phe | Leu | Gly | Ile | Ala | Tyr | Asn | Thr | Leu | Leu | Arg | Ile | Ala | Glu | |
| | | | 940 | | | | 945 | | | | 950 | | | | | |
| ATT | GCC | AGG | ATC | AGG | GTT | AAA | GAT | ATC | TCA | CGT | ACT | GAC | GGT | GGG | AGA | 576 |
| Ile | Ala | Arg | Ile | Arg | Val | Lys | Asp | Ile | Ser | Arg | Thr | Asp | Gly | Gly | Arg | |
| 955 | | | | 960 | | | | 965 | | | | | | | | |
| ATG | TTA | ATC | CAT | ATT | GGC | AGA | ACG | AAA | ACG | CTG | GTT | AGC | ACC | GCA | GGT | 624 |
| Met | Leu | Ile | His | Ile | Gly | Arg | Thr | Lys | Thr | Leu | Val | Ser | Thr | Ala | Gly | |
| 970 | | | | 975 | | | | 980 | | | | 985 | | | | |
| GTA | GAG | AAG | GCA | CTT | AGC | CTG | GGG | GTA | ACT | AAA | CTG | GTC | GAG | CGA | TGG | 672 |
| Val | Glu | Lys | Ala | Leu | Ser | Leu | Gly | Val | Thr | Lys | Leu | Val | Glu | Arg | Trp | |
| | | | 990 | | | | 995 | | | | 1000 | | | | | |
| ATT | TCC | GTC | TCT | GGT | GTA | GCT | GAT | GAT | CCG | AAT | AAC | TAC | CTG | TTT | TGC | 720 |
| Ile | Ser | Val | Ser | Gly | Val | Ala | Asp | Asp | Pro | Asn | Asn | Tyr | Leu | Phe | Cys | |
| | | | 1005 | | | | 1010 | | | | 1015 | | | | | |
| CGG | GTC | AGA | AAA | AAT | GGT | GTT | GCC | GCG | CCA | TCT | GCC | ACC | AGC | CAG | CTA | 768 |
| Arg | Val | Arg | Lys | Asn | Gly | Val | Ala | Ala | Pro | Ser | Ala | Thr | Ser | Gln | Leu | |
| | | | 1020 | | | | 1025 | | | | 1030 | | | | | |

```
TCA ACT CGC GCC CTG GAA GGG ATT TTT GAA GCA ACT CAT CGA TTG ATT      816
Ser Thr Arg Ala Leu Glu Gly Ile Phe Glu Ala Thr His Arg Leu Ile
    1035                1040                1045

TAC GGC GCT AAG GAT GAC TCT GGT CAG AGA TAC CTG GCC TGG TCT GGA      864
Tyr Gly Ala Lys Asp Asp Ser Gly Gln Arg Tyr Leu Ala Trp Ser Gly
1050                1055                1060                1065

CAC AGT GCC CGT GTC GGA GCC GCG CGA GAT ATG GCC CGC GCT GGA GTT      912
His Ser Ala Arg Val Gly Ala Ala Arg Asp Met Ala Arg Ala Gly Val
            1070                1075                1080

TCA ATA CCG GAG ATC ATG CAA GCT GGT GGC TGG ACC AAT GTA AAT ATT      960
Ser Ile Pro Glu Ile Met Gln Ala Gly Gly Trp Thr Asn Val Asn Ile
        1085                1090                1095

GTC ATG AAC TAT ATC CGT AAC CTG GAT AGT GAA ACA GGG GCA ATG GTG     1008
Val Met Asn Tyr Ile Arg Asn Leu Asp Ser Glu Thr Gly Ala Met Val
    1100                1105                1110

CGC CTG CTG GAA GAT GGC GAT CTC GAG ATT CAG CAG GCC ACT ACA GGA     1056
Arg Leu Leu Glu Asp Gly Asp Leu Glu Ile Gln Gln Ala Thr Thr Gly
1115                1120                1125

GTC TCA CAA GAA ACC TCT GAA AAT CCT GGT AAC AAA ACA ATA GTT CCT     1104
Val Ser Gln Glu Thr Ser Glu Asn Pro Gly Asn Lys Thr Ile Val Pro
1130                1135                1140                1145

GCA ACG TTA CCA CAA CTC ACC CCT ACC CTG GTG TCA CTG TTG GAG GTT     1152
Ala Thr Leu Pro Gln Leu Thr Pro Thr Leu Val Ser Leu Leu Glu Val
            1150                1155                1160

ATT GAA CCT GAA GTG TTA TAT GCA GGA TAT GAT AGC TCT GTT CCA GAC     1200
Ile Glu Pro Glu Val Leu Tyr Ala Gly Tyr Asp Ser Ser Val Pro Asp
        1165                1170                1175

TCA ACT TGG AGG ATC ATG ACT ACG CTC AAC ATG TTA GGA GGG CGG CAA     1248
Ser Thr Trp Arg Ile Met Thr Thr Leu Asn Met Leu Gly Gly Arg Gln
    1180                1185                1190

GTG ATT GCA GCA GTG AAA TGG GCA AAG GCA ATA CCA GGT TTC AGG AAC     1296
Val Ile Ala Ala Val Lys Trp Ala Lys Ala Ile Pro Gly Phe Arg Asn
1195                1200                1205

TTA CAC CTG GAT GAC CAA ATG ACC CTA CTG CAG TAC TCC TGG ATG TTT     1344
Leu His Leu Asp Asp Gln Met Thr Leu Leu Gln Tyr Ser Trp Met Phe
1210                1215                1220                1225

CTT ATG GCA TTT GCT CTG GGG TGG AGA TCA TAT AGA CAA TCA AGT GCA     1392
Leu Met Ala Phe Ala Leu Gly Trp Arg Ser Tyr Arg Gln Ser Ser Ala
            1230                1235                1240

AAC CTG CTG TGT TTT GCT CCT GAT CTG ATT ATT AAT GAG CAG AGA ATG     1440
Asn Leu Leu Cys Phe Ala Pro Asp Leu Ile Ile Asn Glu Gln Arg Met
        1245                1250                1255

ACT CTA CCC TGC ATG TAC GAC CAA TGT AAA CAC ATG CTG TAT GTT TCC     1488
Thr Leu Pro Cys Met Tyr Asp Gln Cys Lys His Met Leu Tyr Val Ser
    1260                1265                1270

TCT GAG TTA CAC AGG CTT CAG GTA TCT TAT GAA GAG TAT CTC TGT ATG     1536
Ser Glu Leu His Arg Leu Gln Val Ser Tyr Glu Glu Tyr Leu Cys Met
1275                1280                1285

AAA ACC TTA CTG CTT CTC TCT TCA GTT CCT AAG GAC GGT CTG AAG AGC     1584
Lys Thr Leu Leu Leu Leu Ser Ser Val Pro Lys Asp Gly Leu Lys Ser
1290                1295                1300                1305

CAA GAG CTA TTT GAT GAA ATT AGA ATG ACC TAC ATC AAA GAG CTA GGA     1632
Gln Glu Leu Phe Asp Glu Ile Arg Met Thr Tyr Ile Lys Glu Leu Gly
            1310                1315                1320

AAA GCC ATT GTC AAG AGG GAA GGA AAC TCC AGC CAG AAC TGG CAG CGG     1680
Lys Ala Ile Val Lys Arg Glu Gly Asn Ser Ser Gln Asn Trp Gln Arg
        1325                1330                1335

TTT TAT CAA CTG ACA AAA CTC TTG GAT TCT ATG CAT GAA GTG GTT GAA     1728
Phe Tyr Gln Leu Thr Lys Leu Leu Asp Ser Met His Glu Val Val Glu
    1340                1345                1350
```

```
AAT CTC CTT AAC TAT TGC TTC CAA ACA TTT TTG GAT AAG ACC ATG TCC      1776
Asn Leu Leu Asn Tyr Cys Phe Gln Thr Phe Leu Asp Lys Thr Met Ser
        1355                1360                1365

ACC GAG TTC CCC GAG ATG TTA GCT GAA ATC ATC ACC AAT CAG ATA CCA      1824
Thr Glu Phe Pro Glu Met Leu Ala Glu Ile Ile Thr Asn Gln Ile Pro
1370                1375                1380                1385

AAA TAT TCA AAT GGA AAT ATC AAA AAA CTT CTG TTT CAT CAA AAG GGT      1872
Lys Tyr Ser Asn Gly Asn Ile Lys Lys Leu Leu Phe His Gln Lys Gly
                1390                1395                1400

ACC AGC CGT GGA GGG GCA TCC GTG GAG GAG ACG GAC CAA AGC CAC TTG      1920
Thr Ser Arg Gly Gly Ala Ser Val Glu Glu Thr Asp Gln Ser His Leu
            1405                1410                1415

GCC ACT GCG GGC TCT ACT TCA TCG CAT TCC TTG CAA AAG TAT TAC ATC      1968
Ala Thr Ala Gly Ser Thr Ser Ser His Ser Leu Gln Lys Tyr Tyr Ile
        1420                1425                1430

ACG GGG GAG GCA GAG GGT TTC CCT GCC ACA GTC TGA                      2004
Thr Gly Glu Ala Glu Gly Phe Pro Ala Thr Val
    1435                1440
```

(2) INFORMATION FOR SEQ ID NO: 4:

(i) SEQUENCE CHARACTERISTICS:
        (A) LENGTH: 667 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Asn Leu Leu Thr Val His Gln Asn Leu Pro Ala Leu Pro Va
 1               5                  10                 15

Asp Ala Thr Ser Asp Glu Val Arg Lys Asn Leu Met Asp Met Phe Arg
                20                  25                 30

Asp Arg Gln Ala Phe Ser Glu His Thr Trp Lys Met Leu Leu Ser Val
            35                  40                 45

Cys Arg Ser Trp Ala Ala Trp Cys Lys Leu Asn Asn Arg Lys Trp Phe
     50                  55                  60

Pro Ala Glu Pro Glu Asp Val Arg Asp Tyr Leu Leu Tyr Leu Gln Ala
65                  70                  75                 80

Arg Gly Leu Ala Val Lys Thr Ile Gln Gln His Leu Gly Gln Leu Asn
                85                  90                 95

Met Leu His Arg Arg Ser Gly Leu Pro Arg Pro Ser Asp Ser Asn Ala
            100                 105                110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220
```

-continued

```
Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
            245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp Leu Glu Ile Gln Gln Ala Thr Thr Gly
                340                 345                 350

Val Ser Gln Glu Thr Ser Glu Asn Pro Gly Asn Lys Thr Ile Val Pro
            355                 360                 365

Ala Thr Leu Pro Gln Leu Thr Pro Thr Leu Val Ser Leu Leu Glu Val
370                 375                 380

Ile Glu Pro Glu Val Leu Tyr Ala Gly Tyr Asp Ser Ser Val Pro Asp
385                 390                 395                 400

Ser Thr Trp Arg Ile Met Thr Thr Leu Asn Met Leu Gly Gly Arg Gln
                405                 410                 415

Val Ile Ala Ala Val Lys Trp Ala Lys Ala Ile Pro Gly Phe Arg Asn
            420                 425                 430

Leu His Leu Asp Asp Gln Met Thr Leu Leu Gln Tyr Ser Trp Met Phe
        435                 440                 445

Leu Met Ala Phe Ala Leu Gly Trp Arg Ser Tyr Arg Gln Ser Ser Ala
        450                 455                 460

Asn Leu Leu Cys Phe Ala Pro Asp Leu Ile Ile Asn Glu Gln Arg Met
465                 470                 475                 480

Thr Leu Pro Cys Met Tyr Asp Gln Cys Lys His Met Leu Tyr Val Ser
                485                 490                 495

Ser Glu Leu His Arg Leu Gln Val Ser Tyr Glu Glu Tyr Leu Cys Met
            500                 505                 510

Lys Thr Leu Leu Leu Leu Ser Ser Val Pro Lys Asp Gly Leu Lys Ser
            515                 520                 525

Gln Glu Leu Phe Asp Glu Ile Arg Met Thr Tyr Ile Lys Glu Leu Gly
            530                 535                 540

Lys Ala Ile Val Lys Arg Glu Gly Asn Ser Ser Gln Asn Trp Gln Arg
545                 550                 555                 560

Phe Tyr Gln Leu Thr Lys Leu Leu Asp Ser Met His Glu Val Val Glu
                565                 570                 575

Asn Leu Leu Asn Tyr Cys Phe Gln Thr Phe Leu Asp Lys Thr Met Ser
                580                 585                 590

Thr Glu Phe Pro Glu Met Leu Ala Glu Ile Ile Thr Asn Gln Ile Pro
            595                 600                 605

Lys Tyr Ser Asn Gly Asn Ile Lys Lys Leu Leu Phe His Gln Lys Gly
            610                 615                 620

Thr Ser Arg Gly Gly Ala Ser Val Glu Glu Thr Asp Gln Ser His Leu
625                 630                 635                 640
```

-continued

```
Ala Thr Ala Gly Ser Thr Ser Ser His Ser Leu Gln Lys Tyr Tyr Ile
                645                 650                 655

Thr Gly Glu Ala Glu Gly Phe Pro Ala Thr Val
            660                 665
```

(2) INFORMATION FOR SEQ ID NO: 5:

(i) SEQUENCE CHARACTERISTICS:
        (A) LENGTH: 6094 base pairs
        (B) TYPE: nucleic acid
        (C) STRANDEDNESS: single
        (D) TOPOLOGY: circular (ii) MOLECULE TYPE: cDNA (ix) FEATURE:
        (A) NAME/KEY: -
        (B) LOCATION: 1..6091
        (D) OTHER INFORMATION: /note= "pCRE-LBD[GR(I747/T]
        (Plasmid for expressing the fusion protein Cre-LBD
        T)]."

(xi) SEQUENCE DESCRIPTION: SEQ ID NO: 5:

```
GTCGACTTCT GAGGCGGAAA GAACCAGCTG TGGAATGTGT GTCAGTTAGG GTGTGGAAAG      60

TCCCCAGGCT CCCCAGCAGG CAGAAGTATG CAAAGCATGC ATCTCAATTA GTCAGCAAC      120

AGGTGTGGAA AGTCCCCAGG CTCCCCAGCA GGCAGAAGTA TGCAAAGCAT GCATCTCAA      180

TAGTCAGCAA CCATAGTCCC GCCCCTAACT CCGCCCATCC CGCCCCTAAC TCCGCCCAG      240

TCCGCCCATT CTCCGCCCCA TGGCTGACTA ATTTTTTTTA TTTATGCAGA GGCCGAGGC      300

GCCTCGGCCT CTGAGCTATT CCAGAAGTAG TGAGGAGGCT TTTTTGGAGG CCTAGGCTT      360

TGCAAAAAGC TGGATCGATC CTGAGAACTT CAGGGTGAGT TTGGGGACCC TTGATTGTT      420

TTTCTTTTTC GCTATTGTAA AATTCATGTT ATATGGAGGG GGCAAAGTTT TCAGGGTGT      480

GTTTAGAATG GGAAGATGTC CCTTGTATCA CCATGGACCC TCATGATAAT TTTGTTTCT      540

TCACTTTCTA CTCTGTTGAC AACCATTGTC TCCTCTTATT TTCTTTTCAT TTTCTGTAA      600

TTTTTCGTTA AACTTTAGCT TGCATTTGTA ACGAATTTTT AAATTCACTT TGTTTATT       660

GTCAGATTGT AAGTACTTTC TCTAATCACT TTTTTTTCAA GGCAATCAGG GTATATTAT      720

TTGTACTTCA GCACAGTTTT AGAGAACAAT TGTTATAATT AAATGATAAG GTAGAATAT      780

TCTGCATATA AATTCTGGCT GGCGTGGAAA TATTCTTATT GGTAGAAACA ACTACATCC      840

GGTCATCATC CTGCCTTTCT CTTTATGGTT ACAATGATAT ACACTGTTTG AGATGAGGA      900

AAAATACTCT GAGTCCAAAC CGGGCCCCTC TGCTAACCAT GTTCATGCCT TCTTCTTTT      960

CCTACAGCTC CTGGGCAACG TGCTGGTTAT TGTGCTGTCT CATCATTTTG GCAAAGAA      1020

GTAATACGAC TCACTATAGG GCGAATTCCA CCATGTCCAA TTTACTGACC GTACACCA      1080

ATTTGCCTGC ATTACCGGTC GATGCAACGA GTGATGAGGT TCGCAAGAAC CTGATGGA      1140

TGTTCAGGGA TCGCCAGGCG TTTTCTGAGC ATACCTGGAA AATGCTTCTG TCCGTTTG      1200

GGTCGTGGGC GGCATGGTGC AAGTTGAATA ACCGGAAATG GTTTCCCGCA GAACCTGA      1260

ATGTTCGCGA TTATCTTCTA TATCTTCAGG CGCGCGGTCT GGCAGTAAAA ACTATCCA      1320

AACATTTGGG CCAGCTAAAC ATGCTTCATC GTCGGTCCGG GCTGCCACGA CCAAGTGA      1380

GCAATGCTGT TTCACTGGTT ATGCGGCGGA TCCGAAAAGA AAACGTTGAT GCCGGTGA      1440

GTGCAAAACA GGCTCTAGCG TTCGAACGCA CTGATTTCGA CCAGGTTCGT TCACTCAT      1500

AAAATAGCGA TCGCTGCCAG GATATACGTA ATCTGGCATT TCTGGGGATT GCTTATAA      1560

CCCTGTTACG TATAGCCGAA ATTGCCAGGA TCAGGGTTAA AGATATCTCA CGTACTGA      1620
```

```
GTGGGAGAAT GTTAATCCAT ATTGGCAGAA CGAAAACGCT GGTTAGCACC GCAGGTGT    1680

AGAAGGCACT TAGCCTGGGG GTAACTAAAC TGGTCGAGCG ATGGATTTCC GTCTCTGG    1740

TAGCTGATGA TCCGAATAAC TACCTGTTTT GCCGGGTCAG AAAAAATGGT GTTGCCGC    1800

CATCTGCCAC CAGCCAGCTA TCAACTCGCG CCCTGGAAGG GATTTTTGAA GCAACTCA    1860

GATTGATTTA CGGCGCTAAG GATGACTCTG GTCAGAGATA CCTGGCCTGG TCTGGACA    1920

GTGCCCGTGT CGGAGCCGCG CGAGATATGG CCCGCGCTGG AGTTTCAATA CCGGAGAT    1980

TGCAAGCTGG TGGCTGGACC AATGTAAATA TTGTCATGAA CTATATCCGT AACCTGGA    2040

GTGAAACAGG GGCAATGGTG CGCCTGCTGG AAGATGGCGA TCTCGAGATT CAGCAGGC    2100

CTACAGGAGT CTCACAAGAA ACCTCTGAAA ATCCTGGTAA CAAAACAATA GTTCCTGC    2160

CGTTACCACA ACTCACCCCT ACCCTGGTGT CACTGTTGGA GGTTATTGAA CCTGAAGT    2220

TATATGCAGG ATATGATAGC TCTGTTCCAG ACTCAACTTG CAGGATCATG ACTACGCT    2280

ACATGTTAGG AGGGCGGCAA GTGATTGCAG CAGTGAAATG GGCAAAGGCA ATACCAGG    2340

TCAGGAACTT ACACCTGGAT GACCAAATGA CCCTACTGCA GTACTCCTGG ATGTTTCT    2400

TGGCATTTGC TCTGGGGTGG AGATCATATA GACAATCAAG TGCAAACCTG CTGTGTTT    2460

CTCCTGATCT GATTATTAAT GAGCAGAGAA TGACTCTACC CTGCATGTAC GACCAATG    2520

AACACATGCT GTATGTTTCC TCTGAGTTAC ACAGGCTTCA GGTATCTTAT GAAGAGTA    2580

TCTGTATGAA AACCTTACTG CTTCTCTCTT CAGTTCCTAA GGACGGTCTG AAGAGCCA    2640

AGCTATTTGA TGAAATTAGA ATGACCTACA TCAAAGAGCT AGGAAAAGCC ATTGTCAA    2700

GGGAAGGAAA CTCCAGCCAG AACTGGCAGC GGTTTTATCA ACTGACAAAA CTCTTGGA    2760

CTATGCATGA AGTGGTTGAA AATCTCCTTA ACTATTGCTT CCAAACATTT TTGGATAA    2820

CCATGTCCAC CGAGTTCCCC GAGATGTTAG CTGAAATCAT CACCAATCAG ATACCAAA    2880

ATTCAAATGG AAATATCAAA AAACTTCTGT TTCATCAAAA GGGTACCAGC CGTGGAGG    2940

CATCCGTGGA GGAGACGGAC CAAAGCCACT TGGCCACTGC GGGCTCTACT TCATCGCA    3000

CCTTGCAAAA GTATTACATC ACGGGGGAGG CAGAGGGTTT CCCTGCCACA GTCTGAGA    3060

TCCCTGGAAT TCGGATCTTA TTAAAGCAGA ACTTGTTTAT TGCAGCTTAT AATGGTTA    3120

AATAAAGCAA TAGCATCACA AATTTCACAA ATAAAGCATT TTTTTCACTG CATTCTAG    3180

GTGGTTTGTC CAAACTCATC AATGTATCTT ATCATGTCTG GTCGACTCTA GACTCTTC    3240

CTTCCTCGCT CACTGACTCG CTGCGCTCGG TCGTTCGGCT GCGGCGAGCG GTATCAGC    3300

ACTCAAAGGC GGTAATACGG TTATCCACAG AATCAGGGGA TAACGCAGGA AGAACAT    3360

CAGCAAAAGG CCAGCAAAAG GCCAGGAACC GTAAAAAGGC CGCGTTGCTG GCGTTTTT    3420

ATAGGCTCCG CCCCCCTGAC GAGCATCACA AAAATCGACG CTCAAGTCAG AGGTGGCG    3480

ACCCGACAGG ACTATAAAGA TACCAGGCGT TTCCCCCTGG AAGCTCCCTC GTGCGCTC    3540

CTGTTCCGAC CCTGCCGCTT ACCGGATACC TGTCCGCCTT TCTCCCTTCG GGAAGCGT    3600

CGCTTTCTCA TAGCTCACGC TGTAGGTATC TCAGTTCGGT GTAGGTCGTT CGCTCCAA    3660

TGGGCTGTGT GCACGAACCC CCCGTTCAGC CCGACCGCTG CGCCTTATCC GGTAACTA    3720

GTCTTGAGTC CAACCCGGTA AGACACGACT TATCGCCACT GGCAGCAGCC ACTGGTAA    3780

GGATTAGCAG AGCGAGGTAT GTAGGCGGTG CTACAGAGTT CTTGAAGTGG TGGCCTAA    3840

ACGGCTACAC TAGAAGGACA GTATTTGGTA TCTGCGCTCT GCTGAAGCCA GTTACCTT    3900

GAAAAAGAGT TGGTAGCTCT TGATCCGGCA AACAAACCAC CGCTGGTAGC GGTGGTTT    3960

TTGTTTGCAA GCAGCAGATT ACGCGCAGAA AAAAAGGATC TCAAGAAGAT CCTTTGAT    4020
```

```
TTTCTACGGG GTCTGACGCT CAGTGGAACG AAAACTCACG TTAAGGGATT TTGGTCAT      4080

GATTATCAAA AAGGATCTTC ACCTAGATCC TTTTAAATTA AAAATGAAGT TTTAAATC      4140

TCTAAAGTAT ATATGAGTAA ACTTGGTCTG ACAGTTACCA ATGCTTAATC AGTGAGGC      4200

CTATCTCAGC GATCTGTCTA TTTCGTTCAT CCATAGTTGC CTGACTCCCC GTCGTGTA      4260

TAACTACGAT ACGGGAGGGC TTACCATCTG GCCCCAGTGC TGCAATGATA CCGCGAGA      4320

CACGCTCACC GGCTCCAGAT TTATCAGCAA TAAACCAGCC AGCCGGAAGG GCCGAGCG      4380

GAAGTGGTCC TGCAACTTTA TCCGCCTCCA TCCAGTCTAT TAATTGTTGC CGGGAAGC      4440

GAGTAAGTAG TTCGCCAGTT AATAGTTTGC GCAACGTTGT TGCCATTGCT ACAGGCAT      4500

TGGTGTCACG CTCGTCGTTT GGTATGGCTT CATTCAGCTC CGGTTCCCAA CGATCAAG      4560

GAGTTACATG ATCCCCCATG TTGTGCAAAA AAGCGGTTAG CTCCTTCGGT CCTCCGAT      4620

TTGTCAGAAG TAAGTTGGCC GCAGTGTTAT CACTCATGGT TATGGCAGCA CTGCATAA      4680

CTCTTACTGT CATGCCATCC GTAAGATGCT TTTCTGTGAC TGGTGAGTAC TCAACCAA      4740

CATTCTGAGA ATAGTGTATG CGGCGACCGA GTTGCTCTTG CCCGGCGTCA ATACGGGA      4800

ATACCGCGCC ACATAGCAGA ACTTTAAAAG TGCTCATCAT TGGAAAACGT TCTTCGGG      4860

GAAAACTCTC AAGGATCTTA CCGCTGTTGA GATCCAGTTC GATGTAACCC ACTCGTGC      4920

CCAACTGATC TTCAGCATCT TTTACTTTCA CCAGCGTTTC TGGGTGAGCA AAAACAGG      4980

GGCAAAATGC CGCAAAAAAG GGAATAAGGG CGACACGGAA ATGTTGAATA CTCATACT      5040

TCCTTTTTCA ATATTATTGA AGCATTTATC AGGGTTATTG TCTCATGAGC GGATACAT      5100

TTGAATGTAT TTAGAAAAAT AAACAAATAG GGGTTCCGCG CACATTTCCC CGAAAAGT      5160

CACCTGACGT CTAAGAAACC ATTATTATCA TGACATTAAC CTATAAAAAT AGGCGTAT      5220

CGAGGCCCCT TCGTCTCGC GCGTTTCGGT GATGACGGTG AAAACCTCTG ACACATGC       5280

CTCCCGGAGA CGGTCACAGC TTGTCTGTAA GCGGATGCCG GGAGCAGACA AGCCCGTC      5340

GGCGCGTCAG CGGGTGTTGG CGGGTGTCGG GGCTGGCTTA ACTATGCGGC ATCAGAGC      5400

ATTGTACTGA GAGTGCACCA TATGCGGTGT GAAATACCGC ACAGATGCGT AAGGAGAA      5460

TACCGCATCA GGAAATTGTA AACGTTAATA TTTTGTTAAA ATTCGCGTTA AATTTTTG      5520

AAATCAGCTC ATTTTTTAAC CAATAGGCCG AAATCGGCAA AATCCCTTAT AAATCAAA      5580

AATAGACCGA GATAGGGTTG AGTGTTGTTC CAGTTTGGAA CAAGAGTCCA CTATTAAA      5640

ACGTGGACTC CAACGTCAAA GGGCGAAAAA CCGTCTATCA GGGCGATGGC CCACTACG      5700

AACCATCACC CTAATCAAGT TTTTTGGGGT CGAGGTGCCG TAAAGCACTA AATCGGAA      5760

CTAAAGGGAG CCCCCGATTT AGAGCTTGAC GGGGAAAGCC GGCGAACGTG GCGAGAAA      5820

AAGGGAAGAA AGCGAAAGGA GCGGGCGCTA GGGCGCTGGC AAGTGTAGCG GTCACGCT      5880

GCGTAACCAC CACACCCGCC GCGCTTAATG CGCCGCTACA GGGCGCGTCG CGCCATTC      5940

CATTCAGGCT GCGCAACTGT TGGGAAGGGC GATCGGTGCG GGCCTCTTCG CTATTACG      6000

AGCTGGCGAA AGGGGGATGT GCTGCAAGGC GATTAAGTTG GGTAACGCCA GGGTTTTC      6060

AGTCACGACG TTGTAAAACG ACGGCCAGTG AATT                                6094
```

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear

```
        (ii) MOLECULE TYPE: DNA (genomic)

(ix) FEATURE:
            (A) NAME/KEY: -
            (B) LOCATION: 1..36
            (D) OTHER INFORMATION: /note= "SG52"

(xi) SEQUENCE DESCRIPTION: SEQ ID NO: 6:

CTGGAAGATG GCGATCTCGA GATTCAGCAG GCCACT                              36

(2) INFORMATION FOR SEQ ID NO: 7:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..37
            (D) OTHER INFORMATION: /note= "SG53"

(xi) SEQUENCE DESCRIPTION: SEQ ID NO: 7:

CTGTTTCATC AAAAGGGTAC CAGCCGTGGA GGGGCAT                             37

(2) INFORMATION FOR SEQ ID NO: 8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..24
            (D) OTHER INFORMATION: /note= "synthetic oligonucleotide"

(xi) SEQUENCE DESCRIPTION: SEQ ID NO: 8:

ATTATTATTA CTCGAGTGAT GATG                                           24

(2) INFORMATION FOR SEQ ID NO: 9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..24
            (D) OTHER INFORMATION: /note= "synthetic oligonucleotide"

(xi) SEQUENCE DESCRIPTION: SEQ ID NO: 9:

ATCATCATCA TCCGAGTAAT AATA                                           24

(2) INFORMATION FOR SEQ ID NO: 10:

(i) SEQUENCE CHARACTERISTICS:
            (A) LENGTH: 14 base pairs
            (B) TYPE: nucleic acid
            (C) STRANDEDNESS: single
            (D) TOPOLOGY: linear
```

(ii) MOLECULE TYPE: DNA (genomic)

(ix) FEATURE:
            (A) NAME/KEY: -
            (B) LOCATION: 1..14
            (D) OTHER INFORMATION: /note= "SB211"

(xi) SEQUENCE DESCRIPTION: SEQ ID NO: 10:

GGCAAACACT ATGG                                                           14

(2) INFORMATION FOR SEQ ID NO: 11:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..17
            (D) OTHER INFORMATION: /note= "PZ105"

(xi) SEQUENCE DESCRIPTION: SEQ ID NO: 11:

TTGCGTACTG TCCTCTT                                                        17

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "synthetic oligonucleotide"

(xi) SEQUENCE DESCRIPTION: SEQ ID NO: 12:

AAGAAGCCCT TGCAGCCCTC                                                     20

(2) INFORMATION FOR SEQ ID NO: 13:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..40
            (D) OTHER INFORMATION: /note= "synthetic oligonucleotide"

(xi) SEQUENCE DESCRIPTION: SEQ ID NO: 13:

AATTATAACT TCGTATAATG TATGCTATAC GAAGTTATTC                                40

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "primer"

(xi) SEQUENCE DESCRIPTION: SEQ ID NO: 14:

ATCCGAAAAG AAAACGTTGA                                                           20

(2) INFORMATION FOR SEQ ID NO: 15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "primer"

(xi) SEQUENCE DESCRIPTION: SEQ ID NO: 15:

ATCCAGGTTA CGGATATAGT                                                           20

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "primer"

(xi) SEQUENCE DESCRIPTION: SEQ ID NO: 16:

GGTTCTCCGG CCGCTTGGGT                                                           20

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "primer"

(xi) SEQUENCE DESCRIPTION: SEQ ID NO: 17:

GAAGGCGATG CGCTGCGAAT                                                           20

(2) INFORMATION FOR SEQ ID NO: 18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear -continued

```
    (ii) MOLECULE TYPE: DNA (genomic)

(ix) FEATURE:
         (A) NAME/KEY: -
         (B) LOCATION: 1..20
         (D) OTHER INFORMATION: /note= "primer A"

(xi) SEQUENCE DESCRIPTION: SEQ ID NO: 18:

CAAGGAGCCT CCTTTCTCTA                                              20

(2) INFORMATION FOR SEQ ID NO: 19:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: -
         (B) LOCATION: 1..20
         (D) OTHER INFORMATION: /note= "primer B"

(xi) SEQUENCE DESCRIPTION: SEQ ID NO: 19:

CCTGCTCTAC CTGGTGACTT                                              20
```